US006245746B1

(12) United States Patent
Chamberland et al.

(10) Patent No.: US 6,245,746 B1
(45) Date of Patent: *Jun. 12, 2001

(54) EFFLUX PUMP INHIBITORS

(75) Inventors: Suzanne Chamberland, Los Gatos; May Lee, Los Altos; Roger Leger, Mountain View; Ving J. Lee, Los Altos; Thomas Renau, Santa Clara; Zhijia J. Zhang, Foster City, all of CA (US)

(73) Assignee: Microcide Pharmaceuticals, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/020,001

(22) Filed: Feb. 4, 1998

Related U.S. Application Data

(63) Continuation-in-part of application No. 09/012,363, filed on Jan. 23, 1998, now Pat. No. 6,114,310.

(51) Int. Cl.$^7$ .......................... A61K 31/70; A61K 38/16; A61K 31/47; A61K 31/24; A61K 31/225

(52) U.S. Cl. .................................. 514/39; 514/8; 514/23; 514/152; 514/311; 514/537; 514/547

(58) Field of Search .............................. 514/39, 152, 311, 514/8, 23, 537, 547

(56) References Cited

FOREIGN PATENT DOCUMENTS

9633285 * 10/1996 (WO).

OTHER PUBLICATIONS

Ahmed et al., "A Protein That Activates Expression of a Multidrug Efflux Transporter upon Binding the Transporter Substrates," *J. Biol. Chem.* 269:28506–28513 (1994).
Day et al., "A simple method for the study in vivo of bacterial growth and accompanying host response," *Journal of Infection* 2:39–51 (1980).
Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).
Kelly et al., "Surface Characteristics of *Pseudomonas aeruginosa* Grown in a Chamber Implant Model in Mice and Rats," *Infection and Immunity* 57:344–350 (1989).
Lorian (editor), "Laboratory Methods Used to Assess the Activity of Antimicrobial Combinations," in *Antibiotics in Laboratory Medicine*, Fourth Edition, Williams & Wilkins, pp. 333–338 (1996).
Malouin et al., "Outer Membrane and Porin Characteristics of *Serratia marcescens* Grown In Vitro and in Rat Intraperitoneal Diffusion Chambers," *Infection and Immunity* 58:1247–1253 (1990).
Murray, "Can Antibiotic Resistance be Controlled?" *New Engl. J. Med.* 330:1229–1230 (1994).

NCCLS publication entitled "Methods for Dilution Antimicrobial Susceptibility Test for Bacteria that Grow Aerobically—Fourth Edition: Approved Standard," NCCLS Document M7–A4, vol. 17, No. 2 (1997).
Nikaido, "Prevention of Drug Access to Bacterial Targets: Permeability Barriers and Active Efflux," *Science* 264:382–388 (1994.
Reitz et al., "The Biochemical Mechanisms of Resistance by Streptococci to the Antibiotics D–Cycloserine and O–Carbamyl–D–Serine," *Biochem. J.* 6:2561–2570 (1967).
Santoro and Levison, "Rat Model of Experimental Endocarditis," *Infection and Immunity* 19:915–918 (1978).
Sato et al., "Antimicrobial Activity of DU–6859, a New Potent Fluoroquinolone, against Clinical Isolates," *Antimicrobial Agents and Chemotherapy* 36:1491–1498 (1992).
Seoane and Levy, "Reversal of MarR binding to the regulatory region of the *marRAB* operon by structurally unrelated inducers," *Abstr. of the Am. Soc. for Microbiol. Gen. Meeting*, Las Vegas, NV Abstract H–26 (1994).
Spratt, "Resistance to Antibiotics Mediated by Target Alterations," *Science* 264:388–393 (1994).
Tanaka et al., "Antimicrobial Activity of DV–7751a, a New Fluoroquinolone," *Antimicrobial Agents and Chemotherapy* 37:2112–2218 (1993).
Trias et al., Patent Application, Ser. No. 08/427,088 filed Apr. 21, 1995 for "Efflux Pump Inhibitors".
Trias et al., Patent Application, Ser. No. 08/898,477 filed Jul. 22, 1997 for "Efflux Pump Inhibitors".
Speer et al., "Bacterial Resistance to Tetracycline: Mechanisms, Transfer, and Clinical Significance," *Clin. Microbiol. Rev.* 5:387–399 (1992).
Vogelman et al., "In Vivo Postantibiotic Effect in a Thigh Infection in Neutropenic Mice," *J. Infect. Dis.* 157:287–298 (1988).
Williams, R.M., *Synthesis of Optically Active α–Amino Acids*, Pergamon Press, Oxford, U.K.
Wu et al., "An Efficient Method for the Preparation of ω,ω–BIS–Urethane Protected Arginine Derivatives," *Synth. Comm.*, 23:3055 (1993).
Xue et al., "Novel Synthesis of Nα–Methyl–arginine and Nα–Methyl–ornithine Derivatives," *Tetrahedron Lett.*, 36:55 (1995).
Bailey, P.D., *Introduction to Peptide Chemistry*, John Wiley and Sons, NY, NY (1992).
Bergeron, M.G., "A Review of Models for the Therapy of Experimental Infections," *Scand. J. Infect. Dis. Suppl.* 14:189–206 (1978).
Bodanszky, M., et al., *Practice of Peptide Synthesis*, Springer–Verlag, NY, NY (1984).
Coppola, G.M., et al., *Asymmetric Synthesis: Construction of Chiral Molecules Using Amino Acids*, John Wiley and Sons, NY, NY (1987).

(List continued on next page.)

Primary Examiner—Kevin E. Weddington
(74) Attorney, Agent, or Firm—Lyon & Lyon LLP

(57) ABSTRACT

Compounds are described which have efflux pump inhibitor activity. Also described are methods of using such efflux pump inhibitor compounds and pharmaceutical compositions which include such compounds.

35 Claims, No Drawings

OTHER PUBLICATIONS

Davis, "Activity of Gentamicin, Tobramycin, Polymyxin B, and Colistimethate in Mouse Protection Tests with Pseudomonas Aeruginosa," *Antimicrob. Agents Chemother.* 8:50–53 (1975).

Gilman et al., Eds., *The Pharamacological Basis of Therapeutics*, $8^{th}$ Ed., Pergamon Press (1990).

Gordon, E.M., et al., "Design of Novel Inhibitors of Aminopeptidases. Synthesis of Peptide–Derived Diamino Thiols and Sulfur Replacement Analogues of Bestatin," *J. Med. Chem.* 31:2199–2210 (1988).

Greene, T., and P. Wuts, *Protective Groups in Organic Synthesis*, $2^{nd}$ Edition, John Wiley & Sons, Inc. (Index) (1991).

Greenstein, J.P. and M. Winitz, *Chemistry of the Amino Acids*, Wiley and Sons, Inc., NY, NY (1961).

Jones, J., *The Chemical Synthesis of Peptides*, Oxford University Press, NY, NY (1991).

Larock, R., *Comprehensive Organic Transformations: A Guide to Functional Group Preparations*, VCH Publishers (Index) (1989).

Ocain, T.D., et al., "Synthesis of Sulfur–Containing Analogues of Bestatin, Inhibition of Aminopeptidases by α–Thiolbestatin Analogues," *J. Med. Chem.*, 31:2193–2199 (1988).

\* cited by examiner

EFFLUX PUMP INHIBITORS

RELATED APPLICATIONS

This application is a continuation-in-part of U.S. patent application Ser. No. 09/012,363, Chamberland et al., EFFLUX PUMP INHIBITORS, filed Jan. 23, 1998 is now U.S. Pat. No. 6,114,310, serial number not yet assigned, which is hereby incorporated by reference in its entirety.

FIELD OF THE INVENTION

This invention relates to the field of antimicrobial agents and to methods for identification and characterization of potential antimicrobial agents. More particularly, this invention relates to antimicrobial agents for which the mode of action involves cellular efflux pumps and the regulation of efflux pumps.

BACKGROUND

The following background material is not admitted to be prior art to the pending claims, but is provided only to aid the understanding of the reader.

Antibiotics have been effective tools in the treatment of infectious diseases during the last half century. From the development of antibiotic therapy to the late 1980s there was almost complete control over bacterial infections in developed countries. The emergence of resistant bacteria, especially during the late 1980s and early 1990s, is changing this situation. The increase in antibiotic resistant strains has been particularly common in major hospitals and care centers. The consequences of the increase in resistant strains include higher morbidity and mortality, longer patient hospitalization, and an increase in treatment costs. (B. Murray, 1994, *New Engl. J. Med.* 330: 1229–1230.)

The constant use of antibiotics in the hospital environment has selected bacterial populations that are resistant to many antibiotics. These populations include opportunistic pathogens that may not be strongly virulent but that are intrinsically resistant to a number of antibiotics. Such bacteria often infect debilitated or immunocompromised patients. The emerging resistant populations also include strains of bacterial species that are well known pathogens, which previously were susceptible to antibiotics. The newly acquired resistance is generally due to DNA mutations, or to resistance plasmids (R plasmids) or resistance-conferring transposons transferred from another organism. Infections by either type of bacterial population, naturally resistant opportunistic pathogens or antibiotic-resistant pathogenic bacteria, are difficult to treat with current antibiotics. New antibiotic molecules which can override the mechanisms of resistance are needed.

Bacteria have developed several different mechanisms to overcome the action of antibiotics. These mechanisms of resistance can be specific for a molecule or a family of antibiotics, or can be non-specific and be involved in resistance to unrelated antibiotics. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target (B. G. Spratt, *Science* 264:388 (1994)). There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics which would otherwise inhibit or kill the bacterial cells. Some bacteria utilize both mechanisms, combining a low permeability of the cell wall (including membranes) with an active efflux of antibiotics. (H. Nikaido, *Science* 264:382–388 (1994)).

In some cases, antibiotic resistance due to low permeability is related to the structure of the bacterial membranes. In general, bacteria can be divided into two major groups based on the structure of the membranes surrounding the cytoplasm. Gram-positive (G+) bacteria have one membrane, a cytoplasmic membrane. In contrast, Gram-negative (G−) bacteria have two membranes, a cytoplasmic membrane and an outer membrane. These bacterial membranes are lipid bilayers which contain proteins and may be associated with other molecules. The permeability of bacterial membranes affects susceptibility/resistance to antibiotics because, while there are a few molecular targets of antibiotics, e.g., penicillin-binding proteins, that are accessible from the outer leaflet of the cytoplasmic membranes, the principal targets for antibiotics are in the cytoplasm or in the inner leaflet of the cytoplasmic membrane. Therefore for an antibiotic which has a target in the cytoplasmic membrane, in Gram-negative bacteria that antibiotic will first need to cross the outer membrane. For a target in the cytoplasm, an antibiotic will need to cross the cytoplasmic membrane in Gram-positive bacteria, and both the outer and cytoplasmic membranes in Gram-negative bacteria. For both membranes, an antibiotic may diffuse through the membrane, or may cross using a membrane transport system.

For Gram-negative bacteria, the lipid composition of the outer membrane constitutes a significant permeability barrier. The outer layer of this outer membrane contains a lipid, lipopolysaccharide (LPS), which is only found in the outer membrane of Gram-negative bacteria. The lipid layer of the outer membrane is highly organized in a quasi-crystalline fashion and has a very low fluidity. Because of the low fluidity of the lipid layer of the outer membrane, even lipophilic antibiotics will not diffuse rapidly through the lipid layer. This has been shown experimentally, hydrophobic probe molecules have been shown to partition poorly into the hydrophobic portion of LPS and to permeate across the outer membrane bilayer at about one-fiftieth to one-hundredth the rate through the usual phospholipid bilayers (like the cytoplasmic membrane bilayer).

Some antibiotics may permeate through water-filled porin channels or through specific transport systems. Many of the porin channels, however, provide only narrow diameter channels which do not allow efficient diffusion of the larger antibiotic molecules. In addition, many porin channels are highly hydrophilic environments, and so do not efficiently allow the passage of hydrophobic molecules. Thus, the outer membrane acts as a molecular sieve for small molecules. This explains, in part, why Gram-negative bacteria are generally less susceptible to antibiotics than Gram-positive bacteria, and why Gram-negative bacteria are generally more resistant to large antibiotics, such as glycopeptides, that cannot cross the outer membrane.

The cytoplasmic membrane also provides a diffusion barrier for some antibiotics. However, since the fluidity of the lipid layer of the cytoplasmic membrane is higher than that of the outer membrane of Gram-negative bacteria, drugs that show some lipophilicity will be able to permeate through the lipid layer. Other drugs, such as phosphonomycin or D-cycloserine that have very low solubility in a lipophilic environment will cross the cytoplasmic membrane by using a transport system. In this case, though, if the transport system is not synthesized, the bacteria will become resistant to the drug (Peitz et al., 1967, *Biochem. J.* 6: 2561).

Decreasing the permeability of the outer membrane, by reducing either the number of porins or by reducing the number of a certain porin species, can decrease the susceptibility of a strain to a wide range of antibiotics due to the decreased rate of entry of the antibiotics into the cells. However, for most antibiotics, the half-equilibration times are sufficiently short that the antibiotic could exert its effect unless another mechanism is present. Efflux pumps are an example of such other mechanism. Once in the cytoplasm or periplasm a drug can be transported back to the outer medium. This transport is mediated by efflux pumps, which are constituted of proteins. Different pumps can efflux specifically a drug or group of drugs, such as the NorA system that transports quinolones, or Tet A that transports tetracyclines, or they can efflux a large variety of molecules, such as certain efflux pumps of *Pseudomonas aeruginosa*. In general, efflux pumps have a cytoplasmic component and energy is required to transport molecules out of the cell. Some efflux pumps have a second cytoplasmic membrane protein that extends into the periplasm. At least some efflux pumps of *P. aeruginosa* have a third protein located in the outer membrane.

Efflux pumps are involved in antibiotic resistance since, in some cases, they can remove a significant fraction of the antibiotic molecules which manage to enter the cells, thereby maintaining a very low intracellular antibiotic concentration. To illustrate, *P. aeruginosa* laboratory-derived mutant strain 799/61 which does not produce any measurable amounts of efflux pump is 8 to 10 fold more susceptible to tetracycline and ciprofloxacin than the parent strain *P. aeruginosa* 799, which synthesizes efflux pumps. Also, null mutants of mexA, the cytoplasmic component of a *P. aeruginosa* efflux pump, are more susceptible to antibiotics than the wild type.

The physiological role of efflux pumps has not been clearly defined yet. They are involved in drug resistance but they also are involved in the normal physiology of the bacterial cell. The efflux pump coded in the mexA operon of *P. aeruginosa* has been shown to be regulated by the iron content of the medium, and it is co-regulated with the synthesis of the receptors of siderophores. Siderophores are molecules that are needed for bacterial growth under iron starvation conditions, such as during infection of an animal. They are synthesized in the cytoplasm and exported when the bacterial cell needs iron. Siderophores scavenge iron within the infected animal and return the iron to the microbe to be used for essential microbial processes. Since there is essentially no free iron in the bodies of animals, including the human body, the production of siderophores by infecting bacteria is an important virulence factor for the progress of the infection.

Even organisms normally surrounded by a cell envelope of relatively high permeability can develop resistance by decreasing the permeability of the envelope. When an agent mainly diffuses across the barrier through a specific channel, mutational loss of the channel can be an efficient mechanism for resistance. A "nonclassical" β-lactam compound, imipenem, shows an exceptional activity against *P. aeruginosa*, mainly because this agent diffuses though a specific channel, OprD, whose physiological function appears to be that of the transport of basic amino acids. However, *P. aeruginosa* could become resistant to imipenem by simply losing the oprD channel, and currently a large fraction of *P. aeruginosa* strains isolated from the hospital environment are resistant as a result of this modification. In a similar manner, β-lactam compounds designed to mimic iron-chelating compounds (siderophores) during their transport through the outer membranes are known to select mutants that are defective in the specific transport of these siderophores.

In summary, the above discussion indicates that cellular factors affecting transport (both active and passive transport) of antibiotics into bacterial cells are important components of antibiotic resistance for many bacterial species.

SUMMARY

This invention concerns particular compounds which are efflux pump inhibitors, and which are therfore compounds which inhibit cellular efflux pumps of bacteria or other microbes. Such efflux pumps export substrate molecules from the cytoplasm in an energy-dependent manner, and the exported substrate molecules can include antibacterial agents or other antimicrobial agents. Such efflux pump inhibitors are useful, for example, for treating microbial infections by reducing the export of a co-administered antimicrobial agent or by preventing the export of a compound synthesized by microbes (e.g., bacteria) to allow or improve their growth. An example of reducing the export of such a compound is inhibiting iron availability for the microbe by reducing the export of siderophores. Thus, this invention also provides compositions which include such efflux pump inhibitors and methods for treating microbial infections using those compositions.

The identification and use of efflux pump inhibitors is described in U.S. patent applications, Trias et al., EFFLUX PUMP INHIBITORS, application Ser. No. 08/427,088, now U.S. Pat. No. 5,989,832 filed Apr. 21, 1995 and Trias et al., EFFLUX PUMP INHIBITORS, Appl. No. not yet assigned, filed Jul. 22, 1997, which are hereby incorporated by reference in their entireties including drawings. Screening methods described therein were used to identity some of the efflux inhibitor compounds of the present invention, and additional compounds were synthesized and tested which were structurally related to the active compounds identified through screening.

The efflux pump inhibitors of the present invention have structures which are shown by the generic structure 1 below:

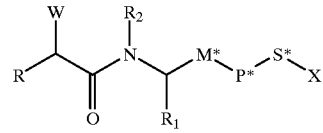

Structure 1 where $M^* = (CH_2)_n$ (n = 0–2)
$P^* = CH_2$, carbonyl (C = O), thiocarbonyl (C = S)
$S^* = NH, O, SO_t$ (t = 0–2);

R=H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_n NHC=(NR^a)NR^bR^c$, $(CH_2)_nSC=(NR^a)NR^bR^c$, $(CH_2)_n C=(NR^a)NR^bR^c$, $(CH_2)_nN=CNR^bR^c$(n=1–4); $R^a$ ($R^b$ or $R^c$)=H, lower alkyl, phenyl, substituted phenyl, benzyl, cyano, hydroxyl, or nitro. Alternatively $R^a+R^b$ (or $R^b$30 $R^c$)=$(CH_2)_{2\text{-}3}$ or —CH=CH—.

$R^1$=H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_n$ NHC=$(NR^a)NR^bR^c$, $(CH_2)_nSC$=$(NR^a)NR^bR^c$, $(CH_2)_n$ C=$(NR^a)NR^bR^c$, $(CH_2)_nN$=$CNR^bR^c$ (n=1–4); $R^a$ ($R^b$ or $R^c$)=H, lower alkyl, phenyl, benzyl, cyano, hydroxyl, or nitro. Alternatively $R^a+R^b$ (or $R^b+R^c$)=$(CH_2)_{2-3}$ or —CH=CH—.

$R^2$=H, lower alkyl, branched alkyl, fluoroalkyl, perfluoroalkyl, aryl, monosubstituted aryl, disubstituted aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_nNR^bR^c$, $(CH_2)_n$ NHC=$(NR^a)NR^bR^c$, $(CH_2)_nSC$=$(NR^a)NR^bR^c$, $(CH_2)_n$ C=$(NR^a)NR^bR^c$, $(CH_2)_nN$=$CNR^bR^c$ (n=1–4); $R^a$ ($R^b$ or $R^c$)=H, alkyl, phenyl, benzyl, cyano, hydroxyl, or nitro. Alternatively $R^a+R^b$ (or $R^b+R^c$)=$(CH_2)_{2-3}$ or —CH=CH—.

W=(alpha-aminoacyl)amido (such as glycylamido, D-alanylamido, D-aspartylamido, D-glutamylamido, D-leucylamido, D-phenylalanylamido, D-phenylglycylamido, D-tyrosylamido), aminoalkyl [$(CH_2)_n$ $NR^bR^c$; n=1–4; $R^b$ and/or $R^c$=H, lower alkyl, aryl], amino, azaheterocycles [such as N-morpholinyl, N-piperazinyl, N-pyrrolidinyl, N-imidazolyl, N-pyrrolyl, N-pyrazolyl, N-triazolyl, or N-tetrazolyl], substituted azaheterocycles [e.g., 2-(or 3-) lower alkylmorpholinyl, 2-(3- or 4-) lower alkylpiperazinyl, 2-(or 3-) lower alkylpyrrolidinyl, 2-(or 3-) lower alkylmorpholinyl, 2-(or 3-) lower alkylpyrrolyl], hydroxyl, alkoxy, alkylthio, guanidino, amidino, or halogen.

X=aryl, 2-(or 3-)thienyl, 2-(or 3-)furyl, or 2-(3- or 4-)pyridyl, tetrahydronaphthyl, indanyl, quinolinyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, quinoxalinylalkyl, quinazolinylalkyl, benzimidazolylalkyl, benzothiazolylalkyl, benzoxazolylalkyl.

Where there are centers of asymmetry, the absolute stereochemistry can be either R or S- configuration and any combination of configuration. Even racemic materials fulfill the structural generics descriptions.

In the generic descriptions of compounds of this invention, the number of atoms of a particular type in a substituent group is generally given as a range. For example, an alkyl group containing from 1 to 4 carbon atoms is indicated as alkyl ($C_1$–$C_4$), or as ($C_{1-4}$) alkyl. Such a range reference is intended to include specific references to groups having each of the integer number of atoms within the specified range. For example, $C_1$–$C_4$ includes each of $C_1$, $C_2$, $C_3$ and $C_4$. Other numbers of atoms and other types of atoms are indicated in a similar manner.

Unless otherwise indicated, the term "alkyl" refers to a branched or unbranched aliphatic hydrocarbon group, preferably having from 1 to 6 carbon atoms, and more preferably 1 to 4 carbon atoms. Preferably the hydrocarbon group is saturated. The alkyl group may optionally be substituted, and some preferred subsituents include alkoxy, alkylthio, halogen, amino, monosubstituted amino, disubstituted amino, and carboxy groups.

The term "lower alkyl" refers to an aliphatic hydrocarbon having 1 to 6 carbons, and preferably 1 to 4 carbon atoms (i.e., 1, 2, 3, or 4 carbon atoms). The lower alkyl group may be substituted; preferred substituents include alkoxy, alkylthio, halogen, amino, monosubstituted amino, disubstituted amino, and carboxy.

The term "branched alkyl" refers to a branched aliphatic hydrocarbon. The branched alkyl group is preferably 3 to 10 (i.e., 3, 4, 5, 6, 7, 8, 9 or 10 carbon atoms) carbons, and most preferably 3 to 6 carbons (i.e., 3, 4, 5, or 6 carbon atoms). The branched alkyl group may be substituted and some preferred substituents include alkoxy, alkylthio, halogen, amino, monosubstituted amino, disubstituted amino, and carboxy.

The term "fluoroalkyl" refers to a lower alkyl group which is substituted with a fluorine. The term "perfluoroalkyl" refers to a lower alkyl group which is substituted with a fluorine atom in every available position except for where the lower alkyl group is attached to the main chain.

The term "carboxyalkyl" refers to a chemical moiety with formula —(R)n—COOH, where R is an alkyl moiety, preferably a saturated alkyl, and where n is 0–5.

The term "hydroxyalkyl" refers to a chemical moiety with the formula —(R)n—OH, where R is an alkyl moiety and where n is 1–4.

The term "alkoxy" refers to a chemical substituent of formula —OR, where R is hydrogen or a saturated or unsaturated lower alkyl moiety.

The term "alkylthio" refers to a chemical substituent of formula —SR, where R is hydrogen or a saturated or unsaturated lower alkyl moiety.

The term "aryl" refers to an aromatic group which has at least one ring having a conjugated pi ($\pi$) electron system and includes both carbocyclic aryl (e.g. phenyl) and heterocyclic aryl groups (e.g. pyridine). The aryl group is preferably 6 to 14 carbons, more preferably 6 to 10 carbons. Aryl moieties include monocyclic, bicyclic, and tricyclic rings, where each ring has preferably five or six members. The aryl moiety may be optionally monosubstituted or disubstituted with lower alkyl, hydroxyl, alkoxy, alkylthio, halogen, amino, monosubstituted amino, and disubstituted amino.

The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon.

Thus, the term "azaheterocycle" refers to a heterocyclic group which includes at least one nitrogen atom in a ring. Preferably the azaheterocyclic group is a N-morpholinyl, N-thiomorpholinyl, N-piperazinyl, N-pyrrolidinyl, N-imidazolyl, N-pyrrolyl, N-pyrazolyl, N-triazolyl, and N-tetrazolyl group. The azaheterocyclic group may also be substituted as recognized in the art, forming a substituted azaheterocycle, preferably a 2-(or 3-) lower alkylmorpholinyl, 2-(3- or 4-)lower alkylthiomorpholinyl, 2-(3- or 4-) lower alkylpiperazinyl, 2-(or 3-) lower alkylpyrrolidinyl, 2-(or 3-) lower alkylmorpholinyl, 2-(or 3-) lower alkylpyrrolyl group.

The term "monosubstituted aryl" refers to an aryl group substituted with a group selected from alkyl, alkoxy, alkylthio, halogen, hydroxyl, amino, monosubstituted amino, or disubstituted amino.

"Halogen" or "halo" refers to F, Br, Cl, or I, but is preferably F or Br, and more preferably is F.

"Hydroxyl" or "hydroxy" refers to the group —OH.

The term "amino" means the group NRR', where R and R' may independently be alkyl or hydrogen or hydroxyl, but preferably are hydrogen. The term "monosubstituted amino" refers to an amino group in which one of R or R' is alkyl. The term "disubstituted amino" refers to an amino group in which R and R' are each independently alkyl or hydroxyl.

The term "arylalkyl" refers to a lower alkyl group substituted with an aryl group. An example of an arylalkyl group is benzyl where a methyl group is substituted with phenyl. The lower alkyl group may be optionally substituted with a lower alkyl, alkoxy, alkylthio, halogen, amino, monosubstituted amino, or disubstituted amino. The arylalkyl group may be aryl-substituted where the aryl group is optionally substituted with a lower alkyl, alkoxy, alkylthio, halogen, amino, monosubstituted amino, or disubstituted amino.

The term "thienylalkyl" refers to a lower alkyl group substituted with a thienyl group. The lower alkyl group may be optionally substituted with a lower alkyl, alkoxy, alkylthio, halogen, amino, monosubstituted amino, or disubstituted amino. The thienylalkyl group may be thienyl-substituted where the thienyl group is optionally substituted with a lower alkyl, alkoxy, alkylthio, halogen, amino, monosubstituted amino, or disubstituted amino.

The term "furylalkyl" refers to a lower alkyl group substituted with a furyl group. The lower alkyl group may be optionally substituted with a lower alkyl, alkoxy, alkylthio, halogen, amino, monosubstituted amino, or disubstituted amino. The furylalkyl group may be furyl-substituted where the furyl group is optionally substituted with a lower alkyl, alkoxy, alkylthio, halogen, amino, monosubstituted amino, or disubstituted amino.

The term "pyridylalkyl" refers to a lower alkyl group substituted with a pyridyl group. The lower alkyl group may be optionally substituted with a lower alkyl, alkoxy, alkylthio, halogen, amino, monosubstituted amino, or disubstituted amino. The pyridylalkyl group may be pyridyl-substituted where the pyridyl group is optionally substituted with a lower alkyl, alkoxy, alkylthio, halogen, amino, monosubstituted amino, or disubstituted amino.

The term "benzothienylalkyl" refers to a lower alkyl group substituted with a benzothienyl group. The lower alkyl group may be optionally substituted with a lower alkyl, alkoxy, alkylthio, halogen, amino, monosubstituted amino, or disubstituted amino. The benzothienylalkyl group may be benzothienyl-substituted where the benzothienyl group is optionally substituted with a lower alkyl, alkoxy, alkylthio, halogen, amino, monosubstituted amino, or disubstituted amino.

The term "indolyalkyl" refers to a lower alkyl group substituted with an indole group. The lower alkyl group may be optionally substituted with a lower alkyl, alkoxy, alkylthio, halogen, amino, monosubstituted amino, or disubstituted amino. The indolyalkyl group may be indole-substituted where the indole group is optionally substituted with a lower alkyl, alkoxy, alkylthio, halogen, amino, monosubstituted amino, or disubstituted amino.

The term "(alpha-aminoacyl)amido" refers to a group having an amide linkage and which is alpha-amino substituted. Preferably the group is an amide-linked alpha-amino acid, which may optionally be substituted, for example, glycylamido, D-alanylamido, D-aspartylamido, D-glutamylamido, D-leucylamido, D-phenylalanylamido, D-phenylglycylamido, D-tyrosylamido.

The term "aminoalkyl" refers to an amino substituted lower alkyl group, preferably $(CH_2)_n NR^b R^c$ where n=1–4; $R^b$ and/or $R^c$ is H, lower alkyl, aryl.

The term "quinolinylalkyl" refers to a lower alkyl group substituted with an quinolinyl group. The lower alkyl group may be optionally substituted with a lower alkyl, alkoxy, alkylthio, halogen, amino, monosubstituted amino, or disubstituted amino. The quinolinylalkyl group may be quinolinyl-substituted where the quinolinyl group is optionally substituted with a lower alkyl, alkoxy, alkylthio, halogen, amino, monosubstituted amino, or disubstituted amino.

The term "isoquinolinylalkyl" refers to a lower alkyl group substituted with an isoquinolinyl group. The lower alkyl group may be optionally substituted with a lower alkyl, alkoxy, alkylthio, halogen, amino, monosubstituted amino, or disubstituted amino. The isoquinolinylalkyl group may be isoquinolinyl-substituted where the quinolinyl group is optionally substituted with a lower alkyl, alkoxy, alkylthio, halogen, amino, monosubstituted amino, or disubstituted amino.

The term "quinoxalinylalkyl" refers to a lower alkyl group substituted with an quinoxalinyl group. The lower alkyl group may be optionally substituted with a lower alkyl, alkoxy, alkylthio, halogen, amino, monosubstituted amino, or disubstituted amino. The quinoxalinylalkyl group may be quinoxalinyl-substituted where the quinolinyl group is optionally substituted with a lower alkyl, alkoxy, alkylthio, halogen, amino, monosubstituted amino, or disubstituted amino.

The term "quinazolinylalkyl" refers to a lower alkyl group substituted with an quinazolinyl group. The lower alkyl group may be optionally substituted with a lower alkyl, alkoxy, alkylthio, halogen, amino, monosubstituted amino, or disubstituted amino. The quinazolinylalkyl group may be quinazolinyl-substituted where the quinazolinylgroup is optionally substituted with a lower alkyl, alkoxy, alkylthio, halogen, amino, monosubstituted amino, or disubstituted amino.

The term "benzimidazolylalkyl" refers to a lower alkyl group substituted with an benzimidazolyl group. The lower alkyl group may be optionally substituted with a lower alkyl, alkoxy, alkylthio, halogen, amino, monosubstituted amino, or disubstituted amino. The benzimidazolylalkyl group may be benzimidazolyl-substituted where the quinazolinylgroup is optionally substituted with a lower alkyl, alkoxy, alkylthio, halogen, amino, monosubstituted amino, or disubstituted amino.

The term "benzothiazolylalkyl" refers to a lower alkyl group substituted with an benzothiazolyl group. The lower alkyl group may be optionally substituted with a lower alkyl, alkoxy, alkylthio, halogen, amino, monosubstituted amino, or disubstituted amino. The benzothiazolylalkyl group may be benzothiazolyl-substituted where the quinazolinylgroup is optionally substituted with a lower alkyl, alkoxy, alkylthio, halogen, amino, monosubstituted amino, or disubstituted amino.

The term "benzoxazolylalkyl" refers to a lower alkyl group substituted with an benzoxazolyl group. The lower alkyl group may be optionally substituted with a lower alkyl, alkoxy, alkylthio, halogen, amino, monosubstituted amino, or disubstituted amino. The benzoxazolylalkyl group may be benzoxazolyl-substituted where the benzoxazolyl group is optionally substituted with a lower alkyl, alkoxy, alkylthio, halogen, amino, monosubstituted amino, or disubstituted amino.

The term "benzofuranyl" refers to a group which has the core ring structure of Structure A. The benzofuranyl group may be optionally substituted with lower alkyl, alkoxy, alkylthio, halogen, amino, monosubstituted amino, or disubstituted amino.

The term "benzothienyl" refers to a group which has the core ring structure of Structure B. The benzothienyl group may be optionally substituted with lower alkyl, alkoxy, alkylthio, halogen, amino, monosubstituted amino, or disubstituted amino.

The term "indolyl" refers to a group which has the core ring structure of Structure C. The indolyl group may be optionally substituted with lower alkyl, alkoxy, alkylthio, halogen, amino, monosubstituted amino, or disubstituted amino.

The term "benzimidazolyl" refers to a group which has the core ring structure of Structure D. The benzimidazolyl group may be optionally substituted with lower alkyl, alkoxy, alkylthio, halogen, amino, monosubstituted amino, or disubstituted amino.

The term "benzothiazolyl" refers to a group which has the core ring structure of Structure E. The benzothiazolyl group may be optionally substituted with lower alkyl, alkoxy, alkylthio, halogen, amino, monosubstituted amino, or disubstituted amino.

The term "benzoxazolyl" refers to a group which has the core ring structure of Structure F. The benzoxazolyl group may be optionally substituted with lower alkyl, alkoxy, alkylthio, halogen, amino, monosubstituted amino, or disubstituted amino.

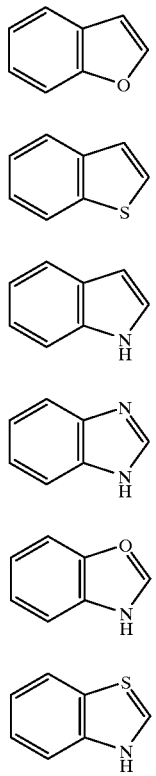

Structure A

Structure B

Structure C

Structure D

Structure F

Structure E

In preferred embodiments, certain efflux pump inhibitors of the present invention have structures which are shown by the generic structure 2 below:

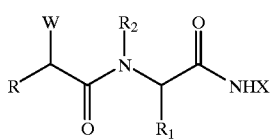

Structure 2 wherein
R=H, lower alkyl, branched alkyl, fluoroalkyl, perfluoroalkyl, carboxyalkyl, hydroxyalkyl, aryl, monosubstituted aryl, disubstituted aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^b R^c$, $(CH_2)_n NHC=(NR^a)NR^b R^c$, $(CH_2)_n SC=(NR^a)NR^b R^c$, $(CH_2)_n C=(NR^a)NR^b R^c$, $(CH_2)_n N=CNR^b R^c$ (n=1–4); $R^a$ ($R^b$ or $R^c$)=H, lower alkyl, phenyl, benzyl, cyano, hydroxy, or nitro. Alternatively $R^a+R^b$ (or $R^b+R^c$)=$(CH_2)_{2-3}$ or —CH=CH—;

$R^1$=H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^b R^c$, $(CH_2)_n NHC=(NR^a)NR^b R^c$, $(CH_2)_n SC=(NR^a)NR^b R^c$, $(CH_2)_n C=(NR^a)NR^b R^c$, $(CH_2)_n N=CNR^b R^c$ (n=1–4); $R^a$ ($R^b$ or $R^c$)=H, lower alkyl, phenyl, benzyl, cyano, hydroxy, or nitro. Alternatively $R^a+R^b$ (or $R^b+R^c$) =$(CH_2)_{2-3}$ or —CH=CH—;

$R^2$=H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_n NR^b R^c$, $(CH_2)_n NHC=(NR^a)NR^b R^c$, $(CH_2)_n SC=(NR^a)NR^b R^c$, $(CH_2)_n C=(NR^a)NR^b R^c$, $(CH_2)_n N=CNR^b R^c$ (n=1–4); $R^a$ ($R^b$ or $R^c$)=H, lower alkyl, phenyl, benzyl, cyano, hydroxy, or nitro. Alternatively $R^a+R^b$ (or $R^b+R^c$)=$(CH_2)_{2-3}$ or —CH=CH—;

W=(alpha-aminoacyl)amido (such as glycylamido, D-alanylamido, D-aspartylamido, D-glutamylamido, D-leucylamido, D-phenylalanylamido, D-phenylglycylamido, or D-tyrosyl-amido), aminoalkyl $[(CH_2)_n NR^b R^c$; n=1–4; $R^b$ and/or $R^c$=H, lower alkyl, aryl], amino, azaheterocycles (such as N-morpholinyl, N-piperazinyl, N-pyrrolidinyl, N-imidazolyl, N-pyrrolyl, N-pyrazolyl, N-triazolyl, or N-tetrazolyl), substituted azaheterocycles (such as 2-(or 3-) lower alkylmorpholinyl, 2-(3- or 4-) lower alkylpiperazinyl, 2-(or 3-) lower alkylpyrrolidinyl, 2-(or 3-) lower alkylmorpholinyl, 2-(or 3-) lower alkylpyrrolyl), hydroxy, alkoxy, alkylthio, guanidino, amidino, or halogen;

X=aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, isoquinolinyl, quinoxalinylalkyl, quinazolinylalkyl, benzimidazolylalkyl, benzothiazolylalkyl, benzoxazolylalkyl;

where there are centers of asymmetry, the absolute stereochemistry can be either R or S- configuration and any combination of configuration; even racemic materials fulfill the structural generics description.

In preferred embodiments, certain efflux pump inhibitors of the present invention have structures which are shown by the generic structure 3 below:

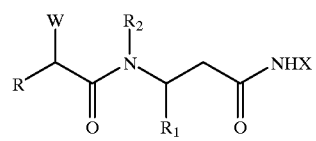

Structure 3 wherein
R=H, lower alkyl, branched alkyl, fluoroalkyl, perfluoroalkyl, carboxy-alkyl, hydroxyalkyl, aryl, monosubstituted aryl, disubstituted aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_n N=CNR^bR^c$ (n=1–4); $R^a$ ($R^b$ or $R^c$)=H, lower alkyl, phenyl, benzyl, cyano, hydroxy, or nitro. Alternatively $R^a+R^b$ (or $R^a+R^c$)=$(CH_2)_{2-3}$ or —CH=CH—

$R^1$=H, lower alkyl, branched alkyl, fluoroalkyl, perfluoroalkyl, carboxy-alkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_n N=CNR^bR^c$ (n=1–4); $R^a$ ($R^b$ or $R^c$)=H, lower alkyl, phenyl, benzyl, cyano, hydroxy, or nitro. Alternatively $R^a+R^b$ (or $R^b+R^c$)=$(CH_2)_{2-3}$ or —CH=CH—;

$R^2$=H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_nNR^bR^c$, $(CH_2)_nNHC=(NR^a)NR^bR^c$, $(CH_2)_n SC=(NR^a)NR^bR^c$, $(CH_2)_nC=(NR^a)NR^bR^c$, $(CH_2)_n N=CNR^bR^c$ (n=1–4); $R^a$ ($R^b$ or $R^c$)=H, lower alkyl, phenyl, benzyl, cyano, hydroxy, or nitro. Alternatively $R^a+R^b$ (or $R^b+R^c$)=$(CH_2)_{2-3}$ or —CH=CH—;

W=(alpha-aminoacyl)amido (such as glycylamido, D-alanylamido, D-aspartylamido, D-glutamylamido, D-leucylamido, D-phenylalanylamido, D-phenylglycylamido, or D-tyrosyl-amido), aminoalkyl $((CH_2)_nNR^bR^c$; n=1–4; $R^b$ and/or $R^c$=H, lower alkyl, aryl), amino, azaheterocycles (such as N-morpholinyl, N-piperazinyl, N-pyrrolidinyl, N-imidazolyl, N-pyrrolyl, N-pyrazolyl, N-triazolyl, or N-tetrazolyl), substituted azaheterocycles (such as 2-(or 3-) alkylmorpholinyl, 2-(3- or 4-) lower alkylpiperazinyl, 2-(or 3-) lower alkylpyrrolidinyl, 2-(or 3-) lower alkylmorpholinyl, 2-(or 3-) lower alkylpyrrolyl), hydroxy, alkoxy, alkylthio, guanidino, amidino, or halogen;

X=aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, isoquinolinyl, quinoxalinylalkyl, quinazolinylalkyl, benzimidazolylalkyl, benzothiazolylalkyl, benzoxazolylalkyl;

where there are centers of asymmetry, the absolute stereochemistry can be either R or S- configuration and any combination of configuration; even racemic materials fulilfill the structural generics description.

In preferred embodiments, certain efflux pump inhibitors of the present invention also have structures which are shown by the generic structure 4 below:

Structure 4

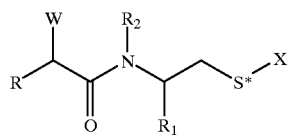

wherein
S*=NH, O, $SO_t$ (t=0–2);

R=H, lower alkyl, branched alkyl, fluoroalkyl, perfluoroalkyl, carboxyalkyl, hydroxyalkyl, aryl, monosubstituted aryl, disubstituted aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_n N=CNR^bR^c$ (n=1–4); $R^a$ ($R^b$ or $R^c$)=H, alkyl, phenyl, benzyl, cyano, hydroxy, or nitro. Alternatively $R^a+R^b$ (or $R^b+R^c$)=$(CH_2)_{2-3}$ or —CH=CH—

$R^1$=H, alkyl, branched alkyl, fluoroalkyl, perfluoroalkyl, carboxyalkyl, aryl,2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$ (n=1–4); $R^a$ ($R^b$ or $R^c$)=H, lower alkyl, phenyl, benzyl, cyano, hydroxy, or nitro. Alternatively $R^a+R^b$ (or $R^b+R^c$)=$(CH_2)_{2-3}$ or —CH=CH—;

$R^2$=H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_nNR^bR^c$, $(CH_2)_nNHC=(NR^a)NR^bR^c$, $(CH_2)_n SC=(NR^a)NR^bR^c$, $(CH_2)_nC=(NR^a)NR^bR^c$, $(CH_2)_n N=CNR^bR^c$ (n=1–4); $R^a$ ($R^b$ or $R^c$)=H, lower alkyl, phenyl, benzyl, cyano, hydroxy, or nitro. Alternatively $R^a+R^b$ (or $R^b+R^c$)=$(CH_2)_{2-3}$ or —CH=CH—;

W=(alpha-aminoacyl)amido (such as glycylamido, D-alanylamido, D-aspartylamido, D-glutamylamido, D-leucylamido, D-phenylalanylamido, D-phenylglycylamido, or D-tyrosyl-amido), aminoalkyl $((CH_2)_nNR^bR^c$; n=1–4; $R^b$ and/or $R^c$=H, lower alkyl, aryl), amino, azaheterocycles (such as N-morpholinyl, N-piperazinyl, N-pyrrolidinyl, N-imidazolyl, N-pyrrolyl, N-pyrazolyl, N-triazolyl, or N-tetrazolyl), substituted azaheterocycles (such as 2-(or 3-) alkylmorpholinyl, 2-(3- or 4-) lower alkylpiperazinyl, 2-(or 3-) lower alkylpyrrolidinyl, 2-(or 3-) lower alkylmorpholinyl, 2-(or 3-) lower alkylpyrrolyl], hydroxy, alkoxy, alkylthio, guanidino, amidino, or halogen;

X=aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, quinoxalinylalkyl, quinazolinylalkyl, benzimidazolylalkyl, benzothiazolylalkyl, benzoxazolylalkyl;

where there are centers of asymmetry, the absolute stereochemistry can be either R or S- configuration and any combination of configuration; even racemic materials fulfill the structural generics description.

In preferred embodiments of structure 2 compounds, the group $R^2$ is different from hydrogen.

The generic compound descriptions above should be understood to include additional narrower generic descriptions in which the possible substituents for one or more of the specified substituent groups or subsitutions (e.g., W, R, $R^1$, $R^2$, X, M*, P*, S*) is limited to a subset of the listed groups.

Compounds within the generic description above can be obtained by synthetic chemistry methods known to those skilled in the chemical arts as exemplified in the Examples below. Specific compound examples within the generic description are provided in the Detailed Description below in connection with Tables 1–4.

Reference to efflux pump inhibitors in the aspects of the invention described below refers to compounds within the generic compound descriptions above having efflux pump inhibitor activity.

A particularly appropriate example of a microbe appropriate for the use of an efflux pump inhibitor is a pathogenic bacterial species, *Pseudomonas aeruginosa*, which is intrinsically resistant to many of the commonly used antibacterial agents. Exposing this bacterium to an efflux pump inhibitor can significantly slow the export of an antibacterial agent from the interior of the cell or the export of siderophores. Therefore, if another antibacterial agent is administered in conjunction with the efflux pump inhibitor, the antibacterial agent, which would otherwise be maintained at a very low intracellular concentration by the export process, can accumulate to a concentration which will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species may contain similar broad substrate pumps, which actively export a variety of antimicrobial agents, and thus can also be appropriate targets.

In addition as suggested above, for some microbial, e.g., bacterial, species, efflux pump inhibitors can decrease the virulence of the microbe, for example, by inhibiting the transport of factors important for pathogenicity. Again using *P. aeruginosa* as an example, inhibition of an efflux pump in this bacterium inhibits the uptake of iron, which is important for pathogenicity. The mechanism of bacterial iron transport involves molecules called siderophores, which are synthesized and exported by bacterial cells via efflux pumps. These siderophores bind tightly to iron scavenged from the host, and are then taken up by the bacteria. In this way, the iron needed for bacterial metabolism is obtained, and an infection can be maintained.

Therefore, illustrating the utility of efflux pump inhibitors, inhibiting the efflux pump of *P. aeruginosa* allows obtaining one or more of the following biological effects:

1. *P. aeruginosa* strains will become susceptible to antibiotics that could not be used for treatment of pseudomonad infections, or become more susceptible to antibiotics which do inhibit pseudomonal growth.

2. *P. aeruginosa* strains will become more susceptible to antibiotics currently used for treatment of pseudomonad infections.

3. Virulence of *P. aeruginosa* will be attenuated because the availability of iron will be hampered.

4. The inhibition of the pump or of one of the components of the pump may be lethal or prevent growth.

Obtaining even one of these effects provides a potential therapeutic treatment for infections by this bacterium. Also, as previously mentioned, similar pumps are found in other microorganisms. Some or all of the above effects can also be obtained with those microbes, and they are therefore also appropriate targets for detecting or using efflux pump inhibitors. Thus, the term "microbes" include, for example, bacteria, fungi, yeasts, and protozoa.

As indicated, the bacterium to be inhibited through the use of an efflux pump inhibitor can be from other bacterial groups or species, such as one of the following:
*Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis,* Kingella, Moraxella, *Gardnerella vaginalis, Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus.*

The term "efflux pump" refers to a protein assembly which exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump which spans the outer membrane. Certain efflux pumps will include a polypeptide which has at least 50% amino acid sequence similarity with a polypeptide which is part of the *Pseudomonas aeruginosa* mexA/mexB/oprM efflux pump or the efflux pump overexpressed by *P. aeruginosa* Strain K385, or the efflux pump overexpressed by *P. aeruginosa* Strain PAO4098E. Due to the described sequence similarity of a component polypeptide of the efflux pump, such an efflux pump is termed a *Pseudomonas aeruginosa*-type efflux pump.

The term "non-tetracycline-specific efflux pump" refers to an efflux pump which is not highly specific for tetracycline (relative to other antibiotics) and thus is not a tetracycline (tetracycline-specific) efflux pump. The term thus includes broad substrate pumps (efflux a number of compounds with varying structural characteristics) and pumps which are highly specific for compounds (including antibiotics) other than tetracyclines. Tetracycline efflux pumps are involved in specific resistance to tetracycline in bacteria. (Speer et al., 1992, *Clin. Microbiol. Rev.* 5: 387–399.) As noted, these pumps are highly specific for tetracyclines, and their presence confers high tetracycline resistance to the cell. However, they do not confer resistance to other antibiotics. The genes for the tetracycline pump components are found in plasmids in Gram-negative as well as in Gram-positive bacteria and can be divided in two main groups, tetA(A-E), and tetK and tetL. TetA-E tetracycline resistance determinants contain a structural gene, tetA, which is a tetracycline specific pump, and a repressor gene, tetR, that mediates inducible resistance to tetracyclines. Tetracycline efflux pumps belonging to this group are designated tetA(A), tetA(B), tetA(D), and tetA(E), and are found in Enterobacteriaceae and other Gram-negative bacteria. TetK and TetL are pumps involved in tetracycline resistance in Gram-positive bacteria. The genes are regulated via translational attenuation and are not homologous to tetA group.

An "efflux pump inhibitor" is a compound which specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity. Of particular interest in this invention, are compounds which inhibit the export or activity of efflux pumps which have a broad substrate range which includes antibacterial agents. The term "non-tetracycline-specific efflux pump inhibitor" refers to an efflux pump inhibitor which inhibits a non-tetracycline-specific efflux pump. The term "*Pseudomonas aeruginosa*-type efflux pump inhibitor" refers to an efflux pump inhibitor which inhibits a *Pseudomonas aeruginosa*-type efflux pump. A "*Pseudomonas aeruginosa* efflux pump inhibitor" is an efflux pump inhibitor which inhibits the export activity of an efflux pump found in *Pseudomonas aeruginosa*.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In a first aspect, this invention provides a method for treating a microbial infection, e.g., a bacterial infection, in an animal by administering to an animal suffering from such an infection an efflux pump inhibitor as described above in an amount sufficient to reduce efflux pump activity.

In a preferred embodiment, the inhibitor is one which decreases the pathogenicity of the microbe. Such a decrease in pathogenicity can be obtained, for example, by interfering with bacterial iron acquisition by inhibiting the transport of siderophores. The pathogenicity may also be reduced by reducing or eliminating the microbial products which cause tissue-damaging effects to the host. Other methods of reducing pathogenicity are, however, also within this aspect. The animal may be, for example, chickens and turkeys, and in certain preferred embodiments is a mammal, e.g., a human.

In certain preferred embodiments, the microbial infection may be due to bacteria, which may, for example, be any of the bacterial species indicated above, but specifically including *Pseudomonas aeruginosa*.

In a related aspect, this invention provides a method of treating an animal suffering from a microbial infection by administering to the animal an efflux pump inhibitor as described above in an amount sufficient to reduce efflux pump activity. In this aspect, the efflux pump inhibitor in one which reduces the in vivo viability of a microbe involved in the infection. By reducing the in vivo viability, the infected animal can more readily clear its body of the infection, or the microbes may even be killed. In particular embodiments the animal is a mammal. Also in particular embodiments, the microbe may be from one of a variety of pathogenic bacterial species, specifically including those listed above.

The term "in vivo viability" refers to the ability of a microbe, e.g., a bacterium, to survive or grow in a host, such as an animal. Therefore, an efflux pump inhibitor which reduces the in vivo viability of a microbe may stop the growth of the microbe and/or kill the microbe. Such efflux pump inhibitors, therefore are antimicrobial agents.

In a further related aspect, this invention includes a method for prophylactic treatment of an animal, e.g., a mammal. In this method, an efflux pump inhibitor which reduces the pathogenicity of a microbe is administered to a mammal at risk of a microbial infection, e.g., a bacterial infection.

In a related aspect, the invention provides a method for treating a microbial infection in an animal, specifically including in a mammal, by treating an animal suffering from such an infection with an antimicrobial agent and an efflux pump inhibitor which increase the susceptibility of the microbe for that antimicrobial agent. In this way a microbe involved in the infection can be treated using the antimicrobial agent in smaller quantities, or can be treated with an antimicrobial agent which is not therapeutically effective when used in the absence of the efflux pump inhibitor. Thus, this method of treatment is especially appropriate for the treatment of infections involving microbial strains which are difficult to treat using an antimicrobial agent alone due to a need for high dosage levels (which can cause undesirable side effects), or due to lack of any clinically effective antimicrobial agents. However, it is also appropriate for treating infections involving microbes which are susceptible to particular antimicrobial agents as a way to reduce the dosage of those particular agents. This can reduce the risk of side effects, but can also reduce the selection effect for highly resistant microbes resulting from the consistent high level use of a particular antimicrobial agent.

In preferred embodiments the antimicrobial agent is a compound which is effluxed by efflux pumps in microbes involved in the infection.

In particular embodiments the microbe is a bacterium, which may, for example, be from any of the groups or species indicated above. Also in particular embodiments various antibacterial agents can be used. These include quinolones, tetracyclines, glycopeptides, aminoglycosides, β-lactams, rifamycins, coumermycins, macrolides, oxazolidinones, and chloramphenicol. In particular embodiments an antibiotic of the above classes can be, for example, one of the following:

β-Lactam Antibiotics
    imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefmetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763

Macrolides azithromycin, clarithromycin, erythromycin, oleandomycin, rokitamycin, rosaramicin, roxithromycin, troleandomycin Quinolones amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, PD131628, PD138312, PD140248, Q-35, AM-1 155,NM394, T-3761, rufloxacin, OPC-17116, DU-6859a (identified in Sato, K. et al., 1992, *Antimicrob Agents Chemother.* 37:1491–98), DV-7751a (identified in Tanaka, M. et al., 1992, *Antimicrob. Agents Chemother.* 37:2212–18)

Tetracyclines chlortetracycline, demeclocycline, doxycycline, lyniecycline, methacycline, minocycline, oxytetracycline, tetracycline Aminoglycosides amikacin, arbekacin, butirosin, dibekacin, fortimicins, gentamicin, kanamycin, meomycin, netilmicin, ribostamycin, sisomicin, spectinomycin, streptomycin, tobramycin, clindamycin, lincomycin Oxazolidinones Linezolid(U-100766), eperezolide(U-100592).

Each of the above compounds have been reported in the literature. Other antibiotic compounds which may be identified which are effluxed by particular bacteria can also be utilized with the efflux pump inhibitors of this invention.

In a further related aspect, this invention includes a method for prophylactic treatment of a mammal. In this method, an antimicrobial agent and an efflux pump inhibitor is administered to a mammal at risk of a microbial infection, e.g., a bacterial infection. Preferred embodiments include those as described above, for example, embodiments including various bacteria and antimicrobial agents as described.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

As used herein, the term "treating" refers to administering a pharmaceutical composition for prophylactic and/or therapeutic purposes. The term "prophylactic treatment" refers to treating a patient who is not yet infected, but who is susceptible to, or otherwise at risk of, a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of a potentiator and an antibacterial (or antimicrobial) agent in combination (either simultaneously or serially).

By "therapeutically effective amount" or "pharmaceutically effective amount" is meant an amount of an efflux pump inhibitor, or amounts individually of an efflux pump inhibitor and an antimicrobial agent, as disclosed for this invention, which have a therapeutic effect, which generally refers to the inhibition to some extent of the normal metabolism of microbial cells causing or contributing to a microbial infection. The doses of efflux pump inhibitor and antimicrobial agent which are useful in combination as a treatment are therapeutically effective amounts. Thus, as used herein, a therapeutically effective amount means those amounts of efflux pump inhibitor and antimicrobial agent which, when used in combination, produce the desired therapeutic effect as judged by clinical trial results and/or model animal infection studies. In particular embodiments, the efflux pump inhibitor and antimicrobial agent are combined in pre-determined proportions and thus a therapeutically effective amount would be an amount of the combination. This amount and the amount of the efflux pump inhibitor and antimicrobial agent individually can be routinely determined by one of skill in the art, and will vary, depending on several factors, such as the particular microbial strain involved and the particular efflux pump inhibitor and antimicrobial agent used. This amount can further depend upon the patient's height, weight, sex, age and medical history. For prophylactic treatments, a therapeutically effective amount is that amount which would be effective if a microbial infection existed.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

The term "microbial infection" refers to the invasion of the host mammal by pathogenic microbes. This includes the excessive growth of microbes which are normally present in or on the body of a mammal. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection.

The term "administration" or "administering" refers to a method of giving a dosage of an antimicrobial pharmaceutical composition to a mammal, where the method is, e.g., topical, oral, intravenous, intraperitoneal, or intramuscular. The preferred method of administration can vary depending on various factors, e.g., the components of the pharmaceutical composition, the site of the potential or actual bacterial infection, the microbe involved, and the severity of an actual microbial infection.

The term "mammal" is used in its usual biological sense. Thus, it specifically includes humans, cattle, horses, dogs, and cats, but also includes many other species.

In another aspect, this invention also features a method of inhibiting a membrane channel in a cellular membrane, involving contacting the membrane channel with a membrane channel inhibitor, where the inhibitor reduces the effluxing capacity of the membrane channel. In specific embodiments, at least one polypeptide of the membrane channel has at least 50% amino acid sequence similarity with a polypeptide of the mexA/mexB/oprM efflux pump, or of the efflux pump overexpressed by *Pseudomonas aeruginosa* Strain K385.

As used herein, the term "membrane channel" refers to a protein assembly located in the cellular membrane of a cell which allows the transport of one or more types of molecules across the membrane. Such transport may be either passive transport in response to concentration gradients, or may be active transport which depends upon a cellular energy source.

A "membrane channel inhibitor" then is, similar to an efflux pump inhibitor, a compound which slows or prevents the transport of molecules across the cellular membrane using the corresponding membrane channel.

This invention also features a method of enhancing the antimicrobial activity of an antimicrobial agent against a microbe, in which such a microbe is contacted with an efflux pump inhibitor, e.g., a non-tetracycline specific efflux pump inhibitor, to an efflux pump in the cell, and an antibacterial agent. The efflux pump inhibitor is a compound as described above. Thus, this method makes an antimicrobial agent more effective against a cell which expresses an efflux pump when the cell is treated with the combination of an antimicrobial agent and a non-tetracycline-specific efflux pump inhibitor. In particular embodiments the microbe is a bacterium or a fungus, such as any of those indicated above; the antimicrobial agent is as described above; and an antibacterial agent is selected from a number of structural classes of antibiotics including, e.g., β-lactams, glycopeptides, aminoglycosides, quinolones, tetracyclines, rifamycins, coumermycins, macrolides, oxazolidinones, and chloramphenicol. In particular embodiments an antibiotic of the above classes can be a compound as stated above.

In a further aspect this invention provides pharmaceutical compositions effective for treatment of an infection of an animal, e.g., a mammal, by a microbe, such as a bacterium or a fungus. The composition includes a pharmaceutically acceptable carrier and an efflux pump inhibitor as described above. In preferred embodiments, such compositions contain efflux pump inhibitors which are themselves effective antimicrobial agents, even in the absence of another antimicrobial agent (i.e., have intrinsic antimicrobial activity). Thus, pharmaceutical compositions including such efflux pump inhibitors can be used either alone or in conjunction with another antimicrobial agent. Also in preferred embodiments, the efflux pump inhibitors in pharmaceutical compositions of this aspect are efflux pump inhibitors which enhance the effectiveness of an antimicrobial agent other than the efflux pump inhibitor, so such compositions would generally be used in combination with such other antimicrobial agent.

The invention also provides pharmaceutical compositions similarly effective for treatment of an infection of a mammal which include an efflux pump inhibitor and an antimicrobial agent.

Similarly, the invention provides antimicrobial formulations which include an antimicrobial agent, an efflux pump inhibitor, and a carrier. In preferred embodiments, the antimicrobial agent is an antimicrobial agent or an antibacterial agent as described above.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the *Merck Index*, Merck & Company, Rahway, N.J. Considerations for the inclusion of various components in pharmaceutical compositions are described, e.g., in Gilman et al. (Eds.) (1990); *Goodman and Gilman's: The Pharmacological Basis of Therapeutics*, 8th Ed., Pergamon Press.

In yet another aspect, the invention provides a method of suppressing growth of a microbe, e.g., a bacterium, expressing an efflux pump, e.g., a non-tetracycline-specific efflux pump. As illustrated by the case where the microbe is a bacterium, the method involves contacting that bacterium with an efflux pump inhibitor, e.g., a non-tetracycline-specific efflux pump inhibitor, in the presence of a concentration of antibacterial agent below the MIC of the bacterium. This method is useful, for example, to prevent or cure contamination of a cell culture by a bacterium possessing an efflux pump. However, it applies to any situation where such growth suppression is desirable.

In a related aspect, the invention provides a method of suppressing growth of a microbe, e.g., a bacterium, which involves contacting the microbe with an efflux pump inhibitor which reduces the expression of a component of an efflux pump. Such an inhibitor can act on the regulation of that expression in number of different ways. It may, for example, enhance the production of a repressor molecule which prevents expression of an efflux pump component. Another possible mechanism is if the inhibitor blocks the release of a repressor molecule. Examples of such a repressor is MarR in *E. coli* (Seoane and Levy, 1994, *Abstr. of the Am. Soc. for Microbiol. Gen. Meeting*, Las Vegas, Nev., Abstr. H-26). An example of a positive regulator is BmrR in *Bacillus subtilis* (Ahmed et al., 1994, *J. Biol. Chem.*).

In another related aspect, the invention provides a method for reducing a population of a microbial, e.g., a bacterial strain, involving contacting the population with an efflux pump inhibitor which inhibits a component of an efflux pump expressed in the microbe in that population, which is essential for the growth of the microbe expressing that efflux pump. In particular embodiments, that component is a cytoplasmic membrane component. As indicated above, such efflux pump inhibitors may act in various ways, including, but not limited to, acting directly on the essential component, or acting to inhibit the expression of that component. In preferred embodiments of these aspects the microbe or bacterium is as described above.

The term "reducing a population" means that the microbes of that population are being killed. This is distinguished from the action of a static agent, e.g., a bacteriostatic agent, which prevents the bacteria from growing and multiplying but does not kill the microbes. Accordingly, in the context of this aspect, an "essential component" of an efflux pump is one which is essential to the in vivo survival of the microbe, i.e., the survival in a host.

In yet another aspect, this invention provides a method for enhancing growth of an animal by administering an efflux pump inhibitor to the animal, which inhibits an efflux pump expressed in a bacterial strain in the animal, and which inhibits the growth of that bacterial strain. Such a growth enhancing effect may result from the reduced energy consumption by the bacteria, which increases the food energy available to the animal. This method is appropriate, for example, for use with cattle, swine, and fowl such as chickens and turkeys.

In an additional aspect, the invention provides novel compounds having efflux pump activity. These compounds have chemical structures as described above.

Other features and advantages of the invention will be apparent from the following description of the preferred embodiments, and from the claims.

DESCRIPTION OF THE PREFERRED EMBODIMENTS

Identification of Efflux Pump Inhibitors

Initial identification of efflux pump inhibitors having structures as described for the present invention was performed using a screening method as generally described in Trias et al., EFFLUX PUMP INHIBITORS, U.S. application Ser. No. 08/427,088 and Trias et al., EFFLUX PUMP INHIBITORS, U.S. application Ser. No. 08/898,477, filed Jul. 22, 1997. In particular, the screening method based on inhibition of microbial growth in the presence of a subinhibitory concentration of an antibacterial agent which is normally effluxed by the test microbe and a concentration of a test compound was used for identifying some of the active compounds disclosed herein. In this method, inhibition of growth of the microbe is indicative that export of the antibacterial agent is inhibited by the test compound, and that the test compound is therefore an efflux pump inhibitor. The mode of action of the test compound so identified can then be confirmed as inhibiting active efflux. However, other screening methods for detecting efflux pump inhibitors can also be used, specifically including the additional methods described in the above references.

Synthesis of Derivatives of Efflux Pump Inhibitors from Screening

Exemplary compounds of the present invention were synthesized by methods as described in the Examples below. Those skilled in the art will understand how to synthesize additional compounds within the scope of this invention based on the described syntheses and/or the knowledge of those skilled in the art of chemical synthesis.

Susceptibility Testing

Particular exemplary efflux pump inhibitor compounds within the generic descriptions of the compounds of this invention were evaluated for potentiation effect. The in vitro microbiological data for antibiotic potentiation is presented in Tables 1–4 below. The compounds of Tables 1 and 2 correspond to Structure 2 compounds, compounds of Table 3 correspond to Structure 3 compounds, compounds of Table 4 to Structure 4 compounds.

Potentiation effect is observed by the reduction of the minimum inhibitory concentration of levofloxacin in the presence of the experimental efflux pump inhibitor. The activity of efflux pump inhibitors (EPI) in combination with fluoroquinolones, such as levofloxacin, is assessed by the checkerboard assay (Antimicrobial Combinations. In Antibiotics in Laboratory Medicine, Ed. Victor Lorian, M. D., Fourth edition, 1996, pp 333–338) using broth microdilution method performed as recommended by the NCCLS (National Committee for Clinical Laboratory Standards (NCCLS). 1997. Methods for Dilution of Antimicrobial Susceptibility Tests for Bacteria That Grow Aerobically— Fourth Edition; Approved Standard. NCCLS Document M7-A4, Vol 17 No.2). The test organism used is *Pseudomonas aeruginosa* PAM1001. The compounds of this invention demonstrate pump inhibitory activity against a broad-range of *P. aeruginosa* over-producing singular efflux pumps (MexAB, MexCD, and MexEF) and clinical strains containing multiple efflux pumps, not limited to the Mex classification. The compounds tabulated below are representative of the described invention.

In this assay, multiple dilutions of two drugs, namely the EPI and levofloxacin, are being tested, alone and in combination, at concentrations equal to, above and below their respective minimal inhibitory concentrations (MICs). In the case of EPI, most of these compounds are devoid of intrinsic antimicrobial activity and are tested at the maximum concentration of 40 µg/ml. The MIC of levofloxacin against *P. aeruginosa* PAM1001 is 4 µg/ml.

The EPI tested are readily soluble in water and stock solutions are prepared at a final concentration of 2 mg/ml. Stock solutions are further diluted, according to the needs of a particular assay, in Mueller Hinton Broth (MHB). Stock solution can be stored at −80° C. Quinolones are solubilized according to the instructions of the manufacturers, at a concentration of 1 mg/ml. They are then further diluted in MHB. Stock solution can be stored at −80° C.

The checkerboard assay is performed in microtiter plates. Levofloxacin is diluted in the x axis, each column containing a single concentration of levofloxacin. The EPI is diluted in the y axis, each row containing an equal concentration of EPI. The result of these manipulations is that each well of the microtiter plate contains a unique combination of concentrations of the two agents. Each EPI are tested independently.

The assay is performed in MHB with a final bacterial inoculum of $5 \times 10^5$ CFU/ml (from an early-log phase culture). Microtiter plates are incubated during 20 h at 35° C. and are read using a microtiterplate reader (Molecular Devices) at 650 nm as well as visual observation using a microtiterplate reading mirror. The MIC is defined as the lowest concentration of quinolone, within the combination, at which the visible growth of the organism is completely inhibited.

| Efflux Pump Inhibitors (EPIs) for Table 1 | |
|---|---|
| Comp | Structure |
| 1 | Phenylalanyl-ornithine quinoline-3-amide |
| 2 | Phenylalanyl-ornithine quinoline-8-amide |
| 3 | Phenylalanyl-ornithine 2-methylquinoline-8-amide |
| 4 | Alanyl-phenylalanyl-arginine 2-naphthylamide |
| 5 | D-Alanyl-phenylalanyl-arginine 2-naphthylamide |
| 6 | Valyl-phenylalanyl-arginine 2-naphthylamide |
| 7 | 4-Fluorophenylalanyl-ornithine quinoline-3-amide |
| 8 | 4-Fluorophenylalanyl-ornithine quinoline-8-amide |
| 9 | 4-Iodophenylalanyl-ornithine quinoline-3-amide |
| 10 | 4-Iodophenylalanyl-ornithine quinoline-8-amide |
| 11 | Homophenylalanyl-ornithine quinoline-3-amide |
| 12 | Homophenylalanyl-ornithine quinoline-8-amide |
| 13 | Homophenylalanyl-ornithine quinoline-6-amide |
| 14 | Homophenylalanyl-ornithine isoquinoline-5-amide |
| 15 | Phenylalanyl-$N_\alpha$-methylarginine 2-naphthylamide |
| 16 | Phenylalanyl-$N_\alpha$-methylornithine 2-naphthylamide |
| 17 | Phenylalanyl-$N_\alpha$-methylornithine 2-(naphthylmethyl)amide |
| 18 | Phenylalanyl-$N_\alpha$-methylornithine 2,2-diphenylethylamide |
| 19 | 4-Fluorophenylalanyl-$N_\alpha$-methylornithine 2-naphthylamide |
| 20 | 4-Iodophenylalanyl-$N_\alpha$-methylornithine 4-fluorophenethylamide |
| 21 | Tyrosyl-$N_\alpha$-methylornithine 2-naphthylamide |
| 22 | Homophenylalanyl-$N_\alpha$-methylornithine 4-fluorophenethylamide |
| 23 | Homophenylalanyl-$N_\alpha$-methylornithine 4-methylphenethylamide |
| 24 | Homophenylalanyl-$N_\alpha$-methylornithine 2,2-diphenylethylamide |
| 25 | Homophenylalanyl-$N_\alpha$-methylornithine 1,2,3,4-tetrahydronaphthyl-5-amide |
| 26 | Homophenylalanyl-$N_\alpha$-methylornithine 3-phenylpropylamide |
| 27 | Homophenylalanyl-$N_\alpha$-methylornithine 3-(4-methylphenyl)propylamide |
| 28 | Homophenylalanyl-$N_\alpha$-methylornithine 3-(4-methoxyphenyl)propylamide |
| 29 | Homophenylalanyl-$N_\alpha$-methylornithine 3-(4-fluorophenyl)propylamide |
| 30 | β-(2-Thiazolyl)alanyl-$N_\alpha$-methylornithine 2-naphthylamide |
| 31 | 4-(Dimethylaminoethoxy)phenylalanyl-$N_\alpha$-methylornithine 2-naphthylamide |

Efflux Pump Inhibitors (EPIs) for Table 1

| Comp | Structure |
|---|---|
| 32 | 4-(O-Methylcarboxyamido)phenylalanyl-$N_\alpha$-methylornithine 2-naphthylamide |
| 33 | β-(1-Naphthyl)alanyl-$N_\alpha$-methylornithine benzylamide |
| 34 | β-(2-Naphthyl)alanyl-$N_\alpha$-methylornithine benzylamide |
| 35 | β-(2-Naphthyl)alanyl-$N_\alpha$-methylornithine 4-hydroxyphenethylamide |
| 36 | Leucyl-$N_\alpha$-methylornithine 2-naphthylamide |
| 37 | β-(Cyclohexyl)alanyl-$N_\alpha$-methylornithine phenethylamide |
| 38 | Glycyl-$N_\alpha$-methylornithine 2-(cyclohexyl)ethylamide |
| 39 | Glycyl-$N_\alpha$-(phenethyl)ornithine 2-naphthylamide |
| 40 | Glycyl-$N_\alpha$-(phenethyl)ornithine 3-phenylpropylamide |
| 41 | Glycyl-$N_\alpha$-(phenethyl)ornithine quinoline-3-amide |
| 42 | Glycyl-$N_\alpha$-(phenethyl)ornithine 5-indanylamide |
| 43 | Glycyl-$N_\alpha$-(2-hydroxyphenethyl)ornithine 3-phenylpropylamide |
| 44 | Glycyl-$N_\alpha$-(3-phenylpropyl)ornithine 3-phenylpropylamide |
| 45 | Glycyl-$N_\alpha$-(isoamyl)ornithine 3-phenylpropylamide |
| 46 | Glycyl-$N_\alpha$-(2-benzoxazolylmethyl)ornithine 3-phenylpropylamide |
| 47 | Glycyl-$N_\alpha$-(3-quinolinylmethyl)ornithine 3-phenylpropylamide |
| 48 | β-Alanyl-$N_\alpha$-(phenethyl)ornithine 3-phenylpropylamide |
| 49 | Acetimidoylglycyl-$N_\alpha$-(phenethyl)ornithine 3-phenylpropylamide |
| 50 | Glycyl-$N_\alpha$-(phenethyl)lysine 3-phenylpropylamide |
| 51 | β-Alanyl-$N_\alpha$-(phenethyl)lysine 3-phenylpropylamide |
| 52 | 4-Aminobutyryl-$N_\alpha$-(phenethyl)diaminopropionic acid 3-phenylpropylamide |
| 53 | 4-Aminobutyryl-$N_\alpha$-(phenethyl)diaminopropionic acid quinoline-2-amide |
| 54 | Glycyl-$N_\alpha$-(phenethyl)diaminobutyric acid 3-phenylpropylamide |
| 55 | β-Alanyl-$N_\alpha$-(phenethyl)diaminobutyric acid 3-phenylpropylamide |
| 56 | 4-Aminobutyryl-$N_\alpha$-(phenethyl)diaminobutyric acid 3-phenylpropylamide |

Efflux Pump Inhibitors (EPIs) for Table 2

| Comp | Structure |
|---|---|
| 1 | D-Arginyl-D-phenylalanine quinoline-3-amide |
| 2 | D-Ornithyl-D-phenylalanine 2,2-diphenylethylamide |
| 3 | D-Ornithyl-D-phenylalanine 2-naphthylamide |
| 4 | Ornithyl-phenylalanine 1,2,3,4-tetrahydronaphthyl-5-amide |
| 5 | D-Ornithyl-D-phenylalanine 1,2,3,4-tetrahydronaphthyl-5-amide |
| 6 | Ornithyl-phenylalanine quinoline-3-amide |
| 7 | D-Ornithyl-D-phenylalanine quinoline-3-amide |
| 8 | Ornithyl-phenylalanine quinoline-8-amide |
| 9 | D-Ornithyl-D-phenylalanine quinoline-8-amide |
| 10 | D-Ornithyl-D-phenylalanine 3-phenylpropylamide |
| 11 | D-Ornithyl-D-4-methylphenylalanine 2-naphthylamide |
| 12 | D-Ornithyl-D-(N-methyl)phenylalanine 2-naphthylamide |
| 13 | D-Lysyl-D-phenylalanine 2-naphthylamide |
| 14 | D-Ornithyl-D-homophenylalanine quinoline-3-amide |
| 15 | D-Ornithyl-D-homophenylalanine 2-naphthylamide |
| 16 | D-Ornithyl-D-homophenylalanine quinoline-8-amide |
| 17 | D-Ornithyl-D-homophenylalanine 2,2-diphenylethylamide |
| 18 | D-Ornithyl-homophenylalanine quinoline-3-amide |
| 19 | Ornithyl-D-homophenylalanine quinoline-3-amide |
| 20 | D-Ornithyl-homophenylalanine quinoline-3-amide |
| 21 | D-Ornithyl-D-homophenylalanine quinoline-8-amide |
| 22 | D-Ornithyl-D-homophenylalanine (2-quinolinylmethyl)amide |
| 23 | D-Ornithyl-D-homophenylalanine (3-quinolinylmethyl)amide |
| 24 | D-Ornithyl-D-homophenylalanine 1-fluoronaphthyl-2-amide |
| 25 | D-Ornithyl-D-homophenylalanine 2-naphthylamide |
| 26 | D-Ornithyl-D-homophenylalanine 3-phenylpropylamide |
| 27 | D-Ornithyl-D-homophenylalanine 4-methylphenylamide |
| 28 | D-Ornithyl-D-homophenylalanine 4-fluorophenethylamide |
| 29 | D-Lysyl-D-homophenylalanine 2-naphthylamide |
| 30 | D-Ornithyl-D-β-(2-naphthyl)alanine benzylamide |
| 31 | D-Ornithyl-D-β-(1-naphthyl)alanine benzylamide |
| 32 | D-Ornithyl-D-β-(2-naphthyl)alanine 4-hydroxyphenethylamide |
| 33 | D-Ornithyl-D-β-(2-naphthyl)alanine iso-amylamide |
| 34 | D-Ornithyl-D-β-(2-naphthyl)alanine 2-hydroxybenzylamide |
| 35 | D-Ornithyl-D-β-(2-naphthyl)alanine phenethylamide |
| 36 | D-Ornithyl-D-β-(3-quinolinyl)alanine 3,3-dimethylbutylamide |
| 37 | D-Ornithyl-D-β-(3-quinolinyl)alanine 4-(t-butyl)phenylamide |
| 38 | D-Ornithyl-D-β-(3-quinolinyl)alanine 4-methylphenethylamide |
| 39 | D-Ornithyl-D-β-(3-quinolinyl)alanine 4-ethylbenzylamide |
| 40 | D-Ornithyl-D-β-(3-quinolinyl)alanine 3-phenylpropylamide |
| 41 | D-Ornithyl-D-β-(3-quinolinyl)alanine 2,3-trimethylenepyridyl-5-amide |
| 42 | D-$N_\alpha$-(C-Amidino)arginyl-D-β-(2-naphthyl)alanine benzylamide |
| 43 | D-Ornithyl-D-leucine 4-fluorophenethylamide |
| 44 | D-Ornithyl-D-leucine 3-phenylpropylamide |
| 45 | D-Ornithyl-D-valine 2-naphthylamide |
| 46 | D-Ornithyl-D-β-(t-butyl)alanine quinoline-3-amide |
| 47 | D-Diaminobutyryl-D-homophenylalanine quinoline-3-amide |
| 48 | D-Lysyl-D-β-(t-butyl)alanine quinoline-3-amide |
| 49 | D-Lysyl-D-homophenylalanine quinoline-3-amide |
| 50 | D-Lysyl-D-homophenylalanine (1-isoquinolinylmethyl)amide |
| 51 | D-Lysyl-D-homophenylalanine (2-quinolinylmethyl)amide |
| 52 | D-Lysyl-D-homophenylalanine (3-quinolinylmethyl)amide |
| 53 | D-Lysyl-D-β-(3-quinolinyl)alanine 4-ethylbenzylamide |

Efflux Pump Inhibitors (EPIs) for Table 3

| Comp | Structure |
|---|---|
| 1 | D-Ornithyl-N-(benzyl)glycine 2-naphthylamide |
| 2 | D-Ornithyl-N-(benzyl)glycine 3-phenylpropylamide |
| 3 | D-Ornithyl-N-(phenethyl)glycine 2-naphthylamide |
| 4 | D-Ornithyl-N-(phenethyl)glycine 3-phenylpropylamide |
| 5 | Ornithyl-N-(phenethyl)glycine 3-phenylpropylamide |
| 6 | D-Ornithyl-N-(phenylpropyl)glycine 3-phenylpropylamide |
| 7 | D-Ornithyl-β-(N-isopropyl)alanine 2-naphthylamide |
| 8 | D-Ornithyl-β-(N-isopropyl)alanine quinoline-3-amide |
| 9 | D-Ornithyl-β-(N-isoamyl)alanine 2-naphthylamide |
| 10 | D-Ornithyl-β-(N-isoamyl)alanine quinoline-3-amide |
| 11 | D-Ornithyl-β-(N-benzyl)alanine 2-naphthylamide |
| 12 | D-Ornithyl-β-(N-benzyl)alanine 3-phenylpropylamide |
| 13 | D-Ornithyl-β-(N-benzyl)alanine quinoline-3-amide |
| 14 | D-Ornithyl-β-(N-phenethyl)alanine quinoline-3-amide |
| 15 | D-Ornithyl-β-(N-phenethyl)alanine 2-naphthylamide |
| 16 | D-Ornithyl-β-(N-phenethyl)alanine 3-phenylpropylamide |
| 17 | D-Ornithyl-β-(N-cyclohexylmethyl)alanine 2-naphthylamide |
| 18 | D-Ornithyl-β-(N-cyclohexylmethyl)alanine quinoline-3-amide |
| 19 | D-Ornithyl-β-(N-cyclohexylmethyl)alanine 3-phenylpropylamide |
| 20 | D-Ornithyl-β-(N-phenylpropyl)alanine 2-naphthylamide |
| 21 | Ornithyl-β-(N-phenylpropyl)alanine 2-naphthylamide |
| 22 | D-Ornithyl-β-(N-phenylpropyl)alanine quinoline-3-amide |
| 23 | Ornithyl-β-(N-phenylpropyl)alanine quinoline-3-amide |
| 24 | Ornithyl-β-(N-phenylpropyl)alanine 3-phenylpropylamide |
| 25 | D-Ornithyl-β-(N-phenylpropyl)alanine (cyclohexylmethyl)amide |
| 26 | D-Ornithyl-β-[N-(4-methylphenyl)propyl]alanine 2-naphthylamide |
| 27 | D-Ornithyl-β-[N-(4-methylphenyl)propyl]alanine quinoline-3-amide |
| 28 | D-Ornithyl-β-(N-4-methoxyphenethyl)alanine 2-naphthylamide |
| 29 | D-Ornithyl-β-(N-4-methoxyphenethyl)alanine quinoline-3-amide |
| 30 | D-Ornithyl-β-(N-4-methylphenethyl)alanine 2-naphthylamide |
| 31 | D-Ornithyl-β-(N-4-methylphenethyl)alanine 1-fluoronaphthyl-2-amide |
| 32 | D-Ornithyl-β-(N-4-methylphenethyl)alanine quinoline-3-amide |
| 33 | D-Ornithyl-β-(N-4-fluorophenylpropyl)alanine 2-naphthylamide |
| 34 | D-Ornithyl-β-(N-4-fluorophenylpropyl)alanine quinolinyl-3-amide |
| 35 | D-Ornithyl-β-(N-cyclopropylmethyl)alanine 2-naphthylamide |
| 36 | D-Ornithyl-β-(N-cyclopropylmethyl)alanine quinolinyl-3-amide |
| 37 | D-Ornithyl-β-[N-(3,3-dimethylbutyl)]alanine 2-naphthylamide |
| 38 | D-Ornithyl-β-[N-(3,3-dimethylbutyl)]alanine quinolinyl-3-amide |
| 39 | D-Ornithyl-β-[N-(isobutyl)]alanine 2-naphthylamide |

Efflux Pump Inhibitors (EPIs) for Table 3

| Comp | Structure |
|---|---|
| 40 | D-Ornithyl-β-[N-(isobutyl)]alanine quinoline-3-amide |
| 41 | D-Ornithyl-β-[N-(3-ethoxypropyl)]alanine 2-naphthylamide |
| 42 | D-Ornithyl-β-[N-(ethylthioethyl)]alanine 2-naphthylamide |
| 43 | D-Ornithyl-β-[N-(ethylthioethyl)]alanine quinoline-3-amide |

Efflux Pump Inhibitors (EPIs) for Table 4

| Comp | Structure |
|---|---|
| 1 | Phenylalanyl-ornithinyl 2-naphthyl ether |
| 2 | Phenylalanyl-ornithinyl 2-naphthyl thioether |
| 3 | Homophenylalanyl-ornithinyl 2-naphthyl ether |
| 4 | Homophenylalanyl-ornithinyl 2-benzothiazole thioether |
| 5 | β-(2-Naphthyl)alanyl-ornithinyl 2-benzothiazole thioether |
| 6 | Homophenylalanyl-$N_\alpha$-methylornithinyl 2-naphthyl ether |
| 7 | Homophenylalanyl-$N_\alpha$-methylornithinyl 2-benzothiazole thioether |
| 8 | D-Phenylalanyl-$N_\alpha$-methylornithinyl 2-benzothiazole thioether |
| 10 | Phenylalanyl-$N_\alpha$-methylornithinyl 2-benzothiazole thioether |
| 11 | Homophenylalanyl-$N_\alpha$-methylargininyl 2-naphthyl ether |
| 12 | D-Ornithyl-D-phenylalaninyl 2-naphthyl ether |
| 13 | D-Lysyl-D-phenylalaninyl 2-naphthyl ether |
| 14 | Ornithyl-$N_\alpha$-methylphenylalaninyl 2-naphthyl ether |
| 15 | Ornithyl-phenylalaninyl 2-benzothiazole thioether |
| 16 | D-Ornithyl-D-phenylalaninyl 2-benzothiazole thioether |
| 17 | O-Benzylseryl-$N_\alpha$-methylornithinyl 2-naphthyl ether |
| 18 | N-(C-Amidino)homophenylalanyl-$N_\alpha$-methylargininyl 2-naphthyl ether |
| 19 | D-Ornithyl-D-phenylalaninyl 2-quinolinyl ether |
| 20 | D-Ornithyl-D-phenylalaninyl 8-quinolinyl ether |
| 21 | D-Lysyl-D-phenylalaninyl 2-benzothiazolyl thioether |
| 22 | D-Ornithyl-D-valinyl 2-naphthyl ether |
| 23 | D-Ornithyl-D-valinyl 2-quinolinyl ether |
| 24 | D-Ornithyl-D-phenylalaninyl 2-naphthyl thioether |
| 25 | D-Ornithyl-D-phenylalaninyl 3-quinolinyl thioether |
| 26 | D-Ornithyl-D-leucinyl 2-naphthyl thioether |
| 27 | D-Ornithyl-D-leuciny 2-quinolinyl thioether |
| 28 | D-Lysyl-D-phenylalaninyl 3-quinolinyl thioether |
| 29 | D-Lysyl-D-phenylalaninyl 2-naphthyl thioether |
| 30 | N-Ornithyl-N-benzylaminoethyl 2-naphthyl ethe |
| 31 | D-Ornithyl-N-benzylaminoethanol 2-naphthyl ether |
| 32 | Tyrosyl-$N_\alpha$-methylornithinyl 2-naphthyl ether |
| 33 | Homophenylalanyl-N-(3-aminopropyl)aminoethyl 2-naphthyl ether |
| 34 | D-Ornithyl-N-(phenethyl)aminoethanol 2-naphthyl ether |
| 35 | Ornithyl-N-(phenethyl)aminoethyl 2-naphthyl ether |
| 36 | β-(Cyclohexyl)alanine N-(3-aminopropyl)-3-(cyclohexyl)propylamide |
| 37 | D-Ornithyl-N-(phenethyl)aminopropyl 2-quinolinyl ether |
| 38 | D-Ornithyl-N-(benzyl)aminopropyl 2-quinolinyl ether |
| 39 | D-Ornithyl-N-(phenethyl)aminoethyl 3-phenylpropyl thioether |
| 40 | D-Ornithine N-(isoamylaminoethyl)phenylpropylamide |
| 41 | D-Ornithyl-D-phenylalaninyl benzyl thioether |
| 42 | Homophenylalanyl-ornithinyl 2-phenethyl thioether |
| 43 | Homophenylalanine N-(3-aminopropyl)-3-phenylpropylamide |
| 44 | D-Ornithyl-N-(phenethyl)aminoethyl benzyl thioether |
| 45 | D-Ornithyl-N-(phenethyl)aminoethyl (4-ethylbenzyl) thioether |

TABLE 1

Levofloxacin MIC Against *P. aeruginosa* PAM1001 in Presence of Efflux Pump Inhibitor (EPI)

Minimum Inhibitory Concentration (μg/ml)

| Compound | EPI Conc. 0 μg/ml | EPI Conc. 0.625 μg/ml | EPI Conc. 1.25 μg/ml | EPI Conc. 2.5 μg/ml | EPI Conc. 5 μg/ml | EPI Conc. 10 μg/ml | EPI Conc. 20 μg/ml | EPI Conc. 40 μg/ml |
|---|---|---|---|---|---|---|---|---|
| 1 | 4 | 4 | 4 | 4 | 4 | 2 | 0.50 | 0.06 |
| 2 | 4 | 4 | 4 | 4 | 4 | 1 | 0.50 | 0.06 |
| 3 | 4 | 4 | 4 | 4 | 4 | 2 | 1 | 0.50 |
| 4 | 4 | 4 | 4 | 4 | 4 | 0.06 | 0.03 | 0.03 |
| 5 | 4 | 4 | 4 | 4 | 4 | 0.25 | 0.03 | 0.03 |
| 6 | 4 | 4 | 4 | 4 | 4 | 2 | 0.015 | 0.008 |
| 7 | 4 | 4 | 4 | 4 | 2 | 1 | 0.50 | 0.06 |
| 8 | 4 | 4 | 4 | 4 | 2 | 1 | 0.50 | 0.25 |
| 9 | 4 | 4 | 4 | 1 | 0.06 | 0.06 | 0.06 | 0.06 |
| 10 | 4 | 4 | 4 | 2 | 0.50 | 0.25 | 0.25 | 0.125 |
| 11 | 4 | 4 | 4 | 2 | 1 | 0.06 | 0.03 | 0.03 |
| 12 | 4 | 4 | 4 | 2 | 0.50 | 0.125 | 0.125 | 0.125 |
| 13 | 4 | 4 | 4 | 4 | 2 | 1 | 0.50 | 0.06 |
| 14 | 4 | 4 | 4 | 4 | 4 | 2 | 1 | 0.25 |
| 15 | 4 | 4 | 4 | 4 | 1 | 0.06 | 0.03 | 0.015 |
| 16 | 4 | 4 | 4 | 4 | 0.50 | 0.03 | 0.015 | 0.015 |
| 17 | 4 | 4 | 4 | 4 | 4 | 1 | 0.06 | 0.03 |
| 18 | 4 | 4 | 4 | 4 | 4 | 2 | 0.50 | 0.25 |
| 19 | 4 | 4 | 4 | 4 | 0.06 | 0.06 | 0.03 | 0.015 |
| 20 | 4 | 4 | 4 | 2 | 0.06 | 0.03 | 0.03 | 0.03 |
| 21 | 4 | 4 | 2 | 1 | 0.25 | 0.125 | 0.03 | 0.008 |
| 22 | 4 | 4 | 4 | 4 | 2 | 1 | 0.125 | 0.125 |
| 23 | 4 | 4 | 4 | 2 | 0.25 | 0.25 | 0.25 | 0.25 |
| 24 | 4 | 4 | 4 | 4 | 4 | 1 | 0.06 | 0.008 |
| 25 | 4 | 4 | 4 | 4 | 4 | 1 | 0.06 | 0.06 |
| 26 | 4 | 4 | 4 | 4 | 2 | 1 | 0.125 | 0.06 |

TABLE 1-continued

Levofloxacin MIC Against *P. aeruginosa* PAM1001 in Presence of Efflux Pump Inhibitor (EPI)

Minimum Inhibitory Concentration (μg/ml)

| Compound | EPI Conc. 0 μg/ml | EPI Conc. 0.625 μg/ml | EPI Conc. 1.25 μg/ml | EPI Conc. 2.5 μg/ml | EPI Conc. 5 μg/ml | EPI Conc. 10 μg/ml | EPI Conc. 20 μg/ml | EPI Conc. 40 μg/ml |
|---|---|---|---|---|---|---|---|---|
| 27 | 4 | 4 | 4 | 1 | 0.125 | 0.125 | 0.125 | 0.06 |
| 28 | 4 | 4 | 4 | 4 | 2 | 1 | 0.06 | 0.125 |
| 29 | 4 | 4 | 4 | 2 | 1 | 0.125 | 0.125 | 0.125 |
| 30 | 4 | 4 | 4 | 4 | 4 | 2 | 0.50 | 0.03 |
| 31 | 4 | 4 | 4 | 2 | 1 | 1 | 0.50 | 0.25 |
| 32 | 4 | 4 | 4 | 4 | 2 | 1 | 0.50 | 0.06 |
| 33 | 4 | 4 | 4 | 4 | 4 | 2 | 1 | 0.50 |
| 34 | 4 | 4 | 4 | 4 | 4 | 2 | 0.125 | 0.125 |
| 35 | 4 | 4 | 4 | 4 | 2 | 1 | 0.50 | 0.125 |
| 36 | 4 | 4 | 2 | 2 | 0.125 | 0.06 | 0.015 | 0.015 |
| 37 | 4 | 4 | 4 | 4 | 1 | 0.25 | 0.125 | 0.125 |
| 38 | 4 | 4 | 4 | 4 | 4 | 2 | 0.50 | 0.50 |
| 39 | 4 | 2 | 0.50 | 0.06 | 0.03 | 0.03 | 0.03 | 0.03 |
| 40 | 4 | 4 | 1 | 0.50 | 0.25 | 0.125 | 0.06 | 0.125 |
| 41 | 4 | 4 | 4 | 1 | 1 | 0.25 | 0.25 | 0.25 |
| 42 | 4 | 2 | 1 | 0.03 | 0.015 | 0.015 | 0.015 | 0.015 |
| 43 | 4 | 4 | 4 | 2 | 1 | 0.25 | 0.25 | 1 |
| 44 | 4 | 4 | 2 | 1 | 0.50 | 0.25 | 0.25 | 0.25 |
| 45 | 4 | 4 | 4 | 2 | 1 | 0.50 | 0.50 | 0.125 |
| 46 | 4 | 4 | 4 | 1 | 0.25 | 0.125 | 0.125 | 0.250 |
| 47 | 4 | 4 | 4 | 2 | 1 | 0.25 | 0.25 | 0.125 |
| 48 | 4 | 4 | 4 | 1 | 1 | 0.25 | 0.25 | 0.25 |
| 49 | 4 | 4 | 4 | 4 | 2 | 1 | 0.25 | 0.25 |
| 50 | 4 | 4 | 4 | 1 | 0.50 | 0.125 | 0.06 | 0.06 |
| 51 | 4 | 4 | 4 | 2 | 1 | 0.125 | 0.125 | 0.125 |
| 52 | 4 | 4 | 4 | 4 | 1 | 0.50 | 0.125 | 0.125 |
| 53 | 4 | 4 | 4 | 4 | 1 | 0.25 | 0.06 | 0.03 |
| 54 | 4 | 2 | 2 | 1 | 0.25 | 0.25 | 0.06 | 0.06 |
| 55 | 4 | 4 | 2 | 2 | 0.50 | 0.25 | 0.125 | 0.125 |
| 56 | 4 | 4 | 4 | 2 | 0.50 | 0.25 | 0.25 | 0.06 |

TABLE 2

Levofloxacin MIC Against *P. aeruginosa* PAM1001 in Presence of Efflux Pump Inhibitor (EPI)

Minimum Inhibitory Concentration (μg/ml)

| Compound | EPI Conc. 0 μg/ml | EPI Conc. 0.625 μg/ml | EPI Conc. 1.25 μg/ml | EPI Conc. 2.5 μg/ml | EPI Conc. 5 μg/ml | EPI Conc. 10 μg/ml | EPI Conc. 20 μg/ml | EPI Conc. 40 μg/ml |
|---|---|---|---|---|---|---|---|---|
| 1 | 4 | 4 | 4 | 4 | 2 | 0.06 | 0.015 | 0.015 |
| 2 | 4 | 4 | 4 | 4 | 4 | 4 | 1 | 0.25 |
| 3 | 4 | 4 | 4 | 4 | 1 | 1 | 0.06 | 0.03 |
| 4 | 4 | 4 | 4 | 4 | 4 | 2 | 0.50 | 0.125 |
| 5 | 4 | 4 | 4 | 4 | 4 | 1 | 0.25 | 0.125 |
| 6 | 4 | 4 | 4 | 4 | 2 | 2 | 0.50 | 0.125 |
| 7 | 4 | 4 | 4 | 4 | 4 | 4 | 0.50 | 0.125 |
| 8 | 4 | 4 | 4 | 4 | 2 | 2 | 0.50 | 0.06 |
| 9 | 4 | 4 | 4 | 4 | 4 | 2 | 1 | 0.06 |
| 10 | 4 | 4 | 4 | 4 | 4 | 2 | 0.25 | 0.25 |
| 11 | 4 | 4 | 4 | 2 | 0.125 | 0.06 | 0.03 | NA |
| 12 | 4 | 4 | 4 | 4 | 2 | 0.50 | 0.06 | 0.03 |
| 13 | 4 | 4 | 4 | 4 | 2 | 1 | 0.125 | 0.06 |
| 14 | 4 | 4 | 4 | 4 | 2 | 1 | 0.50 | 0.03 |
| 15 | 4 | 4 | 4 | 2 | 1 | 0.06 | 0.06 | 0.06 |
| 16 | 4 | 4 | 4 | 4 | 2 | 1 | 0.125 | 0.03 |
| 17 | 4 | 4 | 4 | 4 | 2 | 0.50 | 0.25 | 0.03 |
| 18 | 4 | 4 | 4 | 4 | 4 | 2 | 0.125 | 0.125 |
| 19 | 4 | 4 | 4 | 4 | 4 | 0.50 | 0.06 | 0.015 |
| 20 | 4 | 4 | 4 | 2 | 1 | 0.125 | 0.03 | 0.015 |
| 21 | 4 | 4 | 4 | 4 | 2 | 0.50 | 0.03 | 0.008 |
| 22 | 4 | 4 | 4 | 4 | 1 | 0.25 | 0.06 | 0.03 |
| 23 | 4 | 4 | 4 | 4 | 2 | 0.50 | 0.50 | 0.06 |
| 24 | 4 | 4 | 4 | 2 | 0.25 | 0.03 | 0.03 | 0.06 |
| 25 | 4 | 4 | 4 | 2 | 1 | 0.06 | 0.06 | 0.06 |
| 26 | 4 | 4 | 4 | 4 | 2 | 0.125 | 0.125 | 0.06 |
| 27 | 4 | 4 | 4 | 2 | 2 | 2 | 2 | 2 |
| 28 | 4 | 4 | 4 | 4 | 1 | 0.50 | 0.25 | 0.125 |
| 29 | 4 | 4 | 4 | 2 | 0.125 | 0.06 | 0.06 | 0.06 |

TABLE 2-continued

Levofloxacin MIC Against *P. aeruginosa* PAM1001 in Presence of Efflux Pump Inhibitor (EPI)

| | Minimum Inhibitory Concentration (µg/ml) | | | | | | | |
|---|---|---|---|---|---|---|---|---|
| Compound | EPI Conc. 0 µg/ml | EPI Conc. 0.625 µg/ml | EPI Conc. 1.25 µg/ml | EPI Conc. 2.5 µg/ml | EPI Conc. 5 µg/ml | EPI Conc. 10 µg/ml | EPI Conc. 20 µg/ml | EPI Conc. 40 µg/ml |
| 30 | 4 | 4 | 4 | 0.50 | 0.25 | 0.03 | 0.03 | 0.03 |
| 31 | 4 | 4 | 4 | 4 | 2 | 0.125 | 0.03 | 0.03 |
| 32 | 4 | 4 | 4 | 4 | 2 | 0.50 | 0.125 | 0.06 |
| 33 | 4 | 4 | 4 | 2 | 0.25 | 0.06 | 0.06 | 0.06 |
| 34 | 4 | 4 | 4 | 2 | 0.50 | 0.25 | 0.06 | 0.50 |
| 35 | 4 | 4 | 4 | 4 | 2 | 0.25 | 0.125 | 0.06 |
| 36 | 4 | 4 | 4 | 4 | 2 | 1 | 0.25 | 0.50 |
| 37 | 4 | 4 | 4 | 4 | 2 | 0.008 | 0.015 | 0.008 |
| 38 | 4 | 4 | 4 | 4 | 4 | 1 | 0.125 | 0.03 |
| 39 | 4 | 4 | 4 | 4 | 2 | 0.25 | 0.03 | 0.25 |
| 40 | 4 | 4 | 4 | 4 | 4 | 2 | 0.50 | 0.03 |
| 41 | 4 | 4 | 4 | 2 | 4 | 0.015 | 0.015 | 0.03 |
| 42 | 4 | 2 | 2 | 0.50 | 0.125 | 0.25 | 0.25 | 0.25 |
| 43 | 4 | 4 | 4 | 4 | 4 | 2 | 2 | 0.50 |
| 44 | 4 | 4 | 4 | 4 | 4 | 1 | 0.50 | 0.25 |
| 45 | 4 | 4 | 4 | 4 | 4 | 2 | 1 | 0.50 |
| 46 | 4 | 4 | 4 | 4 | 2 | 1 | 0.50 | 0.25 |
| 47 | 4 | 4 | 4 | 4 | 2 | 1 | 0.125 | 0.03 |
| 48 | 4 | 4 | 4 | 4 | 2 | 1 | 0.50 | 0.25 |
| 49 | 4 | 4 | 2 | 2 | 0.50 | 0.06 | 0.03 | 0.03 |
| 50 | 4 | 4 | 4 | 4 | 2 | 0.50 | 0.25 | 0.03 |
| 51 | 4 | 4 | 4 | 4 | 4 | 1 | 0.50 | 0.06 |
| 52 | 4 | 4 | 4 | 4 | 2 | 1 | 0.25 | 0.03 |
| 53 | 4 | 4 | 4 | 4 | 4 | 0.06 | 0.015 | 0.06 |

TABLE 3

Levofloxacin MIC Against *P. aeruginosa* PAM1001 in Presence of Efflux Pump Inhibitor (EPI)

| | Minimum Inhibitory Concentration (µg/ml) | | | | | | | |
|---|---|---|---|---|---|---|---|---|
| Compound | EPI Conc. 0 µg/ml | EPI Conc. 0.625 µg/ml | EPI Conc. 1.25 µg/ml | EPI Conc. 2.5 µg/ml | EPI Conc. 5 µg/ml | EPI Conc. 10 µg/ml | EPI Conc. 20 µg/ml | EPI Conc. 40 µg/ml |
| 1 | 4 | 4 | 4 | 4 | 4 | 1 | 0.25 | 0.06 |
| 2 | 4 | 4 | 4 | 4 | 4 | 2 | 1 | 0.125 |
| 3 | 4 | 4 | 4 | 4 | 2 | 1 | 0.25 | 0.03 |
| 4 | 4 | 4 | 4 | 4 | 2 | 0.25 | 0.125 | 0.125 |
| 5 | 4 | 4 | 4 | 4 | 2 | 1 | 0.25 | 0.125 |
| 6 | 4 | 4 | 4 | 2 | 1 | 0.06 | 0.06 | 0.06 |
| 7 | 4 | 4 | 4 | 4 | 2 | 0.50 | 0.25 | 0.06 |
| 8 | 4 | 4 | 4 | 4 | 4 | 2 | 2 | 0.50 |
| 9 | 4 | 4 | 4 | 2 | 0.125 | 0.06 | 0.06 | 0.06 |
| 10 | 4 | 4 | 4 | 4 | 2 | 0.50 | 0.125 | 0.03 |
| 11 | 4 | 4 | 4 | 1 | 0.25 | 0.06 | 0.008 | 0.008 |
| 12 | 4 | 4 | 4 | 4 | 2 | 1 | 0.50 | 0.125 |
| 13 | 4 | 4 | 4 | 2 | 1 | 0.50 | 0.25 | 0.015 |
| 14 | 4 | 4 | 4 | 4 | 2 | 0.50 | 0.03 | 0.015 |
| 15 | 4 | 4 | 4 | 2 | 0.06 | 0.015 | 0.015 | 0.015 |
| 16 | 4 | 4 | 4 | 4 | 4 | 2 | 0.50 | 0.06 |
| 17 | 4 | 4 | 2 | 2 | 0.25 | 0.06 | 0.06 | 0.06 |
| 18 | 4 | 4 | 4 | 2 | 1 | 0.50 | 0.03 | 0.03 |
| 19 | 4 | 4 | 4 | 4 | 2 | 0.50 | 0.125 | 0.125 |
| 20 | 4 | 4 | 2 | 1 | 0.03 | 0.03 | 0.03 | 0.03 |
| 21 | 4 | 4 | 2 | 1 | 0.03 | 0.03 | 0.06 | 0.03 |
| 22 | 4 | 4 | 4 | 2 | 1 | 0.125 | 0.03 | 0.06 |
| 23 | 4 | 4 | 4 | 2 | 0.25 | 0.06 | 0.03 | 0.015 |
| 24 | 4 | 4 | 4 | 4 | 2 | 0.25 | 0.125 | 0.125 |
| 25 | 4 | 4 | 4 | 4 | 2 | 1 | 0.50 | 0.25 |
| 26 | 4 | 4 | 4 | 2 | 0.06 | 0.015 | 0.03 | NA |
| 27 | 4 | 4 | 4 | 1 | 0.06 | 0.03 | 0.03 | 0.03 |
| 28 | 4 | 4 | 4 | 2 | 0.015 | 0.008 | 0.015 | 0.015 |
| 29 | 4 | 4 | 4 | 4 | 2 | 0.25 | 0.03 | 0.008 |
| 30 | 4 | 4 | 4 | 2 | 0.25 | 0.015 | 0.015 | 0.015 |
| 31 | 4 | 4 | 2 | 0.125 | 0.03 | 0.03 | 0.06 | NA |
| 32 | 4 | 4 | 2 | 2 | 0.125 | 0.008 | 0.008 | 0.015 |
| 33 | 4 | 4 | 2 | 0.06 | 0.015 | 0.015 | 0.03 | NA |
| 34 | 4 | 4 | 4 | 2 | 1 | 0.25 | 0.015 | 0.03 |
| 35 | 4 | 4 | 4 | 4 | 2 | 1 | 0.25 | 0.06 |

TABLE 3-continued

Levofloxacin MIC Against *P. aeruginosa* PAM1001 in Presence of Efflux Pump Inhibitor (EPI)

| | Minimum Inhibitory Concentration (µg/ml) | | | | | | | |
|---|---|---|---|---|---|---|---|---|
| Compound | EPI Conc. 0 µg/ml | EPI Conc. 0.625 µg/ml | EPI Conc. 1.25 µg/ml | EPI Conc. 2.5 µg/ml | EPI Conc. 5 µg/ml | EPI Conc. 10 µg/ml | EPI Conc. 20 µg/ml | EPI Conc. 40 µg/ml |
| 36 | 4 | 4 | 4 | 4 | 4 | 2 | 1 | 0.50 |
| 37 | 4 | 4 | 4 | 1 | 0.25 | 0.03 | 0.03 | 0.06 |
| 38 | 4 | 4 | 4 | 4 | 1 | 0.25 | 0.06 | 0.015 |
| 39 | 4 | 4 | 4 | 4 | 2 | 0.50 | 0.125 | 0.03 |
| 40 | 4 | 4 | 4 | 4 | 4 | 2 | 1 | 0.25 |
| 41 | 4 | 4 | 4 | 4 | 4 | 1 | 0.50 | 0.125 |
| 42 | 4 | 4 | 4 | 4 | 2 | 0.50 | 0.06 | 0.015 |
| 43 | 4 | 4 | 4 | 4 | 4 | 2 | 0.50 | 0.125 |

TABLE 4

Levofloxacin MIC Against *P. aeruginosa* PAM1001 in Presence of Efflux Pump Inhibitor (EPI)

| | Minimum Inhibitory Concentration (µg/ml) | | | | | | | |
|---|---|---|---|---|---|---|---|---|
| Compound | EPI Conc. 0 µg/ml | EPI Conc. 0.625 µg/ml | EPI Conc. 1.25 µg/ml | EPI Conc. 2.5 µg/ml | EPI Conc. 5 µg/ml | EPI Conc. 10 µg/ml | EPI Conc. 20 µg/ml | EPI Conc. 40 µg/ml |
| 1 | 4 | 4 | 4 | 2 | 1 | 0.03 | 0.03 | 0.03 |
| 2 | 4 | 4 | 4 | 4 | 2 | 1 | 0.50 | 0.06 |
| 3 | 4 | 4 | 4 | 2 | 0.015 | 0.015 | 0.03 | NA |
| 4 | 4 | 4 | 4 | 0.25 | 0.03 | 0.03 | 0.06 | 0.06 |
| 5 | 4 | 4 | 4 | 4 | 2 | 0.125 | 0.06 | 0.06 |
| 6 | 4 | 4 | 4 | 4 | 0.03 | 0.03 | 0.03 | 0.008 |
| 7 | 4 | 4 | 4 | 2 | 0.03 | 0.06 | 0.06 | 0.03 |
| 8 | 4 | 4 | 4 | 4 | 4 | 4 | 2 | 0.50 |
| 9 | 4 | 4 | 4 | 4 | 1 | 1 | 0.06 | 0.125 |
| 10 | 4 | 4 | 4 | 2 | 0.125 | 0.03 | NA | NA |
| 11 | 4 | 4 | 2 | 1 | 0.125 | 0.03 | 0.03 | 0.03 |
| 12 | 4 | 4 | 4 | 2 | 1 | 0.06 | 0.03 | 0.06 |
| 13 | 4 | 4 | 4 | 2 | 1 | 0.125 | 0.125 | 0.125 |
| 14 | 4 | 4 | 4 | 4 | 2 | 2 | 2 | 1 |
| 15 | 4 | 4 | 4 | 2 | 1 | 0.25 | 0.06 | 0.06 |
| 16 | 4 | 4 | 4 | 4 | 2 | 0.015 | 0.03 | 0.015 |
| 17 | 4 | 4 | 4 | 4 | 0.50 | 0.50 | NA | NA |
| 18 | 4 | 4 | 4 | 4 | 2 | 0.50 | 0.125 | 0.25 |
| 19 | 4 | 4 | 4 | 4 | 4 | 2 | 1 | 0.125 |
| 20 | 4 | 4 | 4 | 2 | 1 | 0.06 | 0.06 | 0.125 |
| 21 | 4 | 4 | 4 | 4 | 2 | 1 | 0.25 | 0.06 |
| 22 | 4 | 4 | 4 | 4 | 4 | 2 | 1 | 0.50 |
| 23 | 4 | 4 | 4 | 2 | 1 | 0.06 | 0.06 | 0.06 |
| 24 | 4 | 4 | 4 | 4 | 2 | 1 | 0.125 | 0.03 |
| 25 | 4 | 4 | 2 | 0.25 | 0.125 | 0.06 | 0.125 | 0.125 |
| 26 | 4 | 4 | 4 | 4 | 1 | 0.25 | 0.125 | 0.03 |
| 27 | 4 | 4 | 4 | 4 | 2 | 2 | 1 | 1 |
| 28 | 4 | 4 | 4 | 2 | 2 | 0.25 | 0.125 | 0.125 |
| 29 | 4 | 4 | 2 | 0.25 | 0.06 | 0.015 | 0.015 | 0.015 |
| 30 | 4 | 4 | 2 | 0.25 | 0.03 | 0.03 | 0.03 | 0.015 |
| 31 | 4 | 4 | 4 | 4 | 0.50 | 0.125 | 0.015 | 0.015 |
| 32 | 4 | 4 | 2 | 0.25 | 0.125 | 0.125 | 0.06 | NA |
| 33 | 4 | 4 | 4 | 2 | 0.06 | 0.03 | 0.03 | 0.03 |
| 34 | 4 | 4 | 4 | 2 | 0.06 | 0.06 | 0.06 | 0.03 |
| 35 | 4 | 4 | 4 | 2 | 0.25 | 0.25 | NA | NA |
| 36 | 4 | 4 | 4 | 4 | 2 | 0.50 | 0.50 | NA |
| 37 | 4 | 4 | 4 | 4 | 2 | 0.06 | 0.03 | 0.06 |
| 38 | 4 | 4 | 4 | 4 | 1 | 0.25 | 0.125 | 0.03 |
| 39 | 4 | 4 | 4 | 4 | 4 | 2 | 0.50 | 0.25 |
| 40 | 4 | 4 | 4 | 0.50 | 0.50 | 0.125 | 0.125 | 0.125 |
| 41 | 4 | 2 | 0.25 | 0.06 | 0.125 | 0.06 | 0.06 | NA |
| 42 | 4 | 4 | 4 | 4 | 1 | 0.50 | 0.50 | 0.50 |
| 43 | 4 | 4 | 4 | 4 | 2 | 0.50 | 0.25 | 0.125 |
| 44 | 4 | 4 | 4 | 4 | 1 | 0.25 | 0.125 | 0.06 |

In vivo Evaluation of Efflux Pump Inhibitor Compounds

Inhibitors of the bacterial efflux pumps are generally initially characterized in vitro. Those which show effective inhibition of the pump(s) and which show synergistic activity with antibiotics are selected for evaluation in vivo. Efficacy testing will be done using standard procedures. Primary efficacy evaluation may be done using the murine septicemia model (M. G. Bergeron, 1978, *Scand. J. Infect. Dis.* Suppl. 14:189–206; S. D. Davis, 1975, *Antimicrob. Agents Chemother.* 8:50–53). In this model a supra-lethal dose of bacteria is used to challenge the rodents. Treatment is initiated, varying either or both time(s) of treatment and dose of antibiotic. In these experiments both the antibiotic and the efflux pump inhibitor doses are varied. A positive result is indicated by significant increase in protection from the lethal infection by the combination of the potentiator (the efflux pump inhibitor) and the antibiotic versus the antibiotic alone.

A second efficacy model which is used is the mouse soft tissue infection model (Vogelman et al., 1988, *J. Infect. Dis.* 157:287–298). In this model anesthetized mice are infected with an appropriate titer of bacteria in the muscle of the hind thigh. Mice are either neutropenic (cyclophosphamide treated at 125 mg/kg on days −4,−2, and 0) or immunocompetent. The infecting dose is commonly $10^5$–$10^6$ colony forming units per animal. Treatment with the combination of the efflux pump inhibitor and/or antibiotics follows infection, or can occur before infection, the proliferation (or death) of the bacteria within the thigh muscle is monitored over time. Effective combinations show greater activity than the antibiotic alone. Activity is defined as reduction in growth rate of the test bacteria in the murine tissue.

Another model useful for assessing the effectiveness of the efflux pump inhibitors is the diffusion chamber model (Malouin et al., 1990, *Infect. Immun.* 58:1247–1253; Day et al., *J. Infect.* 2:39–51; Kelly et al., 1989, *Infect. Immun.* 57:344–350). In this model rodents have a diffusion chamber surgically placed in their peritoneal cavity. The chamber can consist of a polypropylene cylinder with semipermeable membranes covering the cylinder ends. Diffusion of peritoneal fluid into and out of the chamber provides nutrients for the microbes. The proliferation of the bacteria in the presence and absence of the antibiotic/efflux pump inhibitor is compared to the antibiotic alone. Dose ranging of the combination and the antibiotic alone are done to assess effectiveness of the antimicrobial and combinations.

A tertiary model useful as a stringent test of the efflux pump inhibitor/antibiotic combination is the endocarditis model (J. Santoro and M. E. Levinson, 1978, *Infect. Immun.* 19:915–918). Either rats or rabbits are effectively used in this model. The effectiveness of combinations of efflux inhibitor and antibiotic are compared to antibiotic alone. The end point is usually viable cells remaining in the cardiac vegetations at the end of treatment.

The examples of infection models provided are not limiting. As understood by those skilled in the art, other models can be utilized as appropriate for a specific infecting microbe. In particular, cell-based infection models may be used in some circumstances instead of animal models.

Pharmaceutical Compositions and Modes of Administration

The particular compound that is an efflux pump inhibitor can be administered to a patient either by itself, or in combination with an antimicrobial, e.g., antibacterial, agent, or in pharmaceutical compositions where it is mixed with suitable carriers or excipient(s). A combination of an efflux pump inhibitor with an antimicrobial agent can be of at least two different types. In one, a quantity of an efflux pump inhibitor is combined with a quantity of an antimicrobial agent in a mixture, e.g., in a solution or powder mixture. In such mixtures, the relative quantities of the inhibitor and the antimicrobial agent may be varied as appropriate for the specific combination and expected treatment. In a second type of combination an inhibitor and an antimicrobial agent can be covalently linked in such manner that the linked molecule can be cleaved within the cell. However, the term "in combination" can also refer to other possibilities, including serial administration of an inhibitor and another antimicrobial agent. In addition, an efflux pump inhibitor and/or another antimicrobial agent may be administered in pro-drug forms, i.e. the compound is administered in a form which is modified within the cell to produce the functional form. In treating a patient exhibiting a disorder of interest, a therapeutically effective amount of an agent or agents such as these is administered. A therapeutically effective dose refers to that amount of the compound(s) that results in amelioration of symptoms or a prolongation of survival in a patient, and may include elimination of a microbial infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. It is preferable that the therapeutic serum concentration of an efflux pump inhibitor should be in the range of 0.1–100 µg/ml., more preferably 0.1–50 µg/ml.; 0.1–20 µg/ml.; 1.0–50 µg/ml.; or 1.0–20 µg/ml.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture Such information can be used to more accurately determine useful doses in humans. Levels in plasma may be measured, for example, by HPLC.

In particular preferred embodiments, the efflux inhibitor in a pharmaceutical composition has a structure as shown by the generic structures described above.

The exact formulation, route of administration and dosage can be chosen by the individual physician in view of the patient's condition. (See e.g. Fingl et al., in THE PHARMACOLOGICAL BASIS OF THERAPEUTICS, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific infection being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art, into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

EXAMPLES

The compounds of the present invention may be readily prepared in accordance with the following synthesis schemes, as illustrated in the specific examples provided. However, those skilled in the art will recognize that other synthetic pathways for forming the compounds of this invention can be utilized, and that the following is provided merely by way of example, and is not limiting to the present invention. It will be further recognized that various protecting and deprotecting strategies will be employed which are standard in the art (see, e.g., "Protective Groups in Organic Synthesis" by Greene and Wuts). Those skilled in the arts will recognize that the selection of any particular protecting group (e.g., amine and carboxyl protecting groups) will depend on the stability of the protected moiety with regard to the subsequent reaction conditions and will understand the appropriate selections.

Further illustrating the knowledge of those skilled in the art is the following sampling of the extensive chemical literature:

1) "Chemistry of the Amino Acids" by J. P. Greenstein and M. Winitz, Wiley and Sons, Inc. New York, N.Y. (1961).
2) "Comprehensive Organic Transformations" by R. Larock, VCH Publishers (1989)
3) T. D. Ocain and D. H. Rich, J. Med. Chem., 31, pp. 2193–2199 (1988).
4) E. M. Gordon, J. D. Godfrey, N. G. Delaney, M. M. Asaad, D. Von Langen, and D. W. Cushman, J. Med. Chem., 31, pp. 2199–2210 (1988).
5) "Practice of Peptide Synthesis" by M. Bodanszky and A. Bodanszky, Springer-Verlag, New York, N.Y. (1984).
6) "Protective Groups in Organic Synthesis" by T. Greene and P. Wuts (1991).
7) "Asynmmetric Synthesis: Construction of Chiral Molecules Using Amino Acids" by G. M. Coppola and H. F. Schuster, John Wiley and Sons, New York, N.Y. (1987).
8) "The Chemical Synthesis of Peptides" J. Jones, Oxford University Press, New York, N.Y. (1991).
9) "Introduction to Peptide Chemistry" by P. D. Bailey, John Wiley and Sons, New York, N.Y. (1992).
10) "Synthesis of Optically Active α-Amino Acids" by R. M. Williams, Pergamon Press, Oxford, U.K. (1989).

Scheme 1
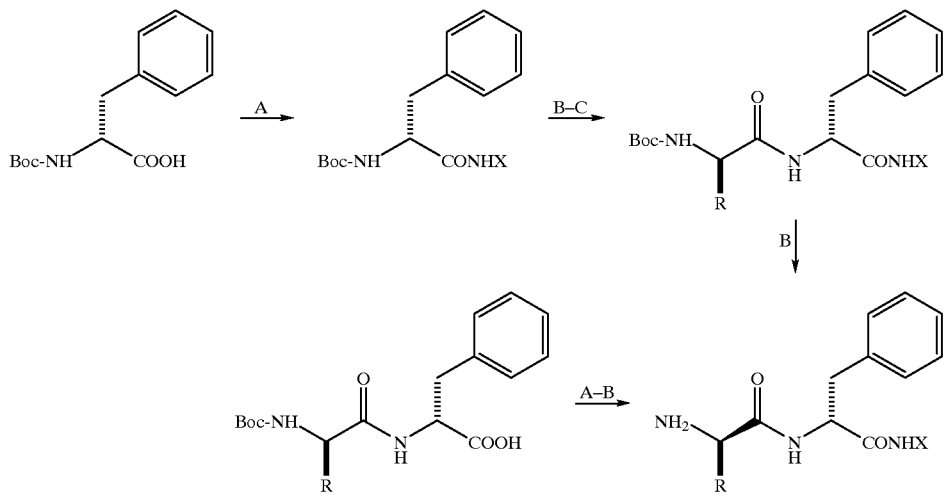
a) amide coupling conditions; b) CF₃COOH; c) Boc-amino acid, coupling agent
Scheme 2
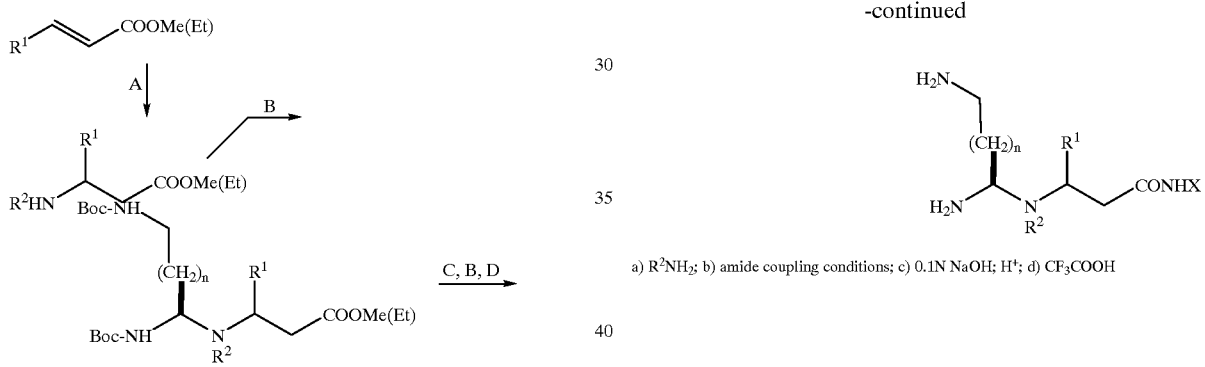
a) R²NH₂; b) amide coupling conditions; c) 0.1N NaOH; H⁺; d) CF₃COOH
Scheme 3
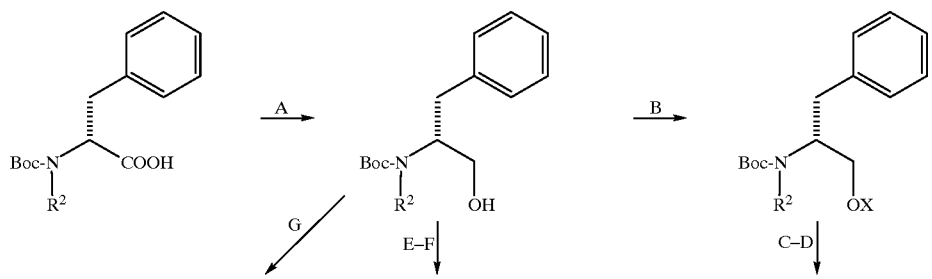

-continued

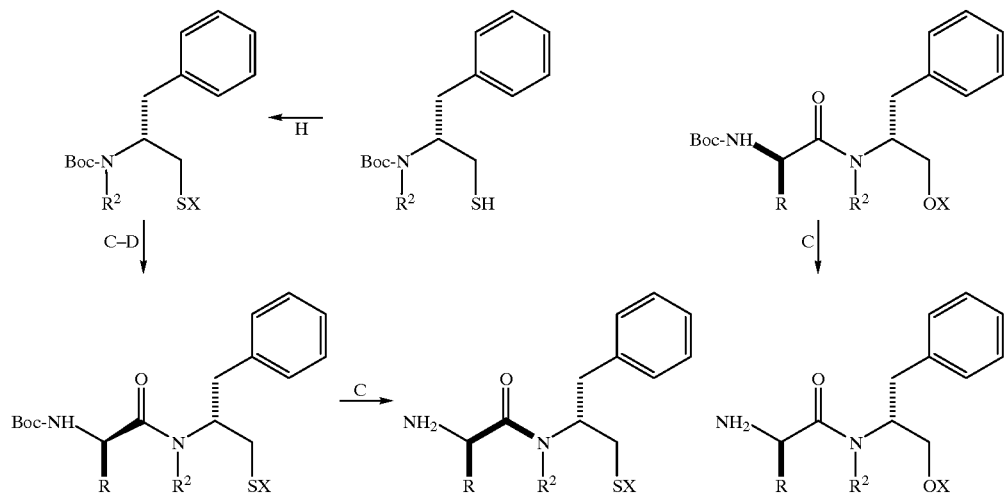

a) EtOCOCl, triethylamine; NaBH₄; b) (C₆H₅)₃P, DEAD, XOH; c) CF₃COOH; d) Boc-amino acid coupling agent; e) (C₆H₅)₃P, DEAD, CH₃COSH; f) CH₃ONa; g) (C₆H₅)³P, DEAD, XSH; h) activated heterocycles (e.g., chloropyridine, chloroquinolines)

Scheme 4

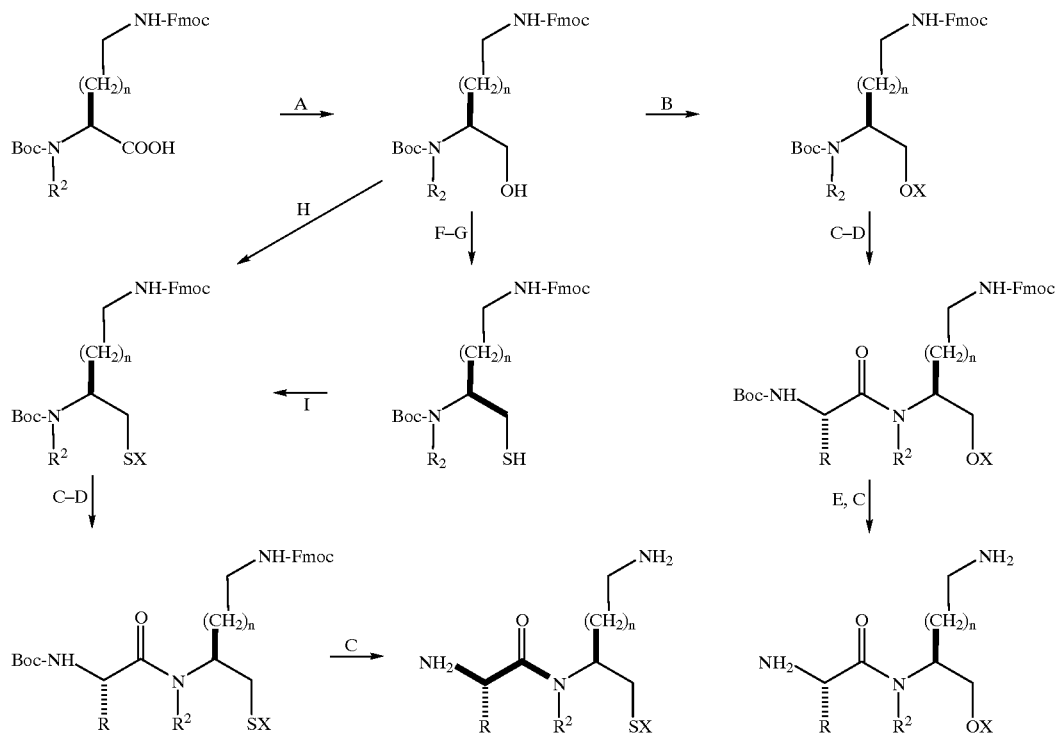

a) EtOCOCl, triethylamine; NaBH₄; b) (C₆H₅)₃P, DEAD, XOH; c) CF₃COOH; d) Boc-amino acid, coupling agent; e) 20% piperidine; f) (C₆H₅)₃P, DEAD, CH₃COSH; g) CH₃ONa; h) (C₆H₅)³P, DEAD, XSH; i) activated heterocycles (e.g., chloropyridine, chloroquinolines)

General Procedure for Phosphorus Oxychloride-Mediated Peptide Coupling Amidation (Procedure A)

A solution of N-protected amino acid in dichloromethane (0.1 M) at 0° C., under nitrogen atmosphere, is treated with phosphorus oxychloride (1.5 eq) and diisopropylethylamine (2.1 eq) followed by an alkyl (or aryl) amine (1.5 eq). The solution is stirred at 0° C. until starting material was consumed, as per thin layer chromatography monitoring. The reaction mixture is poured into ethyl acetate and worked up as usual, with purification by either chromatography or crystallization.

General Procedure for PyBrop-Mediated Peptide Coupling (Procedure B)

A solution of $N_\alpha$-(alkylamino) component, Boc-amino acid (1.3 eq), diisopropyl-ethylamine (2.0 eq), and dimethylacetamide (6 ml) was treated with benzotriazole-1-yloxytris (pyrrolidino)phosphonium hexafluorophosphate (PyBrop) (1 eq) under nitrogen at room temperature. Reaction mixture is stirred 10–12 hrs, pour into ethyl acetate, and worked up as usual, with purification by either chromatography or crystallization.

General Procedure for EDAC Mediated Peptide Coupling (Procedure C)

A solution of Boc-amino acid in dichloromethane (0.1 M), N-hydroxybenzotriazole (1 eq), and alkyl (or aryl) amine (1.6 eq) is treated with 1-ethyl-3-(3-dimethylaminopropyl) carbodiimide (1.5 eq). After stirring at room temperature for 10–12 hrs, the reaction mixture is poured into ethyl acetate and work up as usual, with purification by chromatography or crystallization.

General Procedure for Coupling of $N_\alpha$-Alkyl (or Arylalkyl) Peptides with Mixed Anhydrides (Procedure D)

A cold (0° C.) solution of Boc-amino acid (1 mmol), triethylamine (1.2 mmol), and dichloromethane (4 ml) under nitrogen atmosphere was treated with ethyl chloroformate [or pivaloyl chloride] (1.2 mmol). After stirring for 2 hrs at 0° C., a solution of secondary amine (1 mmol) in dichloromethane (3.5 ml) was added and then the reaction mixture was stirred at ambient temperature for 12–16 hrs. The reaction was worked up as in Procedure A.

General Procedure for Deprotection of tert-Butyloxycarbonyl (Boc) Peptides (Procedure E)

The starting material (10 mg) is dissolved in trifluoroacetic acid (1 ml) and stirred 1 hr, and then concentrated in vacuo. The crude material is loaded onto a reverse phase preparative HPLC. Typical HPLC conditions: 1 cm×22 cm Amberchrom; 2 ml/min flow. Solvent condition for one hour elution profiles: A: 0 to 50% acetonitrile/(0.1% TFA), B: 0 to 60% acetonitrile/(0.1% TFA); C: 0 to 70% acetonitrile/ (0.1% TFA). The fractions are concentrated to remove acetonitrile, then lyophilized.

General Procedure for Reduction of N-Protected Amino Acids to N-Protected Amino Alcohols (Procedure F)

A cold solution (0° C.) of Boc-amino acid (1 mmol) in anhydrous tetrahydrofuran (0.1 M), under nitrogen atmosphere, is treated sequentially with ethyl chloroformate (2 eq) and triethylamine (2 eq). The mixture is stirred at 0C for 2 hours. Sodium borohydride (6 eq) is added, followed by very slow addition of water (16 ml) over a period of 40 min. Once the addition is completed, the mixture is poured into ethyl acetate and worked up with final chromatographic purification.

Example 1

Alanyl-Phenylalanyl-Arginine 2-Naphthylamide Trifluoroacetate

A solution of Phe-Arg-β-naphthylamide dihydrochloride (25 mg), diisopropylethylamine (8 μl), Boc-alanine N-hydroxysuccinimide ester (14 mg), and dimethylacetamide (0.5 ml) was stirred at 25° C. for 2 hrs. After concentration in vacuo, resultant Boc-Ala-Phe-Arg 2-naphthylamide was deprotected as described in Procedure E. Product was obtained as white solid (20 mg), after HPLC (method A, retention time=43.3 min.): $^1$H NMR (400 MHz, D$_2$O) δ1.45 (d, J=8.6 Hz, 3H), 1.72 (m, 2H), 1.89 (m, 1H), 2.00 (m, 1H), 3.15 (dd, J=12.9; 8.2 Hz, 1H), 3.24 (dd, J=12.3; 8.2 Hz, 1H), 3.31 (t, J=7.1 Hz, 2H), 4.15 (q, J=8.8 Hz, 1H), 5.48 (t, J=8.0 Hz, 1H), 4.81 (HOD with proton hidden), 7.20 (m, 1H), 7.29 (m, 4H), 7.58 (d, J=10.6 Hz, 1H), 7.61 (m, 2H), and 7.99 (m, 4H).

Example 2

D-Alanyl-Phenylalanyl-Arginine 2-Naphthylamide Trifluoroacetate

This was similarly prepared, as described in Example 1. Boc-D-alanine N-hydroxysuccinimide ester was coupled to Phe-Arg-β-naphthylamide dihydrochloride; the resultant Boc-D-Ala-Phe-Arg 2-naphthylamide was deprotected with trifluoroacetic acid to afford a white solid: $^1$H NMR (400 MHz, D$_2$O ) δ1.43 (d, J=8.8 Hz, 3H), 1.74 (m, 2H), 1.90 (m, 1H), 1.99 (m, 1H), 3.17 (dd, J=12.9; 8.2 Hz, 1H), 3.21 (dd, J=12.3; 8.2 Hz, 1H), 3.29 (t, J=7.1 Hz, 2H), 4.13 (q, J=8.8 Hz, 1H), 5.50 (t, J=8.0 Hz, 1H), 4.81 (HOD with proton hidden), 7.18 (m, 1H), 7.29 (m, 4H), 7.58 (d, J=10.6 Hz, 1H), 7.63 (m, 2H), and 8.01 (m, 4H).

Example 3

D-Leucyl-Phenylalanyl-Arginine 2-Naphthylamide Trifluoroacetate

Using the procedure similar to that used in Example 1, Boc-D-leucine N-hydroxysuccinimide ester was coupled to Phe-Arg-β-naphthylamide dihydrochloride; the resultant Boc-D-Leu-Phe-Arg 2-naphthylamide was deprotected with trifluoroacetic acid to afford a white solid: $^1$H NMR (400 MHz, D$_2$O) δ0.85 (broad s, 6H), 1.29 (m, 1H), 1.52 (m, 2H), 1.77 (m, 2H), 1.98 (m, 2H), 3.07 (m, 1H), 3.29 (m, 3H), 3.99 (m, 1H), 4.54 (m, 1H), 4.81 (HOD with hidden proton), 7.22 (m, 1H), 7.36 (broad s, 4H), 7.58 (d, J=10.0 Hz, 1H), 7.63 (m, 2H), 8.01 (m, 23H), and 8.09 (s, 1H).

Example 4

Phenylalanyl-Ornithine Quinoline-3-amide Trifluoroacetate (A) N-Boc-phenylalanyl-N$_6$-Boc-ornithine p N-Boc-phenylalanine N-hydroxysuccinimide ester (1.3 g, 3.6 mmol) was dissolved in dimethylformamide (15 mL) and N$_δ$-Boc-ornithine (0.88 g, 3.8 mmol) was added in one portion. The solution was kept at 70° C. for 1 hr, cooled to 25° C., filtered to clarify and concentrated in vacuo. The residue was dissolved in ethyl acetate and washed with water. The organic phase was dried over anhydrous sodium sulfate and concentrated to dryness to afford titled compound (1.02 g) as a white foam: $^1$H NMR (400 MHz, CDCl$_3$) δ1.39–1.45 (18H), 1.70–1.72 (1H), 1.89–1.92 (1H), 3.01–3.18 (4H), 4.43 (1H), 4.58 (1H), 4.82 (1H), 5.23 (1H), 7.20–7.32 (5H).

(B) N-Boc-phenylalanyl-N$_δ$-Boc-ornithine Quinoline-3-amide

A cold solution (0° C.) of N-Boc-phenylalanyl-N$_δ$-Boc-ornithine (0.2 g, 0.4 mmol), 3-aminoquinoline (0.082 g, 0.57 mmol), diisopropylethylamine (0.103 mg, 0.8 mmol), 4-(dimethylamino)pyridine (5 mg, 0.04 mmol), and methylene chloride (3 mL) was treated dropwise with phosphorus oxychloride (0.5 mmol). The reaction was stirred at 0° C. for 1 hr and ethyl acetate (20 mL) was added. The organic layer was washed with water (2×20 mL), 1N hydrochloric acid (2×10 mL), saturated sodium bicarbonate (2×10 mL) and brine. The organic layer was dried over anhydrous sodium sulfate, filtered and the filtrate adsorbed onto 100 mg of silica gel and applied to a column prepacked with silica gel. The column was eluted with ethyl acetate/hexane (70:30, v:v) to afford titled compound (51 mg) as an oil: $^1$H NMR (400 MHz, CDCl$_3$) δ1.42–1.55 (18H), 1.6–1.8 (1H), 2.0–2.1 (1H), 3.1–3.2 (4H), 3.3–3.4 (1H), 4.19–4.21 (1H), 4.70–4.80 (1H), 5.0–5.15 (1H), 7.21–7.29 (5H), 7.53–7.55 (1H), 7.63–7.65 (1H), 7.79–7.81 (1H), 8.05–8.07 (1H), 8.74 (1H), 8.94 (1H); mass spectrum (relative intensity) m/e 606 (100, M+1).

(C) Phenylalanyl-Ornithine Quinoline-3-amide Trifluoroacetate

A solution of N-Boc-phenylalanyl-$N_\delta$-Boc-ornithine quinoline-3-amide (50 mg) and trifluoroacetic acid (2.5 mL) was stirred at 25° C. for 1 hr. The solution was concentrated in vacuo, suspended in water and applied to a MPLC reverse phase column (1 cm×22 cm, Amberchrom). The column was eluted at a rate of 2 mL/min over 1 hr (gradient of 0 to 60% acetonitrile with 0.1% TFA) and desired fractions lyophilized to afford titled dipeptide amide (46 mg): $^1$H NMR (400 MHz, $D_2O$) δ1.83–2.15 (4H), 3.11–3.15 (2H), 3.27–3.34 (2H), 4.39–4.43 (1H), 4.63–4.67 (1H), 7.17–7.34 (5H), 8.01–8.05 (1H), 8.12–8.16 (2H), 9.03 (1H), 9.37 (1H); mass spectrum (relative intensity) m/e 406 (100, M+1).

Example 5
β-N-(Phenethyl)alanine Methyl Ester

A mixture of methyl acrylate (2.0 g), phenethylamine (3.1 g), anhydrous methanol (100 ml), and glacial acetic acid (100 mg) was stirred at 25° C. for 14 hr, concentrated in vacuo and the resultant oil adsorbed onto silica gel (5 g) and applied to a column prepacked with silica gel. The title compound (2.2 g) was eluted from the column with $CH_2Cl_2$:MeOH:$NH_4OH$ (89:9:2, v:v): $^1$H NMR (400 MHz, $CDCl_3$) δ2.50–2.53 (2H), 2.79–2.94 (6H), 3.66 (3H), 7.20–7.32 (5H).

Example 6
β-N-(3-Phenylpropyl)alanine Methyl Ester

This was similarly prepared, as described in Example 5, except the starting materials are methyl acrylate and 3-phenylpropylamine.

Example 7
β-N-(p-Tolylethyl)alanine Ethyl Ester

This was similarly prepared, as described in Example 5, except the starting materials are ethyl acrylate and p-tolylethylamine.

Example 8
β-N-(iso-Butyl)alanine Ethyl Ester

This was similarly prepared, as described in Example 5, except the starting materials are ethyl acrylate and iso-butylamine.

Example 9
βN-(Cyclohexylmethyl)alanine Ethyl Ester

This was similarly prepared, as described in Example 5, except the starting materials are ethyl acrylate and cyclohexylmethylamine.

Example 10
βN-(4Fluorophenylpropyl)alanine Methyl Ester

This was similarly prepared, as described in Example 5, except the starting materials are methyl acrylate and 4-fluorophenylpropylamine.

Example 11
β-N-(Cyclopropylmethyl)alanine Methyl Ester

This was similarly prepared, as described in Example 5, except the starting materials are methyl acrylate and cyclopropylmethylamine.

Example 12
β-N-(3-Ethoxypropyl)alanine Methyl Ester

This was similarly prepared, as described in Example 5, except the starting materials are methyl acrylate and 3-ethoxypropylamine.

Example 13
D-Ornithyl-β-N-(3-Phenylpropyl)alanine Quinoline-3-amide Trifluoroacetate This was similarly prepared, as described in Example 4, in two steps. Initial coupling of $N_\alpha,N_\delta$-bis-Boc-D-ornithine and methyl β-N-(3-phenylpropyl)alaninate (Procedure B) afforded $N_\alpha,N_\gamma$-bis-Boc-D-ornithyl-β-N-(3-phenylpropyl)alanine methyl ester. Subsequent hydrolysis (0.1N sodium hydroxide), coupling with 3-aminoquinoline (Procedure A), and deprotection (Procedure E) gave the titled compound.

Example 14
D-Ornithyl-β-N-(3-Phenylpropyl)alanine 2-Naphthylamide Trifluoroacetate This was similarly prepared, as described in Example 13, except the starting materials were ethyl β-N-(3-phenylpropyl)alaninate, 2-aminonaphthalene, and $N_\alpha,N_\delta$-bis-Boc-D-ornithine,.

Example 15
D-Ornithyl-β-N-(iso-Butyl)alanine Quinoline-3-amide Trifluoroaetate This was similarly prepared, as described in Example 13, except the starting materials were methyl β-N-(iso-butyl) alaninate, 3-aminoquinoline, and $N_\alpha,N_\delta$-bis-Boc-D-ornithine.

Example 16
D-Lysyl-β-N-(iso-Butyl)alanine Quinoline-3amide Trifluoroacetate

This was similarly prepared, as described in Example 13, except the starting materials were methyl β-N-(iso-butyl) alaninate, 3-aminoquinoline, and $N_\alpha$, $N_\epsilon$-bis-Boc-D-lysine.

Example 17
D-Lysyl-β-N-(iso-Butyl)alanine (3Phenylpropyl)amide Trifluoroacetate This was similarly prepared, as described in Example 13, except the starting materials were methyl β-N-(iso-butyl) alaninate, 3-phenylpropylamine, and $N_\alpha,N_\epsilon$-bis-Boc-D-lysine.

Example 18
D-Lysyl-β-N-(Cyclohexylmethyl)alanine Quinoline-3-amide Trifluoroacetate This was similarly prepared, as described in Example 13, except the starting materials were ethyl β-N-(cyclohexylmethyl)alaninate, 3-aminoquinoline, and $N_\alpha,N_\epsilon$-bis-Boc-D-lysine.

Example 19
D-Ornithyl-β-N-(Cyclohexylmethyl)alanine 2-Naphthylamide Trifluoroacetate This was similarly prepared, as described in Example 13, except the starting materials were ethyl β-N-(cyclohexylmethyl)alaninate, 2-aminonaphthalene, and $N_\alpha,N_\delta$-bis-Boc-D-ornithine.

Example 20
D-Arginyl-β-N-(iso-Butyl)alanine Quinoline-2-amide Trifluoroacetate This was similarly prepared, as described in Example 13, except the starting materials were methyl β-N-(iso-butyl) alaninate, 2-aminoquinoline, and $N_\alpha,N_\omega,N_\omega$-tri-Boc-D-arginine.

Example 21
D-Lysyl-β-N-(iso-Butyl)alanine Quinoline-3-amide Trifluoroacetate This was similarly prepared, as described in Example 13, except starting materials were ethyl β-N-(iso-butyl)alaninate, 3-aminoquinoline, and $N_\alpha,N_\epsilon$-bis-Boc-D-lysine.

Example 22
D-Lysyl-β-N-(4Methylphenethyl)alanine Quinoline-2-amide Trifluoroacetate This was similarly prepared, as described in Example 13, except the starting materials were methyl β-N-(4-methylphenethyl)alaninate, 2-aminoquinoline, and $N_\alpha,N_\epsilon$-bis-Boc-D-lysine,.

Example 23
D-Ornithyl-βN-(4Methylphenethyl)alanine Quinoline-3-amide Trifluoroacetate This was similarly prepared, as described in Example 13, except starting materials were methyl β-N-(4-methylphenethyl)alaninate, 3-aminoquinoline, and $N_\alpha,N_\delta$-bis-Boc-D-ornithine.

Example 24
D-Ornithyl-β-N-(Ethylthioethyl)alanine 2-Naphthylamide Trifluoroacetate This was similarly prepared, as described in Example 13, except the starting materials were methyl β-N-(ethylthioethyl)alaninate, 2-aminonaphthalene, and $N_\alpha,N_\delta$-bis-Boc-D-ornithine.

Example 25
D-Lysyl-β-N-(Ethylthioethyl)alanine 2-Naphthylamide Trifluoroacetate This was similarly prepared, as described in Example 13, except starting materials were methyl β-N-(ethylthioethyl)alaninate, 2-aminonaphalene and $N_\alpha,N_\epsilon$-bis-Boc-D-lysine,

Example 26
D-Lysyl-β-N-(Ethylthioethyl)alanine Quinoline-3-amide Trifluoroacetate This was similarly prepared, as described in Example 13, except starting materials were methyl β-N-(ethylthioethyl)alaninate, 3-aminoquinoline, and $N_\alpha,N_\epsilon$-bis-Boc-D-lysine.

Example 27
D-Lysyl-β-N-(Cyclopropylmethyl)alanine Quinoline-3-amide Trifluoroacetate This was similarly prepared, as described in Example 13, except starting materials were methyl β-N-(cyclopropylmethyl)alaninate, 3-aminoquinoline, and $N_\alpha,N_\epsilon$-bis-Boc-D-lysine.

Example 28
D-Ornithyl-β-N-(Cyclopropylmethyl)alanine Quinoline-2-amide Trifluoroacetate This was similarly prepared, as described in Example 13, except the starting materials were methyl β-N-(cyclopropylmethyl)alaninate, 2-aminoquinoline, and $N_\alpha,N_\gamma$-bis-Boc-D-ornithine.

Example 29
D-Lysyl-β-N-(Cyclopropylmethyl)alanine Quinoline-2-amide Trifluoroacetate This was similarly prepared, as described in Example 13, except the starting materials were methyl β-N-(cyclopropylmethyl)alaninate, 2-aminoquinoline, and $N_\alpha,N_\epsilon$-bis-Boc-D-lysine.

Example 30
D-Lysyl-β-N-(3,3-Dimethylbutyl)alanine 2-Naphthylamide Trifluoroacetate This was similarly prepared, as described in Example 13, except starting materials were methyl β-N-(3,3-dimethylbutyl)alaninate, 2-aminonaphthalene, and $N_\alpha,N_\epsilon$-bis-Boc-D-lysine.

Example 31
Ornithyl-β-N-(3-Phenylpropyl)alanine Naphthylamide Trifluoroacetate This was similarly prepared, as described in Example 13, except starting materials were methyl β-N-(3-phenylpropyl)alaninate, 2-aminonaphthalene, and $N_\alpha,N_\delta$-bis-Boc-ornithine.

Example 32
Lysyl-β-N-(3,3-Dimethylbutyl)alanine Quinoline-3-amide Trifluoroacetate This was similarly prepared, as described in Example 13, except starting materials were methyl β-N-(3,3-dimethylbutyl)alaninate, 3-aminoquinoline, and $N_\alpha,N_\epsilon$-bis-Boc-lysine.

Example 33
D-Ornithyl-D-Phenylalanine Quinoline-3-amide Tifluoroacetate (A) N-Boc-D-phenylalanine Quinoline-3-amide A solution of N-Boc-D-phenylalanine (1.25 g, 4.7 mmol) in ethyl acetate (40 mL) was treated sequentially with 3-aminoquinoline (1.4 g, 9.4 mmol) and dicyclohexylcarbodiimide (1.02 g, 4.9 mmol). The reaction mixture was stirred at 25° C. for 16 hr, filtered and the filtrate washed with 1M hydrochloric acid (2×25 mL), saturated sodium bicarbonate (1×25 mL), and brine (1×25 mL). The organic layer was dried over anhydrous sodium sulfate, filtered and concentrated to dryness to afford titled compound (950 mg) as an oil.

(B) $N_\alpha,N_\delta$-Boc-D-ornithyl-D-Phenylalanine Quinoline-3-amide

A solution of $N_\alpha,N_\delta$-Boc-D-ornithine (253 mg, 0.76 mmol), triethylamine (81 mg, 0.8 mmol), and methylene chloride (10 ml) was stirred at 25° C. for 10 min, cooled to 0° C. and treated with ethyl chloroformate (82 mg, 0.76 mmol). The mixture was stirred at 0° C. for 2.5 hr. During this time, N-Boc-D-phenylalanine quinoline-3-amide (200 mg, 0.51 mmol) was treated with trifluoroacetic acid (5 mL) at 25° C. for 45 min. The solution was concentrated to dryness, coevaporated with methylene chloride (3×5 mL), redissolved in methylene chloride (10 mL) and neutralized to pH8 with triethyl-amine (2 eq.). This solution was added to the mixed anhydride and the mixture was stirred at room temperature for 2 hr at which time the reaction was quenched by the addition of sat. sodium bicarbonate (20 mL). The organic layer was washed with brine (10 mL), dried over anhydrous sodium sulfate, and concentrated to dryness to afford $N_\alpha,N_\delta$-Boc-D-ornithyl-D-phenylalanine quinoline-3-amide as a white solid.

(C) D-Ornithyl-D-Phenylalanine Quinoline-3-amide Trifluoroacetate $N_\alpha,N_\delta$-Boc-D-ornithyl-D-phenylalanine quinoline-3-amide was treated with trifluoro-acetic acid (20 mL) at 25° C.; after 1 hr, the reaction was concentrated in vacuo and the residue was purified by reverse-phase chromatography (Amberchrom) to afford titled compound as white solid.

Example 34
D-Ornithyl-D-β-(3-Quinolinyl)alanine (3-Phenylpropyl) amide Trifluoroacetate This was similarly prepared, as described in Example 33, except the starting materials are Boc-D-β-(3-quinolinyl) alanine, $N_\alpha,N_\beta$-bis-Boc-D-ornithine, and 3-phenylpropyl-amine.

Example 35
D-Ornithyl-D-β-(3-Quinolinyl)alanine (4-Ethylbenzyl) amide Trifluoroacetate This was similarly prepared, as described in Example 33, except starting materials are Boc-D-β-(3-quinolinyl)alanine, $N_\alpha,N_\delta$-bis-Boc-D-ornithine, and 4-ethylbenzylamine.

Example 36
D-Ornithyl-D-β-(3-Quinolinyl)alanine 2,3-Trimethylenepyridyl-5-amide Trifluoroacetate This was similarly prepared, as described in Example 33, except the starting materials are Boc-D-β-(3-quinolinyl) alanine, $N_\alpha,N_\delta$-bis-Boc-D-ornithine, and 5-amino-2,3-trimethylenepyridine.

Example 37
D-Lysyl-D-β-(3-Quinolinyl)alanine Isobutylamide Trifluoroacetate

This was similarly prepared, as described in Example 33, except the starting materials are Boc-D-β-(3-quinolinyl) alanine, $N_\alpha,N_\delta$-bis-Boc-D-lysine, and i-butylamine.

Example 38
Phenylalanyl-$N_\alpha$-Methylarginine β-Naphthylamide Trifluoroacetate (A) $N_\alpha$-Boc-$N_\delta$-Fmoc-$N_\alpha$-Methylornithine Compound is prepared using a revised literature procedure (C.-B. Xue and W. F. DeGrado, *Tetrahedron Lett.*, 36, 55 (1995), but using Fmoc-Cl instead of Cbz-Cl: $^1$H NMR (400 MHz, CDCl$_3$) δ1.45 (s, 9H), 1.60–2.15 (m, 4H), 2.80 (s, 3H), 3.00 (m, 2H), 4.50 (m, 2H), 4.18 (m, 1H), 4.21 (m, 1H), 4.42 (m, 2H), 7.33 (m, 2H), 7.39 (m, 2H), 7.59 (m, 2H), and 7.78 (d, J=8.9 Hz, 2H).

(B) $N_\alpha$-Boc-$N_\delta$-Fmoc-$N_\alpha$-Methylornithine β-Naphthylamide

This compound is prepared using Procedure A. $N_\alpha$-Boc-$N_\delta$-Fmoc-$N_\alpha$-methylornithine (80 mg), obtained in (A), and β-naphthylamine were condensed to afford a colorless solid (103 mg): $^1$H NMR (400 MHz, CDCl$_3$) δ1.53 (s, 9H), 1.85 (m, 2H), 2.15 (m, 1H), 2.94 (s, 3H), 3.30 (m, 2H), 4.25 (t, J=6.4 Hz, 1H), 4.42 (d, 2H), 4.82 (s, 1H), 5.00 (s, 1H), 7.30 (m, 2H), 7.44 (m, 8H), 7.76 (m, 2H), 7.78 (m, 2H), and 8.25 (s, 1H).

(C) Boc-Phenylalanyl-$N_\delta$-Fmoc-$N_\alpha$-Methylornithine β-Naphthylamide

This compound is prepared, using Procedure D, from Boc-phenylalanine (49 mg) and $N_\delta$-Fmoc-$N_\alpha$-methylornithine-2-naphthylamide (100 mg) to give a glassy solid (125 mg): $^1$H NMR (400 MHz, CDCl$_3$) δ 1.39 (s, 9H), 1.51 (m, 2H), 1.78 (m, 1H), 1.89 (m, 1H), 2.85 (s, 3H), 2.95–3.18 (m, 2H), 4.25 (m, 1H), 4.40 (m, 2H), 4.83 (m, 1H), 5.05 (m, 1H), 7.25 (m, 5H), 7.30 (m, 4H), 7.32 (m, 4H), 7.43 (m, 4H), 7.60 (m, 1H), and 7.80 (m, 2H).

(D) Boc-Phenylalanyl-$N_\omega,N_{\omega'}$-bis-Boc-$N_\alpha$-Methylarginine β-Naphthylamide Compound is prepared in two steps by first dissolving Boc-phenylalanyl-$N_\delta$-Fmoc-$N_\alpha$-methylornithine β-naphthylamide (100 mg), obtained from (C), in 20% piperidine in dimethylacetamide (5 ml), stirring 20 min. at ambient temperature, concentrating and drying under vacuum. The residue is then dissolved in dimethylformamide (5 ml) followed by the addition of N,N'-bis-Boc-1-guanylpyrazole (Y. Wu, G. R. Matsueda, M. Bernatowicz, *Synth. Comm.*, 23, 3055 (1993); 42 mg) and diisopropylethyl-amine (71 μl). The reaction mixture is poured into ethyl acetate, worked up as usual and the desired compound purified by flash chromatography to give titled product (103 mg) as a white solid. The compound appears as a 1:1-mixture of rotamers: $^1$H NMR (400 MHz, CDCl$_3$) δ1.41–1.90 (m, 31H), 2.67, 2.80 (2 s, total 3H), 2.91–3.10 (m, 2H), 3.45 (m, 2H), 4.22 (m), 4.61 (dd, J=11.4; 3.6 Hz, 1H), 4.86 (m, 2H), 7.20 (m, 3H), 7.25 (m, 5H), 7.43 (m, 2H), and 7.83 (m, 2H).

(E) Phenylalanyl-$N_\alpha$-Methylarginine β-Naphthylamide Trifluoroacetate

Boc-Phenylalanyl-$N_\omega,N_{\omega'}$-bis-Boc-$N_\alpha$-methylarginine β-naphthylamide was treated with trifluoroacetic acid (Procedure E), followed by HPLC purification (Method A) to afford a white solid (45 mg): $^1$H NMR (400 MHz, D$_2$O) δ1.70 (m, 2H), 1.92 (m, 1H), 2.15 (m, 1H), 2.82 (s, 3H), 3.42 (m, 4H), 4.83 (HOD with proton hidden), 5.19 (m, 1H), 7.18 (m, 2H), 7.31 (m, 1H), 7.68 (m, 4H), 8.15 (m, 4H), and 8.20 (s, 1H).

Example 39
Phenylalanyl-$N_\alpha$-Methylornithine β-Naphthylamide Trifluoroacetate A solution of Boc-phenylalanyl-$N_\delta$-Fmoc-$N_\alpha$-methylornithine β-naphthylamide (60 mg), in 20% piperidine in dimethylacetamide (5 ml), was stirred for 20 min. at 25° C., concentrated and dried under vacuum. Crude Boc-phenylalanyl-$N_\alpha$-methylornithine β-naphthylamide is then deprotected, as per Procedure E, to give a white solid which was purified by HPLC (method A): $^1$H NMR (400 MHz, D$_2$O) δ1.74 (m, 2H), 1.87 (m, 1H), 2.10 (m, 1H), 2.78 (s, 3H), 3.11 (t, J=7.6 Hz, 2H), 3.21 (dd, J=13.2, 8.8 Hz, 1H), 3.38 (dd, J=13.2; 5.2 Hz, 1H), 4.89 (HOD with proton hidden), 5.22 (t, J=7.6 Hz, 1H), 7.15 (m, 3H), 7.28 (m, 2H), 7.68 (m, 3H), 8.04 (m, 3H), and 8.13 (s, 1H).

Example 40
Phenylalanyl-$N_\alpha$-Methylornithine (2-Naphthyl) methylamide Trifluoroacetate (A) $N_\alpha$-Boc-$N_\delta$-Fmoc-$N_\alpha$-Methylornithine (2-Naphthyl) methylamide This compound is prepared using Procedure A; from $N_\alpha$-Boc-$N_\delta$-Fmoc-$N_\alpha$-methyl-ornithine and (2-naphthyl) methylamine to afford a colorless solid: $^1$H NMR (400 MHz, CDCl$_3$) δ1.42 (s, 9H), 1.56 (m, 2H), 1.78 (m, 1H), 1.95 (m, 1H), 2.82 (s, 3H), 3.28 (m, 2H), 4.21 (m, 1H), 4.39 (m, 2H), 4.51 (m, 1H), 4.69 (m, 3H), 7.40 (m, 5H), 7.51 (m, 2H), 7.58 (d, J=5.3 Hz, 2H), 7.68 (s, 1H), and 7.81 (m, 5H).

(B) Boc-Phenylalanyl-$N_\delta$-Fmoc-$N_\alpha$-Methylornithine (2-Naphthyl)methylamide This compound is prepared in two steps. $N_\alpha$-Boc-$N_\delta$-Fmoc-$N_\alpha$-methylornithine (2-naphthyl)methylamide (80 mg), obtained from (A), is deprotected with trifluoroacetic acid (5 ml), concentrated and coevaporated thrice with toluene. The crude residue is then neutralized with triethylamine in dichloromethane and coupled to Boc-phenylalanine, using Procedure D, to give title compound (24 mg) as a glassy solid: $^1$H NMR (400 MHz, CDCl$_3$) δ1.50 (s, 9H), 1.79 (m, 2H), 2.03 (m, 2H), 2.82 (s, 3H), 3.23 (m, 4H), 4.18 (m, 3H), 4.39 (m, 2H), 4.59 (dd, J=13.3; 6.1 Hz, 1H), 4.64 (dd, J=13.0; 5.5 Hz, 1H), 7.23 (m, 8H), 7.42 (m, 2H), 7.57 (m, 2H), 7.66 9s, 1H), and 7.80 (m, 7H).

(C) Phenylalanyl-$N_\alpha$-Methylornithine (2-Naphthyl)methylamide Trifluoroacetate A solution of Boc-phenylalanyl-$N_\delta$-Fmoc-$N_\alpha$-methylornithine (2-naphthyl)methylamide (24 mg) and 20% piperidine in dimethylacetamide (1.5 ml) was stirred for 20 min. at 25° C., and concentrated in vacuo. The residue is further deprotected, as per Procedure E, to give desired product (14 mg) as a white solid, HPLC (method A): $^1$H NMR (400 MHz, D$_2$O) δ1.72 (m, 2H), 1.85 (m, 11H), 2.10 (m, 1H), 2.82 (s, 3H), 3.12 (m, 4H), 4.57 (d, J=13.2 Hz, 11H), 4.75 (d, J=13.1 Hz, 1H), 4.80 (HOD with proton hidden), 5.09 (t, J=9.5 Hz, 1H), 7.08 (m, 2H), 7.24 (m, 3H), 7.59 (m, 4H), and 7.98 (m, 3H).

Example 41

Phenylalanyl-$N_\alpha$-Methylornithine 2,2-Diphenylethylamide Trifluoroacetate (A) $N_\alpha$-Boc-$N_\delta$-Fmoc-$N_\alpha$-Methylornithine 2,2-Diphenylethylamide Using Procedure A, $N_\alpha$-Boc-$N_\delta$-Fmoc-$N_\alpha$-methylornithine and 2,2-diphenylethylamine afforded a colorless solid: $^1$H NMR (400 MHz, CDCl$_3$) δ1.39 (s, 10H), 1.57 (m, 2H), 1.77 (m, 1H), 1.98 (m, 1H), 2.50 (s, 3H), 3.19 (m, 2H), 3.80 (m, 1H), 4.00 (m, 1H), 4.19 (t, J=9.5 Hz, 1H), 4.22 (m, 1H), 4.40 (d, J=7.2 Hz, 2H), 4.46 (m, 1H), 7.20–7.34 (m, 12H), 7.41 (t, J=6.6 Hz, 2H), 7.60 (d, J=8.0 Hz, 2H), and 7.79 (d, J=8.5 Hz, 2H).

(B) Phenylalanyl-$N_\alpha$-Methylornithine 2,2-Diphenylethylamide Trifluoroacetate.

$N_\alpha$-Boc-$N_\delta$-Fmoc-$N_\alpha$-methylornithine 2,2-diphenylethylamide (A) was converted in two steps (similar to that exemplified in Example 4) to a white solid: $^1$H NMR (400 MHz, D$_2$O) δ1.51 (m, 2H), 1.72 (m, 1H), 1.85 (m, 1H), 2.72 (s, 3H), 2.91 (m, 2H), 3.12 (t, J=6.1 Hz, 2H), 3.94 (dd, J=12.8, 9.1 Hz, 1H), 4.09 (dd, J=12.8, 9.0 Hz, 1H), 4.41 (t, J=7.9 Hz, 1H), 4.68 (t, J=9.6 Hz, 1H), 4.95 (t, J=9.1 Hz, 1H), and 7.22–7.53 (m, 15H).

Example 42

4-Fluorophenylalanyl-$N_\alpha$-Methylornithine β-Naphthylamide Trifluoroacetate (A) Boc-4-Fluorophenylalanyl-$N_\delta$-Boc-$N_\alpha$-Methylornithine 62-Naphthylamide Using Procedure D, Boc-4-fluorophenylalanine (138 mg) and $N_\delta$-Boc-$N_\alpha$-methylornithine β-naphthylamide (120 mg) afforded the titled compound (184 mg) as a glassy solid: $^1$H NMR (400 MHz, CDCl$_3$) δ1.41 (s, 18H), 1.62 (m, 2H), 1.80 (m, 1H), 2.02 (m, 1H), 2.82 (s, 3H), 2.92–3.20 (m, 4H), 4.61 (m, 1H), 4.82 (m, 1H), 6.70 (m, 1H), 7.05 (m, 2H), 7. 22 (m, 1H), 7.41 (m, 3H), 7.79 (m, 3H), and 8.20 (s, 1H).

(B) 4-Fluorophenylalanyl-$N_\alpha$-Methylornithine β-Naphthylamide Trifluoroacetate Deprotection of Boc-4-fluorophenylalanyl-$N_\delta$-Boc-$N_\alpha$-methylornithine β-naphthylamide (174 mg) with trifluoroacetic acid (Procedure E) afforded titled compound as a white solid (161 mg): HPLC (method A, retention time= 42.27 min); $^1$H NMR (400 MHz, D$_2$O) δ1.76 (m, 2H), 1.90 (m, 1H), 2.12 (m, 1H), 2.84 (s, 3H), 3.13 (t, J=7.6 Hz, 2H), 3.21 (dd, J=9.2; 13.6 Hz, 1H), 3.37 (dd, J=4.8; 13.2 Hz, 1H), 4.88 (t, J=9.6 Hz, 1H), 5.23 (t, J=7.6 Hz, 1H), 6.81 (t, J=8.4 Hz, 2H), 7.29 (m, 2H), 7.63 (m, 3H), 8.04 (m, 3H), and 8.14 (s, 1H).

Example 43

Tyrosyl-$N_\alpha$-Methylornithine-β-Naphthylamide Trifluoroacetate (A) Boc-Tyrosyl-$N_\delta$-Boc-$N_\alpha$-Methylornithine β-Naphthylamide Boc-tyrosine (400 mg) and $N_\delta$-Boc-$N_\alpha$-methylornithine β-naphthylamide (454 mg) were coupled (Procedure B) to afford titled compound (447 mg) as a glassy solid: $^1$H NMR (400 MHz, CDCl$_3$) δ1.50 (m, 21H), 1.77 (m, 1H), 2.73 (s, 3H), 2.76 (m, 2H), 2.99 (dd, J=10.8; 6.8 Hz, 1H), 3.09 (dd, J=12.8; 13.2 Hz, 1H), 4.70 (m, 1H), 4.87 (m, 1H), 6.89 (d, J=8.0 Hz, 2H), 7.09 (d, J=8.0 Hz, 2H), 7.41 (m, 2H), 7.75 (m, 4H), and 8.26 (s, 1H).

(B) Tyrosyl-$N_\alpha$-Methylornithine β-Naphthylamide Trifluoroacetate

Using Procedure E, Boc-tyrosyl-$N_\delta$-Boc-$N_\alpha$-methylornithine β-naphthylamide (A) (43 mg) afforded the desired compound as a white solid (36 mg): HPLC (method A, retention time=38.81 min); $^1$H NMR (400 MHz, D$_2$O) δ1.78 (m, 2H), 1.88 (m, 1H), 2.10 (m, 1H), 2.87 (s, 3H), 3.13 (m, 3H), 3.31 (dd, J=14.0; 5.6 Hz, 1H), 4.81 (HOD with proton hidden), 5.23 (t, J=7.6 Hz, 1H), 6.58 (d, J=8.4 Hz, 2H), 7.18 (d, J=8.4 Hz, 2H), 7.59 (dd, J=9.2; 2.0 Hz, 1H), 7.66 (m, 2H), 8.03 (m, 2H), 8.08 (d, J=8.8 Hz, 1H), and 8.12 (d, J=1.6 Hz, 1H); mass spectrum (ES+) m/e 435 (M+1).

Example 44

Homophenylalanyl-$N_\alpha$-Methylornithine 2-(4-Fluorophenyl)ethylamide Trifluoroacetate (A) $N_\delta$-Boc-$N_\alpha$-Benzyl-$N_\alpha$-Methylornithine 2-(4-Fluorophenyl)ethylamide $N_\delta$-Boc-$N_\alpha$-benzyl-$N_\alpha$-methylornithine and 2-(4-fluorophenyl)ethylamide were coupled, as per Procedure C, to afford titled compound as a glassy solid: $^1$H NMR (400 MHz, CDCl$_3$) δ1.52 (s, 9H), 1.73 (m, 1H), 1.65 (m, 2H), 1.79 (m, 1H), 2.78 (t, J=7.9 Hz, 2H), 3.02 (m, 1H), 3.14 (m, 2H), 3.52 (m, 4H), 6.96 (m, 2H), 7.11 (m, 5H), and 7.28 (m, 2H).

(B) $N_\delta$-Boc-$N_\alpha$-Methylornithine 2-(4-Fluorophenyl)ethylamide

Hydrogen gas was bubbled through a solution of $N_\delta$-Boc-$N_\alpha$-benzyl-$N_\alpha$-methylornithine 2-(4-fluorophenyl)ethylamide (A) (180 mg) in methanol (10 ml) in the presence 10% palladium-on-charcoal (20 mg). After starting material had disappeared, as per thin-layer chromatography monitoring, the reaction mixture was filtered through a 0.45 μm nylon pad and concentrated. The product is used as is in the subsequent step: $^1$H NMR (400 MHz, CDCl$_3$) δ1.42 (m, 11H), 1.50 (m, 2H), 2.28 (s, 3H), 2.80 (t, J=7.5 Hz, 2H), 2.94 (t, J=6.0 Hz, 1H), 3.11 (m, 2H), 3.53 (q, J=8.1 Hz, 2H), 6.98 (t, J=9.7 Hz, 2H), and 7.18 (dd, J=9.7; 8.5 Hz, 2H).

(C) Boc-Homophenylalanyl-$N_\delta$-Boc-$N_\alpha$-Methylornithine 2-(4-Fluorophenyl)ethylamide Using Procedure D, Boc-homophenylalanine (143 mg) and $N_\delta$-Boc-$N_\alpha$-methylornithine 2-(4-fluorophenyl)ethylamide (B) (crude product) gave desired compound (195 mg) as a glassy solid which was purified by flash chromatography: $^1$H NMR (400 MHz, CDCl$_3$) δ1.52 (2 s, 18H).1.71 (m, 2H), 1.82 (m, 4H), 2.62–2.80 (m, 7H), 3.12 (m, 2H), 3.45 (m, 2H), 4.61 (m, 1H), 4.92 (m, 1H), 6.89 (m, 2H), 7.13 (m, 2H), 7.20 (m, 3H), and 7.32 (m, 2H).

(D) Homophenylalanyl-$N_\alpha$-Methylornithine (4-Fluorophenyl)ethylamide Trifluoroacetate Titled compound is obtained from Boc-homophenylalanyl-$N_\delta$-Boc-$N_\alpha$-methylornithine 2-(4-fluorophenyl)ethylamide (Procedure E): HPLC (method A); $^1$H NMR (400 MHz, D$_2$O) δ1.59 (m, 2H), 1.78 (m, 1H), 1.88 (m, 1H), 2.15 (m, 2), 2.78 (s 3H), 2.83 (m, 2H), 3.09 (m, 2H), 3.58 (m, 2H), 4.48 (m, 1H), 4.95 (m, 1H), 7.12 (m, 2H), 7.23 (m, 2H), 7.38 (m, 3H), and 7.51 (m, 2H).

Example 45
4-Iodophenylalanyl-$N_\alpha$-Methylornithine (4-Fluorophenyl) ethylamide Trifuoroacetate (A) Boc-4-Iodophenylalanyl-$N_\delta$-Boc-$N_\alpha$-Methylornithine 2-(4-Fluorophenyl)ethylamide Boc-4-iodophenylalanine and $N_\delta$-Boc-$N_\alpha$-methylornithine 2-(4-fluorophenyl)ethylamide were coupled by Procedure D: $^1$H NMR (400 MHz, CDCl$_3$) δ1.38–1.51 (m, 20H), 1.82 (m, 1H), 1.90 (m, 1H), 2.78 (s, 3H), 2.80–2.97 (m, 4H), 3.00–3.17 (m, 2H), 3.28–3.44 (m, 2H), 4.63 (m, 1H), 4.97 (m, 1H), 6.94–6.99 (m, 4H), 7.11 (m, 1H), 7.18 (m, 1H), 7.58 (d, 1H), and 7.63 (dd, 1H).

(B) 4-Iodophenylalanyl-$N_\alpha$-Methylornithine 2-(4-Fluorophenyl)ethylamide TFA Boc-4-iodophenylalanyl-$N_\delta$-Boc-$N_\alpha$-methylornithine 2-(4-fluorophenyl)ethylamide was deprotected with trifluoroacetic acid (Procedure E) to afford a white solid: $^1$H NMR (400 MHz, D$_2$O) δ1.50 (m, 1H), 1.60 (m, 1H), 1.71 (m, 1H), 1.83 (m, 1H), 2.73 (s, 2H), 2.92 (m, 2H), 3.03 (m, 3H), 3.12 (m, 1H), 3.59 (m, 2H), 4.74 (m, 1H), 4.91 (m, 1H), 7.04 (d, J=8.0 Hz, 1H), 7.11 (t, J=10.9 Hz, 2H), 7.35 (m, 2H), and 7.79 (d, J=8.5 Hz, 2H).

Example 46
Homophenylalanyl-$N_\alpha$-Methylornithine 2-(4-Methylphenyl)ethylamide Trifluoroacetate (A) $N_\alpha$-Benzyl-$N_\delta$-Boc-$N_\alpha$-Methylornithine 2-(4-Methylphenyl)ethylamide $N_\alpha$-Benzyl-$N_\delta$-Boc-$N_\alpha$-methylornithine (200 mg) and 2-(4-methylphenyl)ethylamine were coupled to afford the titled compound (108 mg) as a glassy solid: $^1$H NMR (400 MHz, CDCl$_3$) δ1.45 (s, 9H), 1.58 (m, 1H), 1.65 (m, 2H), 1.75 (m, 1H), 2.13 (s, 3H), 2.35 (s, 3H), 2.81 (t, J=5.8 Hz, 2H), 3.02 (m, 1H), 3.15 (m, 2H), 3.58 (m, 4H), 7.09 (m, 6H), and 7.27 (m, 3H).

(B) $N_\delta$-Boc-$N_\alpha$-Methylornithine 2-(4-Methylphenyl)ethylamide

Catalytic reduction of $N_\alpha$-benzyl-$N_\delta$-Boc-$N_\alpha$-methylornithine 2-(4-methylphenyl)ethylamide afforded the titled compound: $^1$H NMR (400 MHz, CDCl$_3$) δ1.43 (s, 9H), 1.51 (m, 3H), 1.64 (m, 1H), 2.31 (s, 3H), 2.33 (s, 3H), 2.80 (t, J=8.6 Hz, 1H), 2.95 (m, 1H), 3.11 (m, 2H), 3.52 (m, 2H), 4.68 (m, 1H), and 7.12 (m, 4H).

(C) Boc-Homophenylalanyl-$N_\delta$-Boc-$N_\alpha$-Methylornithine 2-(4-Methylphenyl)ethylamide Using Procedure D, Boc-homophenylalanine (143 mg) and $N_\delta$-Boc-$N_\alpha$-methylornithine 2-(4-methylphenyl) ethylamide (crude product from B) afforded titled product (195 mg) as a glassy solid after silica gel chromatography: $^1$H NMR (400 MHz, CDCl$_3$) δ1.44 (2 s, 18H), 1.63 (m, 2H), 1.83 (m, 2H, 2.33 s, 3H), 2.63–279 (m, 7H), 3.09 (m, 2H), 3.45 (m, 2H), 4.51 (m, 1H), 4.98 (m, 1H), 7.09 (m, 4H) (m, 3H), and 7.31 (m, 2H).

(D) Homophenylalanyl-$N_\alpha$-Methylornithine 2-(4-Methylphenyl)ethylamide TFA Titled product (D) is obtained from Boc-homophenylalanyl-$N_\delta$-Boc-$N_\alpha$-methylornithine 2-(4-methylphenyl)ethylamide, by Procedure E, as a white solid: HPLC (method A); $^1$H NMR (400 MHz, D$_2$O) δ1.61 (m, 2H), 1.72 (m, 1H), 1.88 (m, 1H), 2.18 (m, 2H), 2.30 (s, 3H), 2.78 (s, 3H), 2.81 (m, 4H), 3.08 (m, 2H), 3.58 (m, 2H), 4.42 (m, 1H), 4.98 (m, 1H), 7.18 (m, 4H), 7.40 (m, 3H), and 7.49 (m, 2H).

Example 47
Homophenylalanyl-$N_\alpha$-Methylornithine 2,2-Diphenylethylamide Trifluoroacetate Titled compound was prepared similarly as in Example 41, except the appropriate homophenylalanine precursor was used. From $N_\alpha$-Boc-$N_\delta$-Fmoc-$N_\alpha$-methylornithine 2,2-diphenylethylamide (71 mg), there was obtained the desired compound (57 mg) as a white solid: $^1$H NMR (400 MHz, D$_2$O) δ1.62 (m, 2H), 1.72 (m, 1H), 1.89 (m, 1H), 1.97 (m, 1H), 2.06 (m, 1H), 2.61 (s, 3H), 2.79 (m, 1H), 2.85 (m, 1H), 3,03 (t, J=7.6 Hz, 2H), 3.84 (dd, J=13.2; 8.0 Hz, 1H), 4.15 (dd, J=14.0; 9.2 Hz, 1H), 4.30 (t, J=8.8 Hz, 1H), 4.38 (m, 1H), 4.97 (t, J=7.6 Hz, 1H), and 7.52 (m, 15H).

Example 48
β-(2-Thiazolyl)alanyl-$N_\alpha$-Methylornithine β-Naphthylamide Trifluoroacetate (A) Boc-β-(2-Thiazolyl)alanyl-$N_\delta$-Boc-$N_\alpha$-Methylornithine β-Naphthylamide Boc-β-(2-thiazolyl)alanine and $N_\delta$-Boc-$N_\alpha$-methylornithine β-naphthylamide were coupled under the conditions described in Procedure B, afforded a glassy solid which was purified by silica gel chromatography (1 to 2% MeOH/CH$_2$Cl$_2$): $^1$H NMR (400 MHz, CDCl$_3$) δ1.45 (s, 9H), 1.50 (s, 9H), 1.52 (m, 2H), 1.77 (m, 1H), 2.18 (m, 1H), 3.01 (s, 3H), 3.19 (m, 3H), 3.49 (m, 1H), 4.98 (m,1H), 5.36 (m, 1H), 7.12 (s, 1H), 7.43 (m, 2H), 7.59 (d, J=7.2 Hz, 1H), 7.78 (m, 3H), 8.28 (s, 1H), 8.58 (s, 1H); mass spectrum (ES+) m/e 626 (M+1).

(B) β-(2-Thiazolyl)alanyl-$N_\alpha$-methylornithine β-Naphthylamide Trifluoroacetate Deprotection of Boc-β-(2-thiazolyl)alanyl-$N_\delta$-Boc-$N_\alpha$-methylornithine β-naphthyl-amide (A), by Procedure E, afforded a white solid: $^1$H NMR (400 MHz, D$_2$O) δ1.80 (m, 2H), 1.98 (m, 1H), 2.19 (m, 1H), 3.07 (s, 3H), 3.18 (m, 2H), 3.52 (dd, J=13.0; 6.7 Hz, 1H), 3.67 (dd, J=13.0; 3.5 Hz, 1H), 5.02 (m, 1H), 5.29 (t, J=7.9 Hz, 1H), 7.48 (s, 1H), 7.65 (m, 3H), 8.03 (m, 3H), 8.17 (s, 1H), and 8.88 (s, 1H); mass spectrum (ES+) m/e 426 (M+1).

Example 49
4-(O-Dimethylaminoethyl)tyrosyl-$N_\alpha$-Methylornithine β-Naphthylamide Trifuoroacetate (A) Boc-4-(O-Dimethylaminoethyl)tyrosine A mixture of Boc-tyrosine, sodium hydride (4 eq), N,N-dimethylaminoethyl chloride hydrochloride (1.5 eq), and dimethylformamide (0.1 M) was stirred at 0° C. for 1 hr. The reaction mixture was then maintained at 25° C. (4 h), quenched with water, concentrated in vacuo and further purified by reverse phase chromatography to give titled compound as a sticky solid: $^1$H NMR (400 MHz, CDCl$_3$) δ1.39 (s, 9H), 2.75 (dd, J=17.1; 12.5 Hz, 1H), 2.89 (s, 6H), 3.08 (dd, J=12.5; 6.3 Hz, 1H), 3.48 (m, 2H), 4.19 (m, 1H), 4.28 (m, 2H), 6.88 (d, J=9.9 Hz, 2H), and 7.15 (d, J=9.0 Hz, 2H).

(B) Boc-4-(O-Dimethylaminoethyl)tyrosyl-$N_\delta$-Boc-$N_\alpha$7-Methylornithine β-Naphthylamide Using Procedure B, Boc-4-(O-Dimethylaminoethyl) tyrosine (31 mg) and $N_\delta$-Boc-$N_\alpha$-methylornithine β-naphthylamide (43 mg) were condensed to afford a glassy solid (26 mg) after chromatography: $^1$H NMR (400 MHz, CDCl$_3$) δ1.42–1.57 (m, 21H), 1.77 (m, 1H), 2.79 (m, 4H), 2.95 (m, 2H), 3.02 (s, 6H), 3.10 (m, 1H), 3.61 (m, 2H), 4.33 (m, 3H), 4.64 (m, 1H), 6.90 (d, J=8.5 Hz, 2H), 7.18 ((d, J=8.5 Hz, 2H), 7.41 (m, 3H), 7.74 (m, 3H), and 8.11 (s, 1H); mass spectrum (ES+) m/e 706 (M+1).

(C) 4-(O-Dimethylaminoethyl)tyrosyl-N$_\alpha$-Methylornithine β-Naphthylamide Trifluoroacetate Titled product was obtained from Boc-4-(O-dimethylaminoethyl)tyrosyl-N$_\delta$-Boc-N$_\alpha$-methylornithine β-naphthylamide after exposure to trifluoroacetic acid: HPLC (method A, retention time=35.36 min); $^1$H NMR (400 MHz, D$_2$O) δ1.80 (m, 3H), 2.07 (m, 1H), 2.69 (s, 9H), 2.81 (m, 2H), 3.01–3.29 (m, 3H), 3.42 (dd, J=11.8; 4.1 Hz, 1H), 3.57 (m, 1H), 4.81 (HOD with 3H hidden), 5.27 (t, J=6.4 Hz, 1H), 6.58 (d, J=9.9 Hz, 2H), 7.26 (d, J=9.9 Hz, 2H), 7.67 (m, 3H), 8.08 (m, 3H), and 8.21 (s, 1H), mass spectrum (ES+) m/e 507 (M+1).

Example 50

4-(O-Methylcarboxyamido)tyrosyl-N$_\alpha$-Methylornithine β-Naphthylamide Trifluoroacetate (A) Boc-4-(O-Methylcarboxyamido)tyrosyl-N$_\delta$-Boc-N$_\alpha$Methylornithine β-Naphthylamide A mixture of Boc-tyrosyl-N$_\delta$-Boc-N$_\alpha$-methylornithine β-naphthylamide (43 mg), tetrabutylammonium bromide (5.8 mg), iodoacetamide (14 mg), potassium carbonate (45 mg), and dimethylformamide (0.7 ml) was stirred at 25° C. for 10 hrs. The mixture was then poured into ethyl acetate and worked up to give titled product (47.6 mg) which is used crude: $^1$H NMR (400 MHz, CDCl$_3$) δ1.48 (s, 18H), 1.82 (m, 4H), 2.79 (s, 3H), 2.82–3.18 (m, 4H), 4.09 (m, 1H), 4.50 (m, 2H), 4.83 (m, 1H), 6.97 (d, J=9.8 Hz, 2H), 7.21 (d, J=9.8 Hz, 2H), 7.43 (m, 3H), 7.79 (m, 3H), and 8.03 (s, 1H); mass spectrum (ES+) m/e 714 (M+23).

(B) 4-(O-Methylcarboxyamido)tyrosyl-Nα-Methylornithine β-Naphthylamide TFA

Treatment of Boc-4-(O-methylcarboxyamido)tyrosyl-N$_\delta$-Boc-N$_\alpha$-methylornithine β-naphthylamide with trifluoroacetic acid (Procedure E) afforded titled product as a white solid; HPLC (method A, retention time=37.34 min); $^1$H NMR (400 MHz, D$_2$O) δ1.79 (m, 3H), 2.06 (m, 1H), 2.80 (s, 3H), 3.12 (m, 3H), 3.41 (dd, J=13.2; 4.4 Hz, 1H), 3.66 (dd, J=14.8; 2.8 Hz, 1H), 3.83 (d, J=14.8 Hz, 1H), 4.93 (m, 1H), 5.22 (t, J=6.8 Hz, 1H), 6.61 (d, J=7.2 Hz, 2H), 7.28 (d, J=7.2 Hz, 2H), 7.55 (d, J=9.2 Hz, 1H), 7.65 (m, 2H), 7.97 (d, J=8.4 Hz, 1H), 8.01 (d, J=7.2 Hz, 1H), and 8.06 (m, 2H); mass spectrum (ES+) m/e 492 (M+1).

Example 51

β-(1-Naphthyl)alanyl-N$_\alpha$-Methylornithine Benzylamide Trifluoroacetate (A) N$_\alpha$-Boc-N$_\delta$-Fmoc-N$_\alpha$-Methylornithine Benzylamide This compound is prepared using Procedure C. N$_\alpha$-Boc-N$_\delta$-Fmoc-N$_\alpha$-methylornithine (100 mg) was coupled with benzylamine to afford titled compound (50 mg) as a glassy solid: $^1$H NMR (400 MHz, CDCl$_3$) δ1.42 (s, 9H), 1.52 (m, 2H), 1.70 (m, 2H), 2.80 (s, 3H), 3.26 (m, 2H), 4.18 (m, 1H), 4.22 (m, 1H), 4.41 (m, 2H), 4.61 (m, 2H), 7.31 (m, 7H), 7.43 (m, 2H), 7.63 (m, 2H), and 7.81 (m, 2H).

(B) Boc-β-(1-Naphthyl)alanyl-N$_\delta$-Fmoc-N$_\alpha$-Methylornithine Benzylamide This compound is prepared in two steps. N$_\alpha$-Boc-N$_\delta$-Fmoc-N$_\alpha$-methylornithine benzylamide (A) (115 mg) is deprotected with trifluoroacetic acid (5 ml), concentrated and coevaporated thrice with toluene. The residue is coupled with Boc-β-(1-naphthyl)-alanine (87 mg), using Procedure D, to give the titled product (45 mg) as a glassy solid: $^1$H NMR (400 MHz, CDCl$_3$) δ1.42 (s, 9H), 1.56 (m, 2H), 1.62 (m, 2H), 2.59 (s, 3H), 3.18 (m, 2H), 3.40 (dt, 1H), 3.59 (dd, 1H), 4.18 (m, 1H), 4.21 (m, 1H), 4.36 (m, 2H), 4.44 (d, 2H), 7.20–7.40 (m, 12H), 7.60 (m, 4H), and 7.79 (m, 4H), (C) β-(1-Naphthyl)alanyl-N$_\alpha$-Methylornithine Benzylamide Trifluoroacetate Boc-β-(1-Naphthyl)alanyl-N$_\delta$-Fmoc-N$_\alpha$-methylornithine benzylamide (B) (28 mg) was deprotected in teo steps-i) 20% piperidine in dimethylformamide and ii) trifluoroacetic acid exposure to afford a white solid: HPLC (method A); $^1$H NMR (400 MHz, D$_2$O) δ1.59 (m, 2H), 1.77 (m, 1H), 1.89 (m, 1H), 2.38 (s, 3H), 3.0 (t, 2H), 3.60 (dd, 1H), 3.82 (dd, 1H), 4.39 (d, 2H), 4.92 (t, 1H), 5.01 (dd, 1H), 7.36–7.50 (m, 12H), 7.75 (m, 2H), 7.99 (t, 1H), 8.10 (d, 1H), and 8.18 (d, 1H).

Example 52

β-(2-Naphthyl)alanyl-N$_\alpha$-Methylornithine Benzylamide Trifluoroacetate

This compound was prepared from N$_\delta$-Fmoc-N$_\alpha$-methylornithine benzylamide and Boc-β-(2-naphthyl) alanine, similar to the procedure in Example 51: $^1$H NMR (400 MHz, D$_2$O) δ1.60 (m, 2H), 1.79 (m, 11H), 1.98 (m, 11H), 2.82 (s, 3H), 3.03 (t, 2H), 3.37 (dd, 1H), 3.46 (dd, 1H), 4.22 (s, 2H), 4.97 (m, 2H), 7.30 (d, 1H), 7.39 (d, 1H), 7.43 (m, 3H), 7.66 (m, 2H), 7.85 (s, 1H), 7.97 (d, 2H), and 8.02 (m, 2H).

Example 53

β-(2-Naphthyl)alanyl-N$_\alpha$-Methylornithine 2-(4-Hydroxyphenyl)ethyl-amide Trifluoroacetate (A) N$_\alpha$-Benzyl-N$_\delta$-Boc-N$_\alpha$-Methylornithine 2-(4-Hydroxyphenyl)ethylamide This compound is prepared using Procedure C by coupling of N$_\alpha$-benzyl-N$_\delta$-Boc-N$_\alpha$-methylornithine and (4-hydroxyphenyl)ethylamine.

(B) N$_\delta$-Boc-N$_\alpha$-Methylornithine 2-(4-Hydroxyphenyl)ethylamide

Hydrogen gas was bubbled through a solution of N$_\alpha$-benzyl-N$_\delta$-Boc-N$_\alpha$-methylornithine 2-(4-hydroxyphenyl)ethylamide (A) (540 mg) in ethanol (20 ml) in the presence of 1 eq. of conc. hydrochloric acid (1.30 ml) and 5% palladium-on-charcoal (50 mg). After disappearance of starting material, as determined by thin-layer chromatography, the reaction mixture is filtered through a 0.45 μm nylon pad and concentrated in vacuo.

(C) Boc-β-(2-Naphthyl)alanyl-N$_\delta$-Boc-N$_\alpha$-Methylornithine 2-(4-Hydroxyphenyl)ethylamide Using Procedure B, coupling of Boc-β-(2-naphthyl) alanine and N$_\delta$-Boc-N$_\alpha$-methylornithine 2-(4-hydroxyphenyl)ethylamide, followed by silica gel chromatography (2.5% MeOH/CH$_2$Cl$_2$): $^1$H NMR (400 MHz, CDCl$_3$) 6 1.41 (m, 21H), 1.85 (m, 1H), 2.20 (m, 2H), 2.45 (m, 1H), 2.67 (m, 4H), 3.03 (m, 4H), 4.91 (m, 2H), 6.77 (m, 2H), 6.87 (d, J=8.7 Hz, 1H), 6.98 (d, J=10.0 Hz, 1H), 7.34 (m, 1H), 7.46 (m, 2H), 7.66 (m, 1H), and 7.78 (m, 3H); mass spectrum (ES+) m/e 663 (M+1).

(D) β-(2-Naphthyl)alanyl-N$_\alpha$-Methylornithine 2-(4-Hydroxyphenyl)ethylamide TFA Boc-β-(2-Naphthyl)alanyl-N$_\delta$-Boc-N$_\alpha$-methylornithine 2-(4-hydroxyphenyl)ethylamide (C) was transformed, by Procedure E, to a white product; HPLC (method C); $^1$H NMR (400 MHz, CD$_3$OD) δ1.62 (m, 3H), 1.86 (m, 1H), 2.63 (t, J=7.6 Hz, 2H), 2.79 (s, 3H), 2.91 (m, 2H), 3.21 (m, 2H), 4.71 (t, J=6.0 Hz, 1H), 4.94 (t, J=6.5 Hz, 1H), 6.69 (d, J=9.4 Hz, 2H), 7.02 (d, J=9.4 Hz, 2H), 7.39 (d, J=10.5 Hz, 1H), 7.48 (m, 2H), 7.78 (s, 1H), and 7.84 (m, 3H); mass spectrum (ES+) m/e 463 (M+1).

Example 54
D-Ornithyl-D-β-Naphthyl)alanine Benzylamide Trifluoroacetate (A) Boc-D-β-(2-Naphthyl)alanine Benzylamide A mixture of Boc-D-β-(2-naphthyl)alanine (305 mg), benzylamine (165 μl), and ethyl acetate (10 ml) was treated with a solution of dicyclohexylcarbodiimide (212 mg) in ethyl acetate (5 ml). The mixture was stirred 3 h at 25° C. and filtered. The mother liquor was diluted with ethyl acetate and worked up as usual. The crude residue is used in the subsequent step: $^1$H NMR (400 MHz, CDCl$_3$) δ1.38 (s, 9H), 3.01 (dd, 1H), 3.34 (dd, 1H), 4.18 (m, 1H), 4.38 (t, 1H), 4.42 (m, 1H), 7.00 (m, 2H), 7.19 (m, 2H), 7.33 (m, 2H), 7.49 (m, 2H), 7.66 (d, 1H), and 7.81 (m, 3H).

(B) N$_α$,N$_δ$-Boc-D-Ornithyl-D-β-(2-Naphthyl)alanine Benzylamide

Boc-D-(2-naphthyl)alanine benzylamide (A) (275 mg) is treated with trifluoroacetic acid (5 ml), concentrated and coevaporated thrice with toluene. The crude D-(2-naphthyl) alanine benzylamide, N$_α$,N$_δ$-Boc-ornithine (225 mg), diisopropylethylamine (121 μl), 1-ethyl-3-(3-dimethylaminopropyl)carbodiimide (135 mg), and methylene chloride (5 ml) was stirred for 3 hr at 25° C. The reaction mixture is then poured into ethyl acetate and worked up as usual; the crude product is used in the subsequent step: $^1$H NMR (400 MHz, CDCl$_3$) δ1.42 (s, 18H), 1.77 (m, 2H), 1.98 (m, 2H), 2.97 (m, 1H), 3.08 (m, 1H), 3.26 (dd, 1H), 3.39 (m, 1H), 4.04 (m, 1H), 4.37 (m, 2H), 4.79 (q, 1H), 7.03 (m, 2H), 7.18 (m, 3H), 7.38 (d, 1H), 7.49 (m, 2H), 7.63 (s, 1H), and 7.79 (m, 3H).

(C) D-Ornithyl-D-β-(2-Naphthyl)alanine Benzylamide Trifluoroacetate

Treatment of N$_α$,N$_δ$-Boc-D-ornithyl-D-β-(2-naphthyl) alanine benzylamide (B) with trifluoroacetic acid afforded the desired product as a white solid: HPLC (method A, retention time=40.43 min); $^1$H NMR (400 MHz, D$_2$O) δ1.80 (m, 2H), 2.02 (m, 2H), 3.06 (m, 2H), 3.23 (dd, 1H), 3.42 (dd, 1H), 4.06 (d, 1H), 4.17 (t, 1H), 4.39 (dd, 1H), 4.81 (HOD with proton hidden), 6.70 (d, 2H), 6.99 (t, 2H), 7.18 (t, 1H), 7.47 (d, 1H), 7.64 (m, 2H), 7.70 (s, 1H), 7.93 (m, 2H), and 8.02 (m, 1H); mass spectrum (ES+) m/e 419 (M+1).

Example 55
D-Ornithyl-D-β-(1-Naphthyl)alanine Benzylamide Trifluoroacetate (A) Boc-D-β-(1-Naphthyl)alanine Benzylamide This compound is prepared by coupling of Boc-D-β-(1-naphthyl)alanine and benzylamine by Procedure C: $^1$H NMR (400 MHz, CDCl$_3$) δ1.40 (s, 9H), 3.46–3.61 (m, 2H), 4.19 (m, 1H), 4.26 (dd, 1H), 4.50 (q, 1H), 7.21 (m, 3H), 7.36 (m, 3H), 7.49 (m, 1H), 7.58 (t, 1H), 7.78 (m, 1H), 7.85 (t, 1H), and 8.20 (d, 1H).

(B) N$_α$,N$_δ$-Boc-D-Ornithyl-D-β-(1-Naphthyl)alanine Benzylamide

This compound is prepared by coupling D-β-(1-naphthyl) alanine benzylamide and N$_α$,N$_δ$-Boc-D-ornithine, in the presence of diisopropylethylamine and 1-ethyl-3-(3-dimethylaminopropyl)carbodiimide, in methylene chloride: $^1$H NMR (400 MHz, CDCl$_3$) δ1.38 (s, 9H), 1.43 (m, 11H), 1.64 (m, 2H), 3.02 (m, 1H), 3.11 (m, 1H), 4.06 (m, 2H), 4.22 (dd, 1H), 4.33 (dd, 1H), 4.79 (q, 1H), 7.00 (m, 2H), 7.22 (m, 3H), 7.36 (m, 2H), 7.61 (t, 1H), 7.68 (t, 1H), 7.77 (d, 1H), 7.85 (d, 1H), and 8.21 (d, 1H).

(C) D-Ornithyl-D-β-(1-Naphthyl)alanine Benzylamide Trifluoroacetate

The titled product was obtained from N$_α$,N$_δ$-Boc-D-ornithyl-D-β-(1-naphthyl)alanine benzylamide (B) by Procedure E; HPLC (method A, retention time=37.15 min.); $^1$H NMR (400 MHz, D$_2$O) δ1.83 (m, 2H), 2.05 (m, 2H), 3.10 (m, 2H), 3.56 (dd, 1H), 3.73 (dd, 1H), 4.02 (d, 1H), 4.19 (m, 1H), 6.75 (d, 2H), 7.30 (m, 2H), 7.45 (t, 1H), 7.48 (t, 1H), 7.68 (m, 2H), 7.87 (d, 1H), 8.08 (d, 1H), 8.14(t, 1H), and 8.19 (d, 1H).

Example 56
D-Ornithyl-D-β-(2Naphthyl)alanine 2-(4-Hydroxyphenyl (ethylamide Tifluoroacetate (A) Boc-D-β-(2-Naphthyl)alanine 2-(4-Hydroxyphenyl) ethylamide This compound is prepare, by Procedure C, by coupling of Boc-D-β-(2-naphthyl)alanine with 2-(4-hydroxyphenyl) ethylamine: $^1$H NMR (400 MHz, CD$_3$OD) δ1.36 (s, 9H), 2.57 (m, 2H), 2.97 (dd, J=13.8; 11.6 Hz, 1H), 3.18–3.40 (m, 3H), 4.32 (m, 1H), 6.67 (d, J=1 1.4 Hz, 2H), 6.91 (d, J=10.1 Hz, 2H), 7.34 (d, J=9.5 Hz, 1H), 7.41 (m, 2H), 7.66 (s, 1H), and 7.79 (m, 3H).

(B) N$_α$,N$_δ$-Boc-D-Ornithyl-D-β-(2-Naphthyl)alanine 2-(4-Hydroxyphenyl)ethylamide The titled compound is prepared by coupling D-β-(2-naphthyl)alanine 2-(4-hydroxyphenyl)ethylamide and N$_α$,N$_α$-Boc-D-ornithine by Procedure C: $^1$H NMR (400 MHz, CDCl$_3$) δ1.36 (s, 9H), 1.47 (broad s, 12H), 1.59 (m, 1H), 2.57 (m, 2H), 2.97 (m, 2H), 3.25 (m, 2H), 3.36 (m, 2H), 4.00 (m, 1H), 4.72 (m, 1H), 6.70 (d, J=10 Hz, 2H), 6.79 (d, J=10 Hz, 2H), 7.30 (d, J=11 Hz, 1H), 7.43 (m, 2H), 7.62 (s, 1H), and 7.74 (m, 3H); mass spectrum (ES+) m/e 647 (M+1).

(C) D-Ornithyl-D-β-(2-Naphthyl)alanine 2-(4-Hydroxyphenyl)ethylamide TFA

The titled product was obtained from N$_α$,N$_δ$-Boc-D-ornithyl-D-β-(2-naphthyl)alanine 2-(4-hydroxyphenyl) ethylamide, by the Procedure E, as a white solid: HPLC (method C); $^1$H NMR (400 MHz, D$_2$O) δ1.79 (m, 2H), 1.98 (m, 2H), 2.34 (m, 1H), 2.42 (m, 1H), 3.05 (m, 2H), 3.18 (dd, J=12.9; 11.0 Hz, 1H), 3.26 (dd, J=13.7; 11.0 Hz, 1H), 3.42 (m, 1H), 4.07 (t, J=9.0 Hz, 1H), 4.63 (t, J=9.6 Hz, 1H), 6.72 (d, J=10.0 Hz, 2H), 6.80 (d, J=10.0 Hz, 2H), 7.44 (d, J=11.5 Hz, 1H), 7.64 (m, 2H), 7.80 (s, 1H), and 7.97 (m, 3H); mass spectrum (ES+) m/e 449 (M+1).

Example 57
D-Ornithyl-D-β-(2Naphthyl)alanine Isoamylamide Trifluoroacetate (A) Boc-D-β-(2-Naphthyl)alanine Isoamylamide Boc-D-β-(2-naphthyl)alanine (190 mg) and isoamylamine were coupled using a modification of Procedure C to afford titled compound (233 mg) as a glassy solid: $^1$H NMR (400 MHz, CDCl$_3$) δ0.89 (t, 6H), 1.38 (m, 1H), 1.08 (m, 2H), 1.42 (s, 9H), 3.18 (m, 3H), 3.26 (dd, 1H), 4.39 (q, 1H), 7.38 (d, 1H), 7.45 (m, 2H), 7.64 (m, 1H), and 7.80 (m, 3H).

(B) N$_α$,N$_δ$-Boc-D-Ornithyl-D-β-(2-Naphthyl)alanine Isoamylamide

A solution of Boc-β-(2-naphthyl)alanine isoamylamide (225 mg) and trifluoroacetic acid (8 ml), was stirred for 2 hrs, concentrated and coevaporated thrice with toluene. This residue is dissolved in dichloromethane (10 ml) and N$_α$,N$_δ$-Boc-D-ornithine (293 mg), diisopropylethylamine (0.14 ml) and 1-ethyl-3-(3-dimethylaminopropyl)carbodiimide (240 mg) added. After stirring for 10 hrs, the mixtures was poured into ethyl acetate and worked up as usual. Flash chromatography gave (B) (350 mg) as a glassy solid: $^1$H NMR (400 MHz, CDCl$_3$) δ0.80 (t, 6H), 1.20 (m, 2H), 1.26 (s, 9H), 1.38 (m, 1H), 1.41 (s, 9H), 1.57 (m, 2H), 1.71 (m, 2H), 2.97 (m, 1H), 3.10 (m, 2H), 3.22 (m, 2H), 3.37 (dd, 1H), 4.02 (q, 1H), 4.73 (q, 1H), 7.35 (dd, 1H), 7.46 (m, 2H), 7.65 (s, 1H), and 7.80 (m, 3H).

(C) D-Ornithyl-D-β-(2-Naphthyl)alanine Isoamylamide Trifluoroacetate

Deprotection of $N_\alpha,N_\delta$-Boc-D-ornithyl-D-β-(2-naphthyl)alanine isoamylamide (B) (341 mg), by Procedure E, afforded titled product as a white solid (308 mg): HPLC (method A, retention time=38.50 min); $^1$H NMR (400 MHz, D$_2$O) δ0.50 (dd, 6H), 0.91 (m, 3H), 1.81 (m, 1H), 2.02 (m, 2H), 2.83 (m, 1H), 3.09 (m, 3H), 3.17 (dd, 1H), 3.30 (dd, 1H), 4.06 (t, 1H), 4.62 (dd, 1H), 7.50 (d, 1H), 7.61 (m, 2H), 7.79 (m, 1H), and 7.99 (m, 3H).

Example 58
D-Ornithyl-N-Phenethyl)glycine 2-Naphthylamide Trifluoroacetate
(A) Methyl N-(phenethyl)glycinate A cold solution (0° C.) of glycine methyl ester hydrochloride (1.0 g, 8 mmol), methanol (25 mL), glacial acetic acid (0.8 mmol, and phenylacetaldehyde (0.481 g, 4 mmol) was treated with sodium triacetoxyborohydride (1.7 g, 8 mmol) in two portions. The reaction mixture was maintained at 0° C. for 1.5 hr, and then quenched with saturated sodium bicarbonate (15 mL). The solution was extracted with ethyl acetate. The organic phase was collected, dried over anhydrous sodium sulfate, and adsorbed onto silica gel (100 mg) and applied to a column prepacked with silica gel. The column was eluted with CH$_2$Cl$_2$/MeOH (97:3, v:v) to afford titled compound (258 mg).

(B) Methyl N-Boc-N-(phenethyl)glycinate

Methyl N-(phenethyl)glycinate (250 mg, 1.3 mmol) was dissolved in 20 mL of 1:1-water/dioxane, and sodium bicarbonate (2.6 mmol) and di-tert-butyl dicarbonate (1.9 mmol) were added. After 14 hr at 25° C., the dioxane was concentrated in vacuo and the aqueous solution neutralized to pH4 with 5% citric acid (5 mL) and extracted with ethyl acetate. The organic phase was collected, dried over anhydrous sodium sulfate, and concentrated in vacuo to afford titled compound (358 mg): $^1$H NMR (400 MHz, CDCl$_3$) δ1.44–1.46 (9H), 2.80–2.89 (2H), 3.46–3.54 (2H), 3.73 (3H), 3.77 (1H), 3.89 (1H), and 7.0–7.3 (5H).

(C) N-Boc-N-(Phenethyl)glycine

A solution of methyl N-Boc-N-(phenethyl)glycinate (0.358 g, 1.2 mmol), methanol (20 mL) and 1M sodium hydroxide (2.4 ml, 2.4 mmol) was stirred for 14 hr at 25° C. After concentration in vacuo, the residue was dissolved in water (25 mL) and adjusted to pH4 with 5% citric acid (10 mL). The mixture was extracted with ethyl acetate (30 mL) and the organic phase dried over anhydrous sodium sulfate, and concentrated to afford titled carboxylic acid (311 mg).

(D) $N_\alpha,N_\delta$-Bis-Boc-D-ornithyl-N-(phenethyl)glycine 2-Naphthylamide

A solution (0° C.) of $N_\alpha,N_\delta$-bis-Boc-D-ornithine (130 mg, 0.39 mmol), diisopropylethylamine (1.6 mmol) and methylene chloride (10 mL) was treated with PyBroP (275 mg, 0.59 mmol) and kept at 0° C. for 30 min. In another reaction, a solution of Boc-N-(phenethyl)glycine 2-naphthylamide (240 mg, 0.59 mmol) (made by coupling of N-Boc-N-(phenethyl)glycine and 2-naphthylamine) and trifluoroacetic acid (3 mL) was stored at 24° C. for 1 hr and then concentrated in vacuo. The residue was coevaporated twice with methylene chloride and the resultant solid resuspended in methylene chloride (10 mL) and treated with diisopropylethylamine (1.2 mmol). The two solutions were mixed and stirred at 25° C. for 1 hr at which time the mixture was washed with 1M hydrochloric acid (2×25 mL), sat. sodium bicarbonate (25 mL), and brine (25 mL). The organic layer was dried over anhydrous sodium sulfate and adsorbed onto silica gel (500 mg) and applied to a column prepacked with silica gel. The column was eluted with ethyl acetate:hexane (50:50, v:v) to afford the titled compound.

(E) D-Ornithyl-N-(Phenethyl)glycine 2-Naphthylamide Trifluoroacetate

A solution of $N_\alpha,N_\delta$-bis-Boc-D-ornithyl-N-(phenethyl)glycine 2-naphthylamide (100 mg) and trifluoroacetic acid (10 mL) was maintained at 25° C. for 1 hr, and then concentrated in vacuo. The residue was chromatographed on a reverse-phase column (Amberchrome) with elution with acetonitrile/0.1% aqueous trifluoroacetic acid. The appropriate fractions were lyophilized to afford the titled compound (45 mg):

Example 59
Homophenylalanyl-$N_\alpha$-Methylornithine 3-Phenylpropylamide Trifluoroacetate A solution of $N_\alpha$-benzyl-$N_\delta$-Boc-$N_\alpha$-methylornithine (300 mg), diisopropylethylamine (326 μl), and anhydrous tetrahydrofuran (4 ml) was treated with PyBop (585 mg) at 0° C. for 10 min., followed by the addition of a solution of 3-phenylpropylamine (147 μl) in anhydrous tetrahydrofuran (2 ml). The resulting solution was stirred at ambient temperature for 4 hrs. The reaction was diluted with ethyl acetate and washed with water. The organic layer was dried over anhydrous sodium sulfate and concentrated in vacuo. The product was purified by chromatography over silica gel (hexane/ethyl acetate) to give $N_\alpha$-benzyl-$N_\delta$-Boc-$N_\alpha$-methylornithine 3-phenylpropylamide (370 mg): $^1$H NMR (400 MHz, CDCl$_3$) δ1.43 (s, 9H), 1.6–1.9 (m, 6H), 2.2 (s, 3H), 2.65 (t, J=6.2 Hz, 2H), 3.0–3.4 (m, 5H), 3.64 (s, 2H), 4.8 (s, 1H), and 7.1–7.5 (m, 10H).

A mixture of the above product, methanol (50 ml), 6N hydrochloric acid (141 μl), and 10% palladium-on-carbon (37 mg) was shaken in a Parr hydrogenator (40 psi) for 24 hours. The catalyst was filtered and the filtrate was concentrated in vacuo. The residue was dissolved in ethyl acetate and washed with aqueous sodium bicarbonate, and the organic layer was dried and concentrated. The product was purified by chromatography over silica gel (methylene chloride/methanol) to give $N_\delta$-Boc-$N_\alpha$-methylornithine 3-phenylpropylamide.

A cold solution (0° C.) of N-Boc-homophenylalanine (221 mg), diisopropylethylamine (228 μl), and anhydrous tetrahydrofuran (4 ml) was treated with PyBrop (398 mg), followed by the addition of a solution of $N_\delta$-Boc-$N_\alpha$-methylornithine 3-phenylpropylamide (228 mg) in tetrahydrofuran (3 ml). The resulting solution was stirred for overnight. The precipitate was filtered and the solid was washed with ethyl acetate. The filtrate was concentrated in vacuo and the product purified by silica gel chromatography (hexane/ethyl acetate) to give N-Boc-homophenylalanyl-$N_\delta$-Boc-$N_\alpha$-methylornithine 3-phenylpropylamide (260 mg): $^1$H NMR (400 MHz, CDCl$_3$) δ1.43 (s, 18H), 1.7–2.0 (m, 8H), 2.58 (t, J=6.4 Hz, 2H), 2.6–2.85 (m, 5H), 3.0–3.4 (m, 4H), 4.4–4.5 (m, 1H), 4.9–5.0 (m, 1H), and 7.1–7.3 (m, 10H).

The above product was treated with trifluoroacetic acid (2 ml) for 30 min. The solution was concentrated in vacuo and the residue was purified by reverse phase HPLC (Amberchrome) with acetonitrile/0.1% aqueous trifluoroacetic acid as the eluent. The desired fraction was lyophilized to give homophenylalanyl-$N_\alpha$-methylornithine 3-phenylpropylamide: $^1$H-NMR (400 MHz, D$_2$O) δ1.6–2.0 (m, 8H), 2.58 (t, J=6.8 Hz, 2H), 2.6–2.8 (m, 5H), 3.15 (t, J=7.2 Hz, 2H), 3.30–3.35 (m, 2H), 4.15–4.20 (m, 1H), 5.05–5.10 (m, 1H), and 7.05–7.3 (m, 10H); mass spectrum, m/e 425 (M$^+$), 290, 264, and 129.

Example 60
Homophenylalanyl-N$_\alpha$-Methylornithine-3-(4-Methylphenyl)propylamide Trifluoroacetate This was similarly prepared, as described in Example 59, with N-Boc-homophenylalanine, N$_\alpha$-benzyl-N$_\delta$-Boc-N$_\alpha$-methylornithine, and 3-(4-methylphenyl)propylamine used as starting materials: $^1$H NMR (400 MHz, D$_2$O) δ1.40–1.75 (m, 6H), 1.9–2.1 (m, 2H), 2.2 (s, 3H), 2.48 (t, J=6.8 Hz, 2H), 2.6–2.8 (m, 5H), 3.05–3.15 (m, 2H), 3.22–3.30 (m, 2H), 4.15–4.20 (m, 1H), 4.95–5.00 (m, 1H), and 6.9–7.2 (m, 9H); mass spectru, m/e 439 (M$^+$), 290, 278, 261, and 129.

Example 61
Homophenylalanyl-N$_\alpha$-Methylornithine 3-(4-Methoxyphenyl)propyl-amide Trifluoroacetate This was similarly prepared, as described in Example 59, with N-Boc-homophenylalanine, N$_\alpha$-benzyl-N$_\delta$-Boc-N$_\alpha$-methylornithine, and 3-(4-methoxyphenyl)propylamine used as starting materials: $^1$H NMR (400 MHz, D$_2$O) δ1.6–2.0 (m, 6H), 2.05–2.15 (m, 2H), 2.6 (t, J=6.8 Hz, 2H), 2.8 (t, J=7.2 Hz, 2H), 3.0 (s, 3H), 3.05 (t, J=7.2 Hz, 2H), 3.15–3.40 (m, 2H), 3.85 (s, 3H), 4.60–4.65 (m, 1H), 4.95–5.05 (m, 1H), 6.93 (d, J=7.2 Hz, 2H), 7.15 (d, J=7.2 Hz, 2H), and 7.25–7.45 (m, 5H); mass spectrum, m/e 455 (M$^+$), 294, 290, 277, and 129.

Example 62
Homophenylalanyl-N$_\alpha$-Methylornithine 3-(4-fluorophenyl)propylamide Trifluoroacetate This was similarly prepared, as described in Example 59, with N-Boc-homophenylalanine, N$_\alpha$-benzyl-N$_\delta$-Boc-N$_\alpha$-methylornithine, and 3-(4-fluorophenyl)propylamine used as starting materials: $^1$H NMR (400 MHz, D$_2$O) δ1.65–2.0 (m, 6H), 2.1–2.3 (m, 2H), 2.6 (t, J=6.8 Hz, 2H), 2.8 (t, J=6.8 Hz, 2H), 3.0 (s, 3H), 3.05 (t, J=6.8 Hz, 2H), 3.15–3.40 (m, 2H), 4.55–4.65 (m, 1H), 4.95–5.05 (m, 1H), and 7.05–7.45 (m, 9H); mass spectrum, m/e 443 (M$^+$), 313, 290, 282, and 129.

Example 63
Glycyl-N$_\alpha$-Methylornithine 2-(Cyclohexyl)ethylamide Trifluoroacetate This was similarly prepared, as described in Example 59, with Boc-glycine, N$_\alpha$-benzyl-N$_\delta$-Boc-N$_\alpha$-methylornithine, and 2-(cyclohexyl)ethylamine used as starting materials: mass spectrum, m/e 313 (M$^+$), 295, 356, 239, 186, and 129.

Example 64
β-(Cyclohexyl)alanyl-N$_\alpha$-Methylornithine 2-Phenethylamide Trifluoroacetate This was similarly prepared, as described in Example 59, with Boc-β-(cyclohexyl)alanine, N$_\alpha$-benzyl-N$_\delta$-Boc-N$_\alpha$-methylornithine, and 2-phenethylamine used as starting materials and Boc-β-(cyclohexyl)alanine were used: $^1$H NMR (400 MHz, D$_2$O) δ1.2–2.0 (m,17H), 2.8–3.0 (m, 5H), 3.0–3.1 (m, 2H), 3.5–3.7 (m, 2H), 4.4–4.5 (m, 1H), 4.8–4.9 (m, 1H), and 7.3–7.5 (m, 5H); mass spectrum, m/e 403 (M$^+$), 381, 282, 250, and 129.

Example 65
Leucyl-N$_\alpha$-Methylornithine 2-Naphthylamide Trifluoroacetate A mixture of N$_\alpha$-benzyl-N$_\delta$-Boc-N$_\alpha$-methylornithine (2.13 g, 6.3 mmol), diisopropyl-ethylamine (2.2 ml, 12.6 mmol), and anhydrous tetrahydrofuran (20 ml) was treated with PyBop (4 g, 7.6 mmol) at 0° C. for 10 min., followed by the addition of β-amino-naphthalene (1.09 g, 7.6 mmol). The resulting solution was stirred at ambient temperature overnight, and the reaction mixture was diluted with ethyl acetate and washed with water. The organic layer was dried over anhydrous sodium sulfate and concentrated in vacuo. The product was purified by silica gel chromatography (hexane/ethyl acetate) to afford N$_\alpha$-benzyl-N$_\delta$-Boc-N$_\alpha$-methylornithine 2-naphthyl-amide (2 g): $^1$H NMR (400 MHz, CDCl$_3$) δ1.43 (s, 9H), 1.6–1.9 (m, 4H), 2.38 (s, 3H), 3.2–3.3 (m, 2H), 3.7–3.8 (m, 2H), 4.7 (s, 1H), 7.25–7.8 (m, 11H), and 8.25 (s, 1H).

A mixture of the above product, methanol (60 ml), 6N hydrochloric acid (723 µl, 4.3 mmol), and 10% palladium-on-carbon (200 mg) was shaken in Parr hydrogenator (40 psi) for 24 hours. The catalyst was removed by filtration and the filtrate was concentrated in vacuo. The residue was dissolved in ethyl acetate and washed with aqueous sodium bicarbonate. The organic layer was dried and concentrated. The product was purified by chromatography with CH$_2$Cl$_2$/CH$_3$OH as the eluent to give N$_\delta$-Boc-N$_\alpha$-methylornithine 2-naphthylamide (1 g): $^1$H NMR (400 MHz, CDCl$_3$) δ1.4 (s, 9H), 1.6–1.8 (m, 2H), 2.0–2.2 (m, 2H), 2.45 (s, 3H), 3.1–3.3 (m, 2H), 4.1–4.3 (m, 1H), 5.0 (s, 1H), 7.4–7.5 (m, 2H), 7.7–7.8 (m, 4H), and 8.4 (s, 1H).

N$_\delta$-Boc-N$_\alpha$-methylornithine 2-naphthylamide (149 mg, 0.40 mmol), N-Boc-leucine N-hydroxysuccinimide ester (166 mg, 0.5 mmol) and dimethylformamide (3 ml) was stirred overnight at 70° C. After cooling, the mixture was diluted with ethyl acetate and washed with water. The organic layer was dried over anhydrous sodium sulfate and concentrated. The product was purified by chromatography (silica gel—hexane/ethyl acetate) to give N-Boc-leucyl-N$_\delta$-Boc-N$_\alpha$-methylornithine 2-naphthylamide (44 mg): $^1$H NMR (400 MHz, CDCl$_3$) δ0.9–1.0 (m, 6H), 1.4–1.8 (m, 25H), 3.05 (s, 3H), 3.1–3.2 (m, 2H), 4.6–4.7 (m, 1H), 5.1–5.2 (m, 1H), 7.3–7.5 (m, 2H), 7.7–7.8 (m, 4H), and 8.1 (s, 1H).

N-Boc-leucyl-N$_\delta$-Boc-N$_\alpha$-methylornithine 2-naphthylamide was treated with TFA at 25° C. for 30 min. The solution was concentrated in vacuo and the residue purified by reverse phase HPLC (Amberchrome—CH$_3$CN/0.1% TFA—H$_2$O). The desired fraction was lyophilized to give titled product: $^1$H NMR (400 MHz, D$_2$O) δ1.0–1.1 (m, 6H), 1.7–1.9 (m, 5H), 2.0–2.2 (m, 2H), 3.1–3.3 (m, 5H), 4.6–4.7 (m, 1H), 5.1–5.2 (m, 1H), 7.5–7.7 (m, 3H), and 7.9–8.1 (m, 4H); mass spectrum, m/e 384 (M$^+$), 271, 241, 194, and 129.

Example 66
Glycyl-N$_\alpha$-(Phenethyl)ornithine 3-Phenylpropylamide Trifluoroacetate A solution of dicyclohexylcarbodiimide (4.68 g, 23 mmol) and ethyl acetate (100 ml) was added to a solution of N$_\alpha$-Fmoc-N$_\delta$-Boc-ornithine (10.3 g, 23 mmol) and pentafluorophenol (4.17 g, 23 mmol) in ethyl acetate (200 ml). The resulting mixture was stirred at 25° C. for 2 hours and the solid formed during reaction was removed by filtration. The filtrate was concentrated in vacuo to give the activated ester as a white solid. The activated ester (12.7 g, 20 mmol), 3-phenylpropylamine (2.76 g, 20 mmol), and dimethylformamide (100 ml) was stirred at 25° C. for 4 hours. The solution was then treated with piperidine (5 ml) for 1 hour at 25° C. and concentrated in vacuo. The residue was dissolved in ethyl acetate and washed with aqueous sodium bicarbonate. The organic layer was dried, concentrated, and purified by chromatography to give N$_\delta$-Boc-ornithine 3-phenylpropylamide (5 g): $^1$H NMR (400 MHz, CD$_3$OD) δ1.4 (s, 9H), 1.45–1.7 (m, 4H), 1.8–1.9 (m, 2H), 2.6 (t, J=6.4

Hz, 2H), 3.0–3.1 (m, 2H), 3.2–3.3 (m, 2H), 3.3–3.4 (m, 1H), and 7.1–7.3 (m, 5H).

A cold solution (0° C.) of the above amine (3 g, 8.6 mmol), in methanol (20 ml), was treated sequentially with acetic acid (345 µl, 6 mmol) and phenylacetaldehyde (1.2 ml, 10 mmol). Then a solution of sodium cyanoborohydride (2.7 g, 43 mmol) in methanol (10 ml) was added to the mixture slowly. The reaction was stirred for additional 30 minutes and the solvent was removed in vacuo. The residue was dissolved in ethyl acetate and washed with aqueous sodium bicarbonate, and purified by chromatography (silica gel, hexane/ethyl acetate) to afford $N_\alpha$-(phenethyl)ornithine 3-phenylpropylamide (2.64 g): $^1$H NMR (400 MHz, $CD_3OD$) δ1.4 (s, 9H), 1.45–1.8 (m, 6H), 2.6 (t, J=6.4 Hz, 2H), 2.65–2.8 (m, 4H), 3.02–3.2 (m, 5H), and 7.1–7.3 (m, 10H).

cold solution (0° C.) of Boc-glycine (543 mg, 3.1 mmol), diisopropylethylamine (1 ml, 6.2 mmol), and tetrahydrofuran (10 ml) was treated with PyBrop (1.45 g, 3.1 mmol), followed by the addition of $N_\alpha$-phenethyl-$N_\delta$-Boc-ornithine 3-phenylpropylamide (1.28 g, 2.8 mmol) in tetrahydrofuran (5 ml). The resulting solution was acetate. The filtrate was concentrated in vacuo and the product purified by chromatography (silica gel—hexane/ethyl acetate) to give N-Boc-glycyl-$N_\alpha$-phenethyl-$N_\delta$-Boc-ornithine 3-phenylpropylamide (1.2 g).

The above product was treated with trifluoroacetic acid (5 ml) for 30 min and the solution was concentrated in vacuo. The residue was purified by reverse phase HPLC (Amberchrome—$CH_3CN$/0.1% TFA-$D_2O$) and the desired fraction was lyophilized to give desired product: $^1$H NMR (400 MHz, $D_2O$) δ1.6–2.0 (m, 6H), 2.5–2.6 (m, 2H), 2.8–3.0 (m, 4H), 3.05–3.15 (m, 2H), 3.4–3.5 (m, 2H), 3.7–3.9 (m, 2H), 4.5–4.6 (m, 1H), and 7.1–7.4 (m, 10H); mass spectrum, m/e 411 ($M^+$), 393, 354, 336, 276, and 219.

Example 67
Glycyl-$N_\alpha$-(Phenethyl)ornithine 2-Naphthylamide Trifluoroacetate This was similarly prepared, as described in Example 66, except β-aminonaphthalene was used as the starting material: $^1$H NMR (400 MHz, $D_2O$) δ1.7–2.2 (m, 4H), 3.0–3.2 (m, 6H), 3.8–4.0 (m, 2H), 5.0–5.1 (m, 1H), and 7.3–6,25 (m, 12H); mass spectrum, m/e 419 ($M^+$), 401, 298, 276, 258, and 219.

Example 68
Glycyl-$N_\alpha$-(Phenethyl)ornithine Quinoline-3-amide Trifluoroacetate This was similarly prepared, as described in Example 66, except 3-aminoquinoline was used as the starting material: $^1$H NMR (400 MHz, $D_2O$) 67 1.7–2.3 (m, 4H), 3.0–3.3 (m, 4H), 3.7–3.9 (m, 2H), 3.9–4.1 (m, 2H), 5.0–5.1 (t, J=6.4 Hz, 7.3–7.5 (m, 5H), 7.8–8.2 (m, 4H), 8.8 (s, 1H), and 9.1 (s, 1H); mass spectrum m/e 420 ($M^+$), 363, 346, 219, 174, and 145.

Example 69
β-Alanyl-$N_\alpha$-(Phenethyl)ornithine Phenylpropylamide Trifluoroacetate This was similarly prepared, as described in Example 66, exceptn β-Boc-alanine was used as the acylating reagent: $^1$H NMR (400 MHz, $D_2O$) δ1.6–2.1 (m, 6H), 2.7 (t, J=6.4 Hz, 2H), 2.8–3.1 (m, 6H), 3.25–3.4 (m, 4H), 3.6–3.7 (m, 2H), 4.6–4.7 (m, 1H), and 7.3–7.5 (m, 10H); mass spectrum, m/e 425 ($M^+$), 290, 219, 174, and 105.

Example 70
Glycyl-$N_\alpha$-(2-Hydroxyphenethyl)ornithine 3-Phenylpropylamide Trifluoroacetate This was similarly prepared, as described in Example 66, except (2-hydroxyphenyl)acetaldehyde was used in the reductive amination step: $^1$H NMR (400 MHz, $D_2O$) δ1.6–2.0 (m, 6H), 2.6 (t, J=6.4 Hz, 2H), 2.8–3.0 (m, 4H), 3.05–3.15 (m, 2H), 3.4–3.6 (m, 2H), 3.9–4.0 (m, 2H), 4.5–4.6 (m, 1H), and 6.8–7.3 (m, 9H); mass spectrum, m/e 427 ($M^+$), 370, 353, 292, 235, 174, and 190.

Example 71
Glycyl-$N_\alpha$-(iso-Amyl)ornithine 3-Phenylpropylamide Trifluoroacetate This was similarly prepared, as described in Example 66, except isovaleraldehyde was used in the reductive amination step: $^1$H NMR (400 MHz, $D_2O$) δ0.95 (d, J=6.8 Hz, 6H), 1.5–2.0 (m, 9H), 2.7 (t, J=6.4 Hz, 2H), 3.0–3.2 (m, 2H), 3.25–3.45 (m, 4H), 4.0–4.2 (m, 2H), 4.6 (t, J=6.4 Hz, 1H), and 7.3–7.5 (m, 5H); mass spectrum, m/e 377 ($M^+$), 359, 320, 242, 185, and 140.

Example 72
Glycyl-$N_\alpha$-(2-Benzo[b]furanylmethyl)ornithine 3-Phenylpropylamide Trifluoroaetate This was similarly prepared, as described in Example 66, except benzo[b]furan-2-carboxaldehyde was used in the reductive amination step: $^1$H NMR (400 MHz, $D_2O$) δ1.5–2.1 (m, 6H), 2.5 (t, J=6.4 Hz, 2H), 2.8–3.2 (m, 6H), 4.2–4.4 (m, 2H), 6.9 (s, 1H), and 7.2–7.8 (m, 9H); mass spectrum, m/e 437 ($M^+$), 380, 302, 245, and 131.

Example 73
Glycyl-$N_\alpha$-(3-Quinolinylmethyl)ornithine 3-Phenylpropylamide Trifluoroacetate This was similarly prepared, as in Example 66, except quinoline-3-carboxaldehyde was used in the reductive amination step: $^1$H NMR (400 MHz, $D_2O$) 67 1.2–2.0 (m, 6H), 2.2–2.4 (m, 2H), 2.6–2.8 (m, 2H), 3.0–3.2 (m, 2H), 4.1–4.4 (m, 1H), 7.0–7.1 (m, 2H), 7.2–7.4 (m, 3H), 7.9–8.2 (m, 4H), 8.9 (s, 1H), an mass spectrum, m/e 448 ($M^+$), 430, 391, 313, and 256.

Example 74
Glycyl-N-(Phenethyl)ornithine 5-Indanylamide Trifluoroacetate

This was similarly prepared, as described in Example 66, except 5-aminoindan was used as a starting material: $^1$H NMR (400 MHz, $D_2O$) 67 1.7–2.3 (m, 6H), 2.9–3.2 (m, 8H), 3.7–4.0 (m, 4H), 5.0 (t, J=6.4 Hz, 1H), and 7.2–7.5 (m, 8H).

Example 75
Glycyl-$N_\alpha$-(Phenethyl)lysine 3-Phenylpropylamide Trifuoroacetate This was similarly prepared, as described in Example 66, except $N_\alpha$-Boc-$N_\epsilon$-Cbz-lysine was used as a starting material: $^1$H NMR (400 MHz, $CD_3OD$) δ1.5–2.1 (m, 8H), 2.6 (t, J=6.4 Hz, 2H), 2.8–3.0 (m, 4H), 3.2–3.4 (m, 2H), 3.5–3.6 (m, 2H), 3.7–3.9 (m, 2H), 4.7–4.8 (m, 1H), and 7.1–7.3 (m, 10H); mass spectrum, m/e 453 ($M^+$), 354, 300, 247, and 219.

Example 76
β-Alanyl-$N_\alpha$-(Phenethyl)lysine 3-Phenylpropylamide Trifluoroacetate Similarly prepared, as described in Example 66, except $N_\alpha$-Boc-$N_\epsilon$-Cbz-lysine and β-Boc-alanine were used as starting materials: $^1$H NMR (400 MHz, $D_2O$) 67 1.3–1.5 (m, 2H), 1.7–2.0 (m, 6H), 2.65 (t, J=6.4 Hz, 2H), 2.8–3.0 (m, 4H), 3.0–3.1 (m, 2H), 3.2–3.4 (m, 4H), 3.7–3.9 (m, 2H), 4.8–4.9 (m, 1H), and 7.2–7.5 (m, 10); mass spectrum, m/e 440 (M$^+$+1), 368, 304, 233, and 188.

Example 77
Glycyl-N$_\alpha$-Phenethyl)diaminobutyric acid 3-Phenylpropylamide Trifluoroacetate This was similarly prepared, as described in Example 66, except N$_\alpha$-Cbz-N$_\gamma$-Boc-L-diaminobutyric acid was used as the starting material: $^1$H NMR (400 MHz, D$_2$O) δ1.8–2.0 (m, 2H), 2.1–2.4 (m, 2H), 2.7 (t, J=6.4 Hz, 2H), 2.9–3.1 (m, 4H), 3.2–3.4 (m, 2H), 3.6–3.8 (m, 2H), 3.9–4.1 (m, 2H), 4.7–4.8 (m, 1H), and 7.2–7.5 (m, 10H); mass spectrum, m/e 397 (M$^+$), 379, 276, 242, and 205.

Example 78
β-Alanyl-N$_\alpha$-Phenethyl)diaminobutyric acid 3-Phenylpropylamide Trifluoroacetate This was similarly prepared, as described in Example 66, except N$_\alpha$-Cbz-N$_\gamma$-Boc-L-diaminobutyric acid and β-Boc-alanine were used as starting materials: $^1$H NMR (400 MHz, D$_2$O) δ1.8–2.0 (m, 2H), 2.1–2.4 (m, 2H), 2.7 (t, J=6.4 Hz, 2H), 2.9–3.1 (m, 6H), 3.2–3.4 (m, 4H), 3.6–3.7 (m, 2H), 4.7–4.8 (m, 1H), and 7.2–7.5 (m, 10H); mass spectrum, m/e 411 (M$^+$), 393, 340, 276, and 205.

Example 79
4-Aminobutyryl-N$_\alpha$-(Phenethyl)diaminopropionic acid 3-Phenylpropyl-amide Trifluoroacetate This was similarly prepared, as described in Example 66, except N$_\alpha$-Cbz-N$_\beta$-Boc-L-diaminopropionic acid and N$_\gamma$-Boc-aminobutyric acid were used as starting materials: $^1$H NMR (400 MHz, D$_2$O) δ1.7–1.9 (m, 4H), 2.4–2.6 (m, 4H), 2.8–3.0 (m 4H), 3.1–3.3 (m, 4H), 3.5–3.7 (m, 2H), 4.2–4.3 (m, 1H), and 7.2–7.4 (m, 10H).

Example 80
4-Aminobutyryl-N$_\alpha$-(Phenethyl)diaminopropionic Acid Quinoline-3-amide Trifuoroacetate This was similarly prepared as described in Example 66, except N$_\alpha$-Cbz-N$_\beta$-Boc-L-diaminopropionic acid, 3-aminoquinoline, and N$_\gamma$-Boc-aminobutyric acid were used as starting materials: $^1$H NMR (400 MHz, D$_2$O) δ1.9–2.1 (m, 2H), 2.6–2.9 (m, 2H), 3.0–3.2 (m, 4H), 3.4–3.5 (m, 1H), 3.8–4.0 (m, 3H), 4.8–4.9 (m, 1H), 7.2–7.4 (m, 5H), 8.0 (t, J=7.2 Hz, 1H), 8.4 (t, J=7.2 Hz, 1H), 8.3 (t, J=7.2 Hz, 2H), 9.05 (s, 1H), and 9.4 (s, 1H); mass spectrum, m/e 420 (M$^+$), 402, 335, 299, and 270.

Example 81
Acetimidoylglycyl-N$_\alpha$-(Phenethyl)ornithine 3-Phenylpropylamide Trifluoroacetate Glycyl-N$_\alpha$-(phenethyl)ornithine 3-phenylpropylamide trifluoroacetate was treated with ethyl acetimidate in ethanol at pH9 and the product was purified by HPLC: $^1$H NMR (400 MHz, D$_2$O) δ1.6–2.0 (m, 6H), 2.3 (s, 3H), 2.7 (t, J=6.4 Hz, 2H), 2.9–3.1 (m, 4H), 3.2–3.4 (m, 2H), 3.5–3.7 (m, 2H), 4.1–4.3 (m, 2H), 4.7–4.8 (m, 1H), and 7.2–7.5 (m, 10H); mass spectrum, m/e 453 (M$^+$), 354, 300, 247, and 219.

Example 82
Homophenylalanine N-(3-Aminopropyl)-3-Phenylpropylamide Trifluoroacetate A mixture of 3-phenylpropylamine (0.95 g, 7 mmol) and acrylonitrile (0.55 ml, 8.4 mmol) in ethanol (30 ml) was refluxed for 2 hours to give N-(2-cyanoethyl)-3-phenyl-propylamine.

A solution of Boc-homophenylalanine (136 mg, 0.49 mmol), diisopropylethylamine (169 μl mg, 0.97 mmol), and tetrahydrofuran (3 ml) was treated with PyBrop (248 mg, 0.63 mmol) at 0° C. (2-cyanoethyl)-3-phenylpropylamine (109 mg, 0.58 mmol) in tetrahydrofuran (2 ml) was added dropwise and the reaction mixture was stirred overnight. The solid was filtered and rinsed with ethyl acetate, and the filtrate was concentrated and purified by chromatography to give Boc-homophenylalanine (2-cyanoethyl)-3-phenylpropylamide. A mixture of above product (200 mg), 10% palladium-on-carbon (20 mg), and methanol (40 ml) was hydrogenated on a Parr hydrogenator (40 psi) overnight. The catalyst was removed by filtration through Celite and the filtrate was concentrated in vacuo. The residue was then treated with trifluoroacetic acid for 30 min. The solvent was removed in vacuo and the product was purified by reverse phase HPLC to give white solid: $^1$H NMR (400 MHz, D$_2$O) δ1.8–2.1 (m, 6H), 2.5–2.8 (m, 4H), 3.0–3.3 (m, 4H), 3.3–3.7 (m, 2H), 4.0–4.1 (m, 1H), and 7.3–7.5 (m, 10H).

Example 83
β-(Cyclohexyl)alanyl N-(3-Aminopropyl)-3-(Cyclohexyl) propylamide Trifluoroacetate A suspension of homophenylalanine N-(3-aminopropyl)-3-phenylpropylamide (100 mg), platinum dioxide (10 mg), 6N hydrochloric acid (0.1 ml), and 20 ml of methanol was hydrogenated in a Parr hydrogenator (40 psi) for 24 hours. The catalyst was removed by filtration and the product purified by reverse phase HPLC to give titled compound: $^1$H NMR (400 MHz, D$_2$O) δ0.9–1.05 (m, 4H), 1.1–1.4 (m, 13H), 1.6–1.8 (m, 12H), 1.9–2.1 (m, 3H), 3.05–3.15 (m, 2H), 3.4–3.7 (m, 4H), and 4.4–4.5 (m, 1H); mass spectrum, m/e 366 (M$^+$), 349, 225, 199, and 182.

Example 84
Homophenylalanyl-N-(3Aminopropyl)aminoethyl 2-Naphtyl Ether Trifluoroacetate This was similarly prepared, as described in Example 82, except (2-naphthoxy)ethyl-amine was used as a starting material: $^1$H NMR (400 MHz, D$_2$O) δ1.9–2.0 (m, 2H), 2.2–2.4 (m, 2H), 2.6–2.8 (m, 2H), 2.9–3.1 (m, 2H), 3.4–3.6 (m, 2H), 3.6–3.8 (m, 2H), 4.2–4.4 (m, 2H), 4.5–4.6 (m, 1H), and 6.9–7.9 (m, 12H).

Example 85
Homophenylalanyl-Ornithinyl-2-Phenethyl Thioether Trifluoroacetate A well, stirred cold solution (0° C.) of N$_\alpha$-Boc-N$_\delta$-Cbz-ornithine (5 g, 13.6 mmol), diisopropylethylamine (5.9 ml, 34 mmol), and tetrahydrofuran (60 ml) was treated with ethyl chloroformate (3.25 ml, 34 mmol) at 0° C. Sodium borohydride (2.58 g, 68 mmol) was added, followed by the slow addition of 1:1-tetrahydrofuran/water (10 ml) 30 minutes later. The reaction mixture was acidified with 6N hydrochloric acid and the solution was extracted with dichloromethane. The organic layer was dried over anhydrous sodium sulfate and purified by chromatography to give N$_\alpha$-Boc-N$_\delta$-Cbz-ornithinol (3.9 g): $^1$H NMR (400 MHz, CDCl$_3$) δ1.2–1.4 (m, 13H), 3.0 (t, J=6.4 Hz, 2H), 3.4 (s, 2H), 3.8 (s, 1H), 4.95 (s, 2H), and 7.1–7.2 (m, 5H).

Diethyl azodicarboxylate (180 μl, 1.1 mmol) was added to a solution of triphenylphosphine (288 mg, 1.1 mmol) in tetrahydrofuran (3 ml) at 0° C. and the mixture was further stirred for 30 min. at 0° C. A solution of N$_\alpha$-Boc-N$_\beta$-Cbz-ornithinol (200 mg, 0.57 mmol), thioacetic acid (86 μl, 1.1 mmol), and tetrahydrofuran (2 ml) was added and the mixture was then stirred at 25° C. for 3 hours. The reaction solution was diluted with ethyl acetate and washed with aqueous sodium bicarbonate. The product was purified by chromatography to give $N_\alpha$-Boc-$N_\delta$-Cbz-ornithinethiol S-acetate (189 mg) which in tetrahydrofuran (3 ml) was reacted with 0.5N sodium methoxide (2 ml) at 25° C. for 4 hours. The resulting solution was treated with (2-iodoethyl) benzene (320 mg, 1.4 mmol) and was stirred for overnight. The reaction solution was diluted with ethyl acetate, washed with water, and purified by chromatography to give $N_\alpha$-Boc-$N_\delta$-Cbz-ornithinyl 2-phenethyl thioether (160 mg): $^1$H NMR (400 MHz, CDCl$_3$) δ1.4–1.7 (m, 13H), 2.6–2.9 (m, 6H), 3.1–3.3 (m, 2H) 3.7 (s, 1H), 5.1 (s, 2H), and 7.2–7.4 (m, 10H).

The above product was treated sequentially with trifluoroacetic acid to remove the Boc group, followed by PyBrop-mediated acylation with Boc-homophenylalanine to give Boc-homophenylalanyl-$N_\delta$-Cbz-ornithinyl 2-phenethyl thioether. Protecting groups were removed sequentially -i) catalytic hydrogenation and ii) trifluoroacetic acid to give homophenylalanyl-ornithinyl 2-phenethyl thioether trifluoroacetate: $^1$H NMR (400 MHz, DMSO) δ1.3–1.6 (m, 4H), 1.9–2.0 (m, 2H), 2.6–2.8 (m, 10H), 3.7– 3.9 (m, 2H), and 7.1–7.3 (m, 10H); mass spectrum, m/e 400 (M$^+$), 383, 319, 239, 222, and 200.

Example 86
Phenylalanyl-4-Ornithinyl 2-Naphthyl Thioether Trifluoroacetate (A) $N_\alpha$-Boc-$N_\delta$-Cbz-Ornithinol Methanesulfonate A solution of $N_\alpha$-Boc-$N_\delta$-Cbz-ornithinol (363 mg) in dichloromethane (10 ml) at 0° C., under nitrogen atmosphere, was treated sequentially with methanesulfonyl chloride (110 μl, 1.4 eq) and triethylamine (200 μl, 1.4 eq). After 3 hrs, the solution was poured into dichloromethane and worked up as usual. The crude product, which is very pure (400 mg), is a white solid: $^1$H NMR (400 MHz, CDCl$_3$) δ1.45 (s, 9H), 1.63 (m, 4H), 3.02 (s, 3H), 3.24 (m, 2H), 3.84 (m, 1H), 4.19 (dd, J=9.5; 3.7 Hz, 1H), 4.23 (d, J=9.5 Hz, 1H), 5.14 (s, 2H), and 7.39 (m, 5H).

(B) $N_\alpha$-Boc-$N_\beta$-Cbz-ornithinyl 2-Naphthyl Thioether

A solution of $N_\alpha$-Boc-$N_\delta$-Cbz-ornithinol methanesulfonate (A) (100 mg) in dimethylformamide (2.5 ml), is added sodium iodide (71 mg), 2-naphthalenethiol (66 mg) and diisopropylethylamine (85 μl) was maintained at 70° C. for 12 h. After cooling to room temperature, the reaction mixture was poured into ethyl acetate and worked up as usual. After chromatography (10 to 30 % ethyl acetate/ hexane), there was obtained intermediate (B) (60 mg) as a white solid: $^1$H NMR (400 MHz, CDCl$_3$) δ1.41 (s, 9H), 1.42–1.78 (m, 4H), 3.19 (m, 4H), 3.86 (m, 1H), 5.13 (s, 2H), 7.38 (m, 5H), 7.44 (m, 3H), 7.75 (d, J=1 1.3 Hz, 2H), 7.80 (d, J=10.1 Hz, 1H), and 7.85 (s, 1H).

(C) Boc-Phenylalanyl-$N_\delta$-Cbz-ornithinyl 2-Naphthyl Thioether

A solution of $N_\alpha$-Boc-$N_\delta$-Cbz-ornithinyl 2-naphthyl thioether (B) (60 mg) and 4M hydrochloric acid/ dioxane (3 ml) was stirred at 25° C. for 1.5 h and concentrated in vacuo. The crude residue was coupled to Boc-phenylalanine by Procedure C, followed by silica gel chromatography (20 to 30%-ethyl acetate/hexane) to give a glassy solid (73 mg).

(D) Phenylalanyl-Ornithinyl 2-Naphthyl Thioether Trifluoroacetate

A solution of Boc-phenylalanyl-$N_\delta$-Cbz-ornithinyl 2-naphthyl thioether (C) (30 mg) and a mixture of trifluoroacetic acid-triethylsilane (3:1) (10 ml) was stirred at 25° C. for 1 hr and concentrated in vacuo. The crude material was purified by HPLC to afford desired product (10 mg) as a white solid: HPLC (method A, retention time=46.26 min); $^1$H NMR (400 MHz, D$_2$O) δ1.69 (m, 2H), 1.77 (m, 1H), 1.87 (m, 1H), 2.84 (t, J=8.4, 2H), 3.02 (m, 2H), 3.09 (dd, J=14.4; 7.2 Hz, 1H), 3.22 (dd, J=14.0 5.2 Hz, 1H), 4.15 (t, J=8.0 Hz, 1H), 7.16 (m, 2H), 7.34 (m, 3H), 7.48 (m, 1H), 7.60 (m, 3H), 7.93 (t, J=7.2, 1H), and 7.97 (m, 2H).

Example 87
Homophenylalanyl-Ornithinyl 2-Benzothiazolyl Thioether Trifluoroacetate (A) $N_\alpha$-Boc-$N_\delta$-Cbz-Ornithinyl 2-Benzothiazolyl Thioether A solution of $N_\alpha$-Boc-$N_\delta$-Cbz-ornithinol methanesulfonate (100 mg), sodium iodide (70 mg), dimethylformamide (2.5 ml), 2-mercaptobenzothiazole (70 mg) and diisopropylethylamine (85 μl) was stirred at 70° C. for 12 h. After cooling to ambient temperature, the reaction mixture was poured into ethyl acetate and worked up. The crude material was chromatographed over silica gel (20 to 50 % ethyl acetate/hexane) to afford titled product (50 mg) as a white solid: $^1$H NMR (400 MHz, CDCl$_3$) δ1.39 (s, 9H), 1.58–1.69 (m, 4H), 3.22 (m, 2H), 3.54 (m, 2H), 3.99 (m, 1H), 5.12 (s, 2H), 7.23–7.42 (m, 1H), 7.77 (d, J=10.3 Hz, 1H), and 7.86 (d, J=9.7 Hz, 1H).

(B) Boc-Homophenylalanyl-$N_\delta$-Cbz-Ornithinyl 2-Benzothiazolyl Thioether

Coupling of $N_\delta$-Cbz-ornithinyl 2-benzothiazolyl thioether and Boc-homophenylalanine afforded a glassy solid: $^1$H NMR (400 MHz, CDCl$_3$) δ1.42 (s, 9H), 1.63–1.79 (m, 5H), 1.92 (m, 1H), 2.49 (m, 2H), 3.23 (m, 2H), 3.58 (broad, d, J=14.1 Hz, 1H), 3.70 (dd, J=13.5; 10.3 Hz, 1H), 4.01 (m, 1H), 4.30 (m, 1H), 5.12 (s, 2H), 6.97 (d, J=9.0 Hz, 1H), 7.18 (m, 2H), 7.29 (m, 5H), 7.37 (m, 3H), 7.48 (t, J=8.3 Hz, 1H), 7.73 (d, J=8.4 Hz, 1H), and 8.02 (m, 1H).

(C) Homophenylalanyl-Ornithinyl 2-Benzothiazolyl Thioether Trifluoroacetate

A solution of Boc-homophenylalanyl-$N_\delta$-Cbz-ornithinyl 2-benzothiazolyl thioether (B) (35 mg) and trifluoroacetic acid (10 ml) was kept at 25° C. for 2 hrs and concentrated in vacuo. After HPLC purification (method A, retention time=42.1 min), there was obtained a white solid (33 mg): $^1$H NMR (400 MHz, D$_2$O) δ1.78–1.90 (m, 4H), 2.04 (m, 2H), 2.62 (m, 2H), 3.11 (m, 2H), 3.44 (dd, J=13.3; 9.6 Hz, 1H), 3.79 (dd, J=13.0; 2.7 Hz, 1H), 4.06 (t, J=5.9 Hz, 1H), 4.41 (m, 1H), 7.03 (m, 2H), 7.24 (m, 3H), 7.42 (t, J=8.5 Hz, 1H), 7.55 (t, J=9.4 Hz, 1H), 7.81 (d, J=9.5 Hz, 1H), and 7.85 (d, J=8.6 Hz, 1H).

Example 88
D-Phenylalanyl-Ornithinyl 2-Benzothiazolyl Thioether Trifluoroacetate (A) Boc-D-Phenylalanyl-$N_\delta$-CBz-Ornithinyl 2-Benzothiazolyl Thioether This compound is prepared in two steps. $N_\alpha$-Boc-$N_\delta$-Cbz-ornithinyl 2-benzothiazolyl thioether (140 mg) is treated with 4M hydrochloric acid in dioxane (5 ml) for 20 min and concentrated in vacuo. The intermediate $N_\delta$-CBz-ornithinyl 2-benzothiazolyl thioether is dissolved in dimethylformamide (3 ml), diisopropylethylamine (50 μl) and Boc-phenylalanine N-hydroxysuccimide ester are added. After stirring 12 h, concentration and silica gel chromatography (1 to 2% methanol/CH$_2$Cl$_2$) afforded pure intermediate (129 mg): $^1$H NMR (400 MHz, CDCl$_3$) δ1.43 (s, 9H), 1.53 (m, 2H), 1.62 (m, 2H), 2.73 (m, 1H), 2.98 (dd, J=14.2; 7.7 Hz, 1H), 3.20 (m, 2H), 3.42 (m, 2H), 4.23 (m, 2H), 6.12 (s, 2H), 6.91 (m, 2H), 7.09 (m, 3H), 7.35 (m, 6H), 7.44 (t, J=10.6 Hz, 1H), 7.78 (d, J=9.1 Hz, 1H), and 7.90 (d, J=10.1 Hz, 1H).

(B) D-Phenylalanyl-Ornithinyl 2-Benzothiazolyl Thioether Trifluoroacetate

Boc-D-phenylalanyl-$N_\delta$-CBz-ornithinyl 2-benzothiazolyl thioether (A) was stirred at 25° C. with trifluoroacetic acid-triethylsilane (3:1–10 ml) for 2 hrs and concentrated in vacuo. The crude residue was purified by HPLC.(method C, retention time=49.57 min); $^1$H NMR (400 MHz, D$_2$O) δ1.46 (m, 3H), 1.74 (m, 1H), 2.98 (m, 2H), 3.22 (m, 2H), 3.40 (dd, J=13.6; 8.0 Hz, 1H), 3.66 (d, J=14.0 Hz, 1H), 4.17 (m, 2H), 7.30 (m, 2H), 7.44 (m, 3H), 7.52 (t, J=8.0 Hz, 1H), 7.62 (t, J=7.2 Hz, 1H), 7.94 (d, J=8.4 Hz, 1H), and 8.02 (d, J=8.4 Hz, 1H).

Example 89
4Fluorophenylalanyl-Ornithinyl 2-Benzimidazolyl Thioether Trifluoroacetate This was similarly prepared, as described in Example 86, except Boc-4-fluorophenyl-alanine and N$_δ$-CBz-ornithinyl 2-benzimidazolyl thioether were the starting materials.

Example 90
D-Ornithyl-D-phenylalaninyl 2Naphthyl Thioether Trifluoroacetate (A) N-Boc-D-Phenylalaninol Methanesulfonate A cold solution (0° C.) of N-Boc-D-phenylalaninol (0.53 g, 2.09 mmol) in anhydrous methylene chloride (20 mL) was treated sequentially with methanesulfonyl chloride (360 mg, 3.14 mmol) and triethylamine (0.32 g, 3.14 mmol). The reaction was stirred at 0° C. for 2 hr, quenched with 1M hydrochloric acid (2×25 mL) and extracted with methylene chloride. The combined extract was washed with saturated sodium bicarbonate (1×25 mL), and brine (1×25 mL). The organic layer was dried over anhydrous sodium sulfate, filtered and the filtrate adsorbed onto silica gel and applied to a column prepacked with silica gel. The title compound was eluted from the column with hexane:ethyl acetate (60:40, v:v) to furnish titled compound (352 mg) as a white solid.

(B) N-Boc-D-phenylalaninyl 2-Naphthyl Thioether

A mixture of N-Boc-D-phenylalaninol mesylate (0.3 g, 0.9 mmol), dimethylformamide (10 mL), 2-napthalenethiol (0.22 g, 1.39 mmol), diisopropylethylamine (1.39 mmol) and sodium iodide (0.14 g, 0.93 mmol) was kept at 80° C. for 18 hr, cooled to room temperature and methylene chloride (25 ml) was added. This mixture was washed with water (2×10 mL), 1 M sodium hydroxide (3×10 mL) and brine (2×15 mL). The organic layer was dried over anhydrous sodium sulfate, filtered and the filtrate adsorbed onto silica gel and applied to a column prepacked with silica gel. The title compound (121 mg) was eluted with hexane:ethyl acetate (90:10, v:v) to afford a white solid.

(C) D-Ornithyl-D-phenylalaninyl 2-Naphthyl Thioether Trifluoroacetate

N-Boc-D-phenylalaninyl 2-naphthyl thioether was deprotected (Procedure E) to afford D-phenylalaninyl 2-naphthyl thioether trifluoroacetate which was coupled (Procedure B) with N$_α$,N$_δ$-bis-Boc-ornithine. The N$_α$,N$_δ$-bis-Boc-ornithyl-D-phenylalaninyl 2-naphthyl thioether was deprotected by exposure to trifluoroacetic acid to afford after HPLC purification the titled compound: $^1$H NMR (400 MHz, D$_2$O) δ1.60–1.70 (4H), 2.64–2.70 (2H), 2.90–3.30 (3H), 3.41–3.50 (1H), 3.80–3.82 (1H), 4.39–4.41 (1H), 7.23–7.70 (8H), and 7.80–8.05 (4H); mass spectrum (relative intensity) m/e 408 (100, M+1).

Example 91
D-Lysyl-D-Leucinyl 2-Benzothiazolyl Thioether Trifluoroacetate

This was similarly prepared, as described in Example 90, except N$_α$,N$_ε$-bis-Boc-D-lysine and D-leucinyl 2-benzothiazolyl thioether were used.

Example 92
D-(3-Chlorotyrosyl)-D-Phenylalaninyl 2-Benzimidazolyl Thioether Trifluoroacetate This was similarly prepared, as described in Example 90, except Boc-D-3-chlorotyrosine and D-phenylalaninyl 2-benzimidazolyl thioether were used.

Example 93
D-β-(4-Pyridyl)alanyl-D-Methioninyl 3,4-Dimethoxyphenyl Thioether Trifluoroacetate This was similarly prepared, as described in Example 90, except Boc-D-β-(4-pyridyl)-alanine and D-methioninyl 3,4-dimethoxyphenyl thioether were used.

Example 94
D-Ornithyl-D-Cysteinyl 2-Benzimidazolyl Thioether Trifluoroacetate This was similarly prepared, as described in Example 90, except N$_α$,N$_δ$-bis-Boc-D-ornithine and D-cysteinyl 2-benzimidazolyl thioether were used.

Example 95
Homophenylalanyl-Ornithinyl 2-Naphthyl Ether Trifluoroacetate (A) N$_α$-Boc-N$_δ$-Cbz-Ornithinol This was prepared from N$_α$-Boc-N$_δ$-Cbz-ornithine using Procedure F: $^1$H NMR (400 MHz, CDCl$_3$) δ1.43 (broad s, 10H), 1.57 (m, 3H), 3.21 (m, 2H), 3.53–3.66 (m, 3H), 5.09 (s, 2H), and 7.38 (m, 5H).

(B) N$_α$-Boc-N$_δ$-Cbz-Ornithinyl 2-Naphthyl Ether

Solution of N$_α$-Boc-N$_δ$-Cbz-ornithinol (587 mg), dichloromethane (17 ml), 2-naphthol (288 mg), triphenylphosphine (524 mg) and N,N'-diisopropylazodicarboxamide (393 μl) was stirred for 12 hrs at 25° C., under nitrogen. The reaction mixture was poured into dichloromethane and washed successively with saturated sodium bicarbonate and brine. The organic phase was then dried over anhydrous sodium sulfate and concentrated in vacuo. Further purification by flash chromatography gave the titled product (534 mg) as a glassy solid: $^1$H NMR (400 MHz, CDCl$_3$) δ1.41 (s, 9H), 1.60–1.73 (m, 4H), 3.20 (m, 2H), 4.01 (m, 3H), 5.07 (s, 2H), 7.09 (s, 1H), 7.11 (d, J=8.3 Hz, 1H), 7.28 (m, 6H), 7.40 (t, J=8.4 Hz, 1H), and 7.71 (m, 3H).

(C) Boc-Homophenylalanyl-N$_δ$-Cbz-Ornithinyl 2-Naphthyl Ether

Solution of N$_α$-Boc-N$_δ$-Cbz-ornithinyl 2-naphthyl ether (273 mg) and 4M hydrochloric acid/dioxane (3 ml) was stirred at room temperature for 1.5 h and then concentrated in vacuo. The crude residue is coupled to Boc-homophenylalanine as per Procedure C, followed by flash chromatography (40% ethyl acetate/hexane) to give desired product (130 mg) as a glassy solid: $^1$H NMR (400 MHz, CDCl$_3$) δ1.44 (s, 9H), 1.62 (m, 2H), 1.75 (m, 2H), 1.91 (m, 1H), 2.18 (m, 1H), 2.68 (m, 2H), 3.25 (m, 2H) 4.05 (m, 2H), 4.37 (m, 1H), 5.11 (s, 1H), 7.09–7.19 (m, 7H), 7.32 (m, 6H), 7.45 (t, J=9.0 Hz, 1H), and 7.75 (m, 3H).

(D) Homophenylalanyl-Ornithinyl 2-Naphthyl Ether Trifluoroacetate

Hydrogen was bubbled through a solution of N$_α$-Boc-homophenylalanyl-N$_δ$-Cbz-ornithinyl 2-naphthyl ether (C) (130 mg) and methanol (10 ml), with 10% palladium-on-charcoal (10 mg), until starting material was absent (thin-layer chromatography). The reaction mixture is filtered through a 0.45 μm nylon pad and concentrated in vacuo, and the residue dissolved in trifluoroacetic acid (2 ml). After 1 hr, the solution was concentrated in vacuo: $^1$H NMR (400 MHz, D$_2$O) δ1.82–1.91 (m, 4H), 2.16 (m, 2H), 2.63 (m, 2H), 3.17 (m, 2H), 4.12 (t, J=5.0; 8.0 Hz, 1H), 4.22 (dd, J=11.6; 8.5

Hz, 1H), 4.37 (dd, J=11.6; 2.3 Hz, 1H), 4.98 (m 1H), 6.90 (d, J=10.2 Hz, 2H), 7.07 (t, J=9.0 Hz, 2H), 7.18 (d, J=7.7 Hz, 1H), 7.21 (d, J=9.0 Hz, 1H), 7.40 (s, 1H), 7.50 (t, J=8.0 Hz, 1H), 7.59 (t, J=7.5 Hz, 1H), and 7.80–7.92 (m, 3H).

Example 96
2-Methyltyrosyl-Ornithinyl 1-Naphthyl Ether Trifluoroacetate

This was similarly prepared as described in Example 95, except Boc-2-methyltyrosine and $N_\alpha$-Boc-$N_\delta$-CBz-ornithinyl 1-naphthyl ether were used.

Example 97
β-(2-Thienyl)alanyl-Lysinyl 3,4Dimethylphenyl Ether Trifluoroacetate This was similarly prepared as described in Example 95, except Boc-p-(2-thienyl)-alanine and $N_\alpha$-Boc-$N_\epsilon$-CBz-lysinyl 3,4-dimethylphenyl ether were used.

Example 98
Leucyl-D-Leucinyl 2-Benzimidazolyl Ether Trifluoroacetate

This was similarly prepared as described in Example 95, except Boc-leucine and D-leucinyl 2-benzimidazolyl ether were used.

Example 99
D-Lysyl-D-Leucinyl 3-Quinolinyl Ether Trifluoroacetate

This was similarly prepared as described in Example 95, except $N_\alpha$,$N_\epsilon$-bis-Boc-D-lysine and D-leucinyl 3-quinolinyl ether were used.

Example 100
D-Ornithyl-D-Phenylalaninyl 2-Naphthyl Ether Trifluoroacetate

This was similarly prepared as described in Example 95, except $N_\alpha$,$N_\delta$-bis-Boc-D-ornithine and D-phenylalaninyl 2-naphthyl ether were used: $^1$H NMR (400 MHz, $D_2O$) δ2.58–2.80 (4H), 2.65–2.68 (2H), 2.98–3.23 (2H), 3.90–4.00 (1H), 4.20–4.40 (2H), 4.61–4.64 (1H), 7.25–7.60 (10H), and 7.80–8.05 (2H); mass spectrum (relative intensity) m/e 392 (80 M+1).

Example 101
Phenylalanyl-Ornithinyl 2-Naphthyl Ether Trifluoroacetate

This was similarly prepared, as described in Example 95, except Boc-phenylalanine and $N_\alpha$-Boc-$N_\delta$-Cbz-ornithinyl 2-naphthyl ether were used: $^1$H NMR (400 MHz, $D_2O$) δ1.78–1.89 (m, 4H), 3.10 (m, 3H), 3.23 (dd, J=13.6; 6.0 Hz, 1H), 3.88 (dd, J=10.0; 3.6 Hz, 1H), 4.02 (dd, J=10.4; 5.2 Hz, 1H), 4.27 (m, 2H), 6.96 (t, J=7.2 Hz, 1H), 7.14 (m, 2H), 7.23 (m, 3H), 7.31 (s, 1H), 7.53 (t, J=8.0 Hz, 1H), 7.64 (t, J=6.8 Hz, 1H), and 7.97 (m, 3H).

Example 102
Homophenylalanyl-$N_\alpha$-Methylornithinyl 2-Naphthyl Ether Trifluoroacetate (A) $N_\alpha$-Benzyl-$N_\delta$-Boc-Ornithine A solution of $N_\delta$-Boc-ornithine (7.0 g), 2M sodium hydroxide (20 ml), benzaldehyde (3.2 ml) and methanol (10 ml) was cooled to 0° C. and sodium borohydride (2.7 g) was added. After 1 hr at 0° C., the mixture was kept at 25° C. for 12 h. Water (100 ml) was added and the mixture extracted with ether (2×60 ml). The combined organic extract was washed with sat. sodium bicarbonate (ca. 150 ml) and water, and dried over anhydrous sodium sulfate. After concentration in vacuo, the desired product (4.5 g) was obtained as a white solid: $^1$H NMR (400 MHz, $CD_3OD$) δ1.42 (s, 9H), 1.60 (m, 2H), 1.84 (m, 2H), 3.03 (m, 2H), 3.50 (t, J=7.4 Hz, 1H), 4.11 (d, J=11.9 Hz, 1H), 4.21 (d, J=11.9 Hz, 1H), 7.41 (m, 3H), and 7.49 (m, 2H).

(B) $N_\alpha$-Benzyl-$N_\delta$-Boc-$N_\alpha$-Methylornithine

36% Formalin (5.8 ml) is added to a suspension of $N_\alpha$-benzyl-$N_\delta$-Boc-ornithine (A) (3.66 g) in acetonitrile (220 ml), methanol (110 ml) and water (110 ml), and the mixture stirred at 25° C. until clear. After cooling to 0° C., sodium cyanoborohydride (1.6 g) was added and the mixture maintained at 25° C. for 10 hrs. Water (190 ml) was added, and the mixture acidified with 5% citric acid to pH 3.5. After extracting with chloroform (3×60 ml), the combined organic phase is washed with brine and dried over anhydrous sodium sulfate. Removal of the solvent in vacuo afforded amino acid (2.1 g) as a white solid: $^1$H NMR (400 MHz, $CD_3OD$) δ1.42 (s 9H), 1.61 (m, 1H), 1.73 (m, 1H), 1.97 (m, 2H), 2.77 (s, 3H), 3.09 (m, 2H), 3.61 (m, 1H), 4.30 (m, 2H), 7.46 (m, 3H), and 7.56 (m, 2H).

(C) $N_\alpha$-Benzyl-$N_\delta$-Boc-$N_\alpha$-Methylornithinol

Using Procedure F, $N_\alpha$-benzyl-$N_\delta$-Boc-$N_\alpha$-methylornithine (B) (2.7 g) is converted to alcohol (C) (2.0 g) as a white solid, after silica gel chromatography (5% methanol/dichloromethane): $^1$H NMR (400 MHz, $CDCl_3$) δ1.20 (m, 1H), 1.42 (broad s, 11H), 1.61 (m, 1H), 2.18 (s, 3H), 2.79 (m, 1H), 3.12 (m, 2H), 3.33 (broad s, 1H), 3.37 (t, J=10.4 Hz, 1H), 3.52 (m, 2H), 3.69 (d, J=13.2 Hz, 1H), and 7.24 (m, 5H).

(D) $N_\alpha$-Benzyl-$N_\delta$-Boc-$N_\alpha$-Methylornithinyl 2-Naphthyl Ether A μιξτυρε Οφ $N_\alpha$-benzyl-$N_\delta$-Boc-$N_\alpha$-methylornithinol (168 mg), dichloromethane (10 ml), 2-naphthol (91 mg), triphenylphosphine (165 mg), and N,N'-diisopropylazodicarboxamide (124 μl) was stirred for 12 hrs at 25° C., under nitrogen. The reaction mixture was poured into dichloromethane and washed successively with saturated sodium bicarbonate and brine. The organic phase was then dried over anhydrous sodium sulfate and concentrated in vacuo. Further purification by flash chromatography gave the titled product (90 mg) as a white solid. $^1$H NMR (400 MHz, $CDCl_3$) δ1.51 (s, 9H), 1.68 (m, 2H), 1.75 (m, 2H), 2.39 (s, 3H), 3.20 (m, 2H), 3.82 (d, J=13.3, 1H), 3.93 (d, J=13.2, 1H), 4.11 (dd, J=9.6; 3.6, 1H), 4.29 (dd, J=10.2; 8.4, 1H), 7.22 (m, 2H), 7.29 (t, J=7.8, 1H), 7.39 (m, 5H), 7.50 (t, J=8.0, 1H), 7.79 (m, 3H).

(E) $N_\delta$-Boc-$N_\alpha$-Methylornithinyl 2-Naphthyl Ether

A methanolic solution of $N_\alpha$-benzyl-$N_\delta$-Boc-$N_\alpha$-methylornithinyl 2-naphthyl ether (D) was reduced with hydrogen, over 5% palladium-on-carbon, to afford titled product: $^1$H NMR (400 MHz, $CDCl_3$) δ1.44 (s, 9H), 1.63 (m, 2H), 1.95 (m, 2H), 2.53 (s, 3H), 2.95 (m, 1H), 3.09 (m, 2H), 4.01 (dd, J=10.7; 6.7 Hz, 1H), 4.12 (dd, J=10.5; 4.4 Hz, 1H), 7.19 (m, 2H), 7.35 (t, J=9.1 Hz, 1H), 7.45 (t, J=8.9 Hz, 1H), and 7.75 (m, 3H).

(F) Boc-Homophenylalanyl-$N_\delta$-Boc-$N_\alpha$-Methylornithinyl 2-Naphthyl Ether Using Procedure D, coupling of $N_\delta$-Boc-$N_\alpha$-methylornithinyl 2-naphthyl ether (E) and Boc-homophenylalanine afforded titled compound as a glassy solid: $^1$H NMR (400 MHz, $CDCl_3$) δ1.44 (2s, 18H), 1.58–1.70 (m, 4H), 1.98 (m, 2H), 2.73 (m, 2H), 2.83 (s, 3H), 3.18 (m, 2H), 4.08 (m, 2H), 4.61 (m, 1H), 7.09 (m, 2H), 7.35 (m, 5H), 7.49 (t, J=9.1 Hz, 1H), 7.59 (t, J=9.0 Hz, 1H), and 7.81 (3H).

(G) Homophenylalanyl-$N_\alpha$-Methylornithinyl 2-Naphthyl Ether Trifluoroacetate Treatment of Boc-homophenylalanyl-$N_\delta$-Boc-$N_\alpha$-methylornithinyl 2-naphthyl ether (F) (60 mg) with trifluoroacetic acid (Procedure E) afforded product as a white solid (63 mg); HPLC (method A): $^1$H NMR (400 MHz, D$_2$O) δ1.77 (m, 4H), 2.01 (m, 1H), 2.15 (m, 1H), 2.75 (m, 2H), 2.89 (s, 3H), 3.11 (m, 2H), 4.26 (dd, J=10.8; 3.2 Hz, 1H), 4.34 (t, J=10.8 Hz, 1H), 4.55 (m, 1H), 5.08 (m, 1H), 7.09 (m, 2H), 7.35 (m, 5H), 7.49 (t, J=7.6 Hz, 1H), 7.59 (t, J=7.2 Hz, 1H), 7.75 (d, J=9.2 Hz, 1H), 7.82 (d, J=8.4 Hz, 1H), and 7.89 (d, J=8.4 Hz, 1H).

Example 103

O-Benzylseryl-N$_α$-Methylornithinyl 2-Naphthyl Ether Trifluoroacetate (A) Boc-O-Benzylseryl-N$_δ$-Boc-N$_α$-Methylornithinyl 2-Naphthyl Ether Using Procedure D, crude N$_δ$-Boc-N$_α$-methylornithinyl 2-naphthyl ether (37 mg) and Boc-O-benzylserine (62 mg) was coupled to afford product (62 mg) as a colorless oil: $^1$H NMR (400 MHz, CDCl$_3$) δ1.49 (broad s, 21H), 1.77 (m, 1H), 3.08 (s, 3H), 3.17 (s, 2H), 3.64 (m, 2H), 4.05 (dd, J=13.0; 3.8 Hz, 1H), 4.14 (dd, J=13.0; 7.3 Hz, 1H), 4.52 (m, 3H), 4.91 (m, 1H), 7.05 (m, 2H), 7.20 (m, 3H), 7.32 (m, 3H), 7.41 (m, 1H), and 7.69 (m, 3H); mass spectrum (ES+) m/e 636 (M+1).

(B) O-Benzylseryl-N$_α$-Methylornithinyl 2-Naphthyl Ether Trifluoroacetate

Boc-O-benzylseryl-N$_δ$-Boc-N$_α$-Methylornithinyl 2-naphthyl ether, after treatment with trifluoroacetic acid, afforded titled compound as a white solid: HPLC (method C); $^1$H NMR (400 MHz, CDCl$_3$) δ1.52 (m, 1H), 1.63 (m, 2H), 1.78 (m, 1H), 2.82 (s, 3H), 2.88 (m, 2H), 3.86 (broad s, 4H), 4.47 (m, 2H), 4.61 (m, 1H), 5.05 (m, 1H), 6.86 (d, J=10.8 Hz, 1H), 6.92 (s, 1H), 7.10 (m, 3H), 7.18 (m, 2H), 7.30 (t, J=8.0 Hz, 1H), 7.39 (t, J=8.1 Hz, 1H), 7.61 (t, J=8.7 Hz, 2H), and 7.75 (d, J=9.0 Hz, 1H); mass spectrum (ES+) m/e 436 (M+1).

Example 104

Tyrosyl-N$_α$-Methylornithinyl 2-Naphthyl Ether Trifluoroacetate (A) Boc-Tyrosyl-N$_δ$-Boc-N$_α$-Methylornithinyl 2-Naphthyl Ether Using Procedure D, crude N$_δ$-Boc-N$_α$-methylornithinyl 2-naphthyl ether (133 mg) and Boc-tyrosine (222 mg) is coupled to afford intermediate (125 mg) as a glassy solid: $^1$H NMR (400 MHz, CDCl$_3$) δ1.44 (m, 21H), 1.63 (m, 1H), 2.75 (s, 3H), 3.15 (m, 2H), 3.92 (m, 2H), 4.84 (m, 1H), 5.06 (m, 1H), 6.62 (d, J=10.2 Hz, 2H), 7.08 (m, 4H), 7.35 (m, 1H), 7.42 (m, 1H), 7.66 (d, J=10.9 Hz, 1H), and 7.75 (m, 3H).

(B) Tyrosyl-N$_α$-Methylornithinyl 2-Naphthyl Ether Trifluoroacetate

Boc-Tyrosyl-N$_δ$-Boc-N$_α$-methylornithinyl 2-naphthyl ether (125 mg) was treated with trifluoroacetic acid (Procedure E) to afford titled product (100 mg) as a white solid: $^1$H NMR (400 MHz, D$_2$O) δ1.77 (m, 4H), 2.78 (m, 3H), 3.08 (m, 4H), 4.06 (dd, J=11.4; 3.6 Hz, 1H), 4.17 (dd, J=1 1.5; 8.4 Hz, 1H), 4.72 (t, J=7.8 Hz, 1H), 4.89 (m, 1H), 6.65 (d, J=10.8 Hz, 2H), 7.17 (d, J=10.8 Hz, 2H), 7.22 (dd, J=9.6; 1.1 Hz, 1H), 7.34 (s, 1H), 7.51 (t, J=8.4 Hz, 1H), 7.61 (t, J=8.4 Hz, 1H), 7.94 (m, 3H).

Example 105

Phenylalanyl-N$_α$-Methylornithinyl (4Methoxy-2naphthyl) ether Trifluoroacetate

This was prepared, as described in Example 104, except the starting materials were Boc-phenylalanine and N$_δ$-Boc-N$_α$-methylornithinyl (4-methoxy-2-naphthyl)ether.

Example 106

Tyrosyl-N$_α$-Methylornithinyl (4-Methoxy-2-naphthyl)ether Trifluoroacetate

This was prepared, as described in Example 104, except the starting materials were Boc-tyrosine and N$_δ$-Boc-N$_α$-methylornithinyl (4-methoxy-2-naphthyl)ether.

Example 107

Phenylalanyl-N$_α$-Benzylornithinyl (4-Methoxy-2-naphthyl) ether Trifluoroacetate This was prepared, as described in Example 104, except the starting materials were Boc-phenylalanine and N$_δ$-Boc-N$_α$-benzylornithinyl (4-methoxy-2-naphthyl)ether.

Example 108

Tyrosyl-N$_α$-Ethylornithinyl (4-Methoxy-2-naphthyl)ether Trifluoroacetate

This was prepared, as described in Example 104, except the starting materials were Boc-tyrosine and N$_δ$-Boc-N$_α$-ethylornithinyl (4-methoxy-2-naphthyl)ether.

Example 109

4-Fluorohomophenylalanyl-N$_α$-Methylornithinyl 2-Naphthyl Ether Trifluoroacetate This was prepared, as described in Example 104, except the starting materials were Boc-4-fluorohomophenylalanine and N$_δ$-Boc-N$_α$-methylornithinyl 2-naphthyl ether.

Example 110

4-Fluorohomophenylalanyl-N$_α$-Methylornithinyl 2-Quinolinyl Ether Trifluoroacetate This was prepared, as described in Example 104, except the starting materials were Boc-4-fluorohomophenylalanine and N$_δ$-Boc-N$_α$-methylornithinyl 2-quinolinyl ether.

Example 111

Homophenylalanyl-N$_α$-Methylornithinyl 3-Quinolinyl Ether Trifluoroacetate

This was prepared, as described in Example 104, except the starting materials were Boc-homophenylalanine and N$_δ$-Boc-N$_α$-methylornithinyl 3-quinolinyl ether.

Example 112

3-Fluorotyrosyl-N$_α$-Methylornithinyl 4-Quinolinyl Ether Trifluoroacetate

This was prepared, as described in Example 104, except the starting materials were Boc-3-fluorotyrosine and N$_δ$-Boc-N$_α$-methylornithinyl 4-quinolinyl ether.

Example 113

Homophenylalanyl-N$_α$-Methoxybenzyl)ornithinyl 3-Quinolinyl Ether Trifluoroacetate This was prepared, as described in Example 104, except the starting materials were Boc-homophenylalanine and N$_δ$-Boc-N$_α$-(4-methoxybenzyl)ornithinyl 3-quinolinyl ether.

Example 114

Tryptophane-N$_α$-Methylornithinyl 3-Quinolinyl Ether Trifluoroacetate

This was prepared, as described in Example 104, except the starting materials were Boc-tryptophane and N$_δ$-Boc-N$_α$-methylornithinyl 3-quinolinyl ether.

Example 115

2,4-Dichlorophenylalanyl-N$_α$-Methylornithinyl (3,4-Dimethylphenyl)ether Trifluoroacetate This was prepared, as described in Example 104, except the starting materials were Boc-2,4-dichlorophenylalanine and N$_δ$-Boc-N$_α$-methylornithinyl (3,4-dimethylphenyl) ether.

Example 116
β-(2-Naphthyl)alanyl-N$_\alpha$-Methylornithinyl(3,4-Dimethoxyphenyl)ether Trifluoroacetate This was prepared, as described in Example 104, except the starting materials were Boc-β-(2-naphthyl)alanine and N$_\delta$-Boc-N$_\alpha$-methylornithinyl (3,4-dimethoxyphenyl)ether.

Example 117
Homophenylalanyl-N$_\alpha$-Methylargininyl 2-Naphthyl Ether Trifluoroacetate (A) N$_\omega$,N$_\omega$'-Bis-Boc-N$_\alpha$-Methylargininyl 2-Naphthyl Ether Compound is prepared in three steps from N$_\alpha$-benzyl-N$_\delta$-Boc-N$_\alpha$-methylornithinol. First, the Boc protecting group is removed using trifluoroacetic acid, then the amine salt is guanidinylated with N,N'-bis-Boc-1-guanylpyrazole. Removal of the benzyl group was accomplished by catalytic hydrogenation over 5% palladium-on-carbon: $^1$H NMR (400 MHz, CDCl$_3$) δ1.48 (s, 18H), 1.73 (m, 4H), 2.48 (s, 3H), 2.95 (m, 1H), 3.47 (m, 2H), 4.04 (dd, J=10.9; 6.0 Hz, 1H), 4.13 (dd, J=11.0; 2.7 Hz, 1H), 7.15 (m, 2H), 7.35 (t, J=8.4 Hz, 1H), 7.44 (t, J=8.4 Hz, 1H), and 7.94 (m, 3H).

(B) Boc-Homophenylalanyl-N$_\omega$,N$_\omega$'-Bis-Boc-N$_\alpha$-Methylargininyl 2-Naphthyl Ether Using Procedure D, N$_\omega$,N$_\omega$'-bis-Boc-N$_\alpha$-methylargininyl 2-naphthyl ether was coupled with Boc-homophenylalanine to afford a white solid: $^1$H NMR (400 MHz, D$_2$O) δ1.47 (m, 29H), 1.66 (m, 1H), 1.76 (m, 1H), 1.95 (m, 1H), 2.04 (m, 1H), 2.73 (m, 2H), 2.85 (s, 3H), 4.11 (m, 2H), 4.62 (m, 1H), 5.14 (m, 1H), 6.99–7.16 (m, 7H), 7.49 (t, 1H), 7.59 (t, 1H), and 7.64–7.77 (m, 3H).

(C) Homophenylalanyl-N$_\alpha$-Methylargininyl 2-Naphthyl Ether Trifluoroacetate This compound is obtained by treatment of Boc-homophenylalanyl-N$_\omega$,N$_\omega$'-bis-Boc-N$_\alpha$-methylargininyl 2-naphthyl ether with trifluoroacetic acid, followed by HPLC purification.

Example 118
N-(C-Amidino)homophenylalanyl-N$_\alpha$-Methylargininyl 2-Naphthyl Ether Trifluoroaetate Homophenylalanyl-N$_\alpha$-methylornithinyl 2-naphthyl ether (41 mg) and N,N'-bis-Boc-1-guanylpyrazole (19 mg) was coupled to afford N-(bis-Boc-C-amidino)homophenyl-alanine-N$_\omega$,N$_\omega$, -bis-Boc-N$_\alpha$-methylargininyl 2-naphthyl ether (56 mg). Deprotection of the intermediate by Procedure E, followed by HPLC purification afforded titled product as a white solid: $^1$H NMR (400 MHz, D$_2$O) δ1.65 (m, 2H), 1.72 (m, 2H), 1.93 (m, 1H), 2.13 (m, 1H), 2.78 (m, 2H), 2.92 (2s, 3H, rotamers), 3.29 (m, 2H), 4.27 (m, 1H), 4.38 (t, J=13.0 Hz, 1H), 4.53 (m, 1H), 5.03 (m, 1H), 7.12 (m, 2H), 7.37 (m, 4H), 7.52 (m, 1H), 7.60 (m, 1H), and 7.81–7.96 (m, 3H).

Example 119
Homophenylalanyl-N$_\alpha$-Methylornithinyl 2-Benzothiazolyl Thioether Trifluoroacetate (A) O-(tert-Butyldimethylsilyl)-N$_\alpha$-Benzyl-N$_\delta$-Boc-N$_\alpha$-Methylornithinol A solution of N$_\alpha$-benzyl-N$_\delta$-Boc-N$_\alpha$-methylornithinol (560 mg), dimethylformamide (1.5 ml), and t-butyldimethylsilyl chloride (330 mg), triethylamine (290 μl) and 4-(N,N-dimethylamino)pyridine (21 mg) was stirred at 0° C., under nitrogen atmosphere, for 1 hr. Then the mixture was stirred, at 25° C., for 10 hrs and then poured into water (20 ml) and extracted with dichloromethane (2×20 ml). The combined organic phase was washed with water and brine, and dried over sodium sulfate. Evaporation of the solvent afforded titled compound (690 mg) as a clear solid: $^1$H NMR (400 MHz, CDCl$_3$) δ0.06 (s, 6H), 0.91 (s, 9H), 1.43 (s, 9H), 1.45–1.73 (m, 4H), 2.22 (s, 3H), 2.68 (m, 1H), 3.12 (m, 2H), 3.62 (dd, J=10.4; 5.2 Hz, 1H), 3.68 (d, J=13.6 Hz, 1H), 3.78 (m, 2H), and 7.30 (m, 5H).

(B) O-(tert-Butyldimethylsilyl)-N$_\delta$-Boc-N$_\alpha$-Methylornithinol

Reduction of O-(tert-butyldimethylsilyl)-N$_\alpha$-benzyl-N$_\delta$-Boc-N$_\alpha$-methylornithinol (A) (690 mg) afforded titled compound (485mg) which was used in the subsequent reaction: $^1$H NMR (400 MHz, CDCl$_3$) δ0.09 (s, 6H), 0.92 (s, 9H), 1.39–1.68 (m, 13H), 2.40 (s, 3H), 2.48 (m, 1H), 3.12 (m, 2H), 3.46 (dd, J=10.0; 6.4 Hz, 1H), and 3.62 (dd, J=9.6; 4.0 Hz, 1H).

(C) Boc-Homophenylalanyl-O-(tert-butyldimethylsilyl)-N$_\delta$-Boc-N$_\alpha$-Methylornithinol Using Procedure D, coupling of O-(tert-butyldimethylsilyl)-N$_\delta$-Boc-N$_\alpha$-methylornithinol (B) (485 mg) and Boc-homophenylalanine (590 mg) afforded titled compound (767 mg) as a glassy solid: $^1$H NMR (400 MHz, CDCl$_3$) δ0.01 (s, 6H), 0.84 (s, 9H), 1.39–1.55 (broad s, 22H), 1.84 (m, 1H), 1.97 (m, 1H), 2.69 (m, 2H), 2.78 (s, 3H), 3.09 (m, 2H), 3.58 (d, J=5.7 Hz, 2H), 4.58 (m, 2H), 7.20 (m, 3H), and 7.26 (m, 2H).

(D) Boc-Homophenylalanyl-N$_\delta$-Boc-N$_\alpha$-Methylornithinol

A mixture of tetrabutylammonium fluoride (2.8 ml of 1M sol in tetrahydrofuran), Boc-homophenylalanyl-O-(tert-butyldimethylsilyl)-N$_\delta$-Boc-N$_\alpha$-methylornithinol (C) (576 mg), and dry tetrahydrofuran (5 ml) was stirred at 0° C. for 1 hr. The reaction mixture is poured into ethyl acetate and worked up, including purification by flash chromatography (5% methanol/dichloromethane) to yield desired product (402 mg) as a thick oil: $^1$H NMR (400 MHz, CDCl$_3$) δ1.44 (broad s, 22H), 1.86 (m, 1H), 2.00 (m, 1H), 2.79 (m, 4H) 3.09 (m, 2H), 3.43–3.69 (m, 2H), 4.45 (m, 1H), 4.63 (m, 1H), and 7.19–7.32 (m, 5H).

(E) Homophenylalanyl-N$_\alpha$-Methylornithinyl 2-Benzothiazolyl Thioether Trifluoroacetate This was prepared in a two step sequence. A solution of Boc-homophenylalanyl-N$_\delta$-Boc-N$_\alpha$-methylornithinol (D) (392 mg) and 2-mercaptobenzothiazole (267 mg) in dry tetrahydrofuran (9 ml) was cooled to 0° C. under nitrogen atmosphere. Then, a solution of triphenylphosphine (1.04 g), anhydrous tetrahydrofuran (1 ml), and diethyl azodicarboxy-late (620 μl) was added. The reaction mixture was stirred for 1.5 h at 0° C., concentrated in vacuo, and purified by flash chromatography (30% ethyl acetate/hexane) to give Boc-homophenylalanyl-N$_\delta$-Boc-N$_\alpha$-methylornithinyl 2-benzo-thiazolyl thioether (270 mg). This intermediate was deprotected by Procedure E to afford titled product (75 mg): HPLC [20 to 40% gradient (acetonitrile/0.1% TFA) over 60 min, retention time=42.96 min]; $^1$H NMR (400 MHz, D$_2$O) δ1.49 (m, 2H), 1.83 (m, 2H), 1.98 (m, 1H), 2.18 (m, 1H), 2.79 (m, 2H), 2.82 (s, 3H), 3.09 (m, 2H), 3.57 (dd, J=14.8; 11.2 Hz, 1H), 3.70 (dd, J=14.8; 4.0 Hz, 1H), 4.46 (m, 1H), 5.01 (m, 1H), 7.17 (m, 2H), 7.38 (m, 3H), 7.49 (t, J=8.0 Hz, 1H), 7.61 (t, J=7.2 Hz, 1H), 7.91 (d, J=8.0 Hz, 1H), and 7.94 (d, J=8.4 Hz, 1H).

Example 120
Phenylalanyl-N$_\alpha$-Methylornithinyl 3-Quinolinyl Thioether Trifluoroacetate This was prepared, as described in Example 119, except the starting materials were Boc-phenylalanyl-N$_\delta$-Boc-N$_\alpha$-methylornithinol and 3-mercaptoquinoline.

Example 121
Homophenylalanyl-N$_\alpha$-Ethylornithinyl 3-Quinolinyl Thioether Trifluoroacetate This was prepared, as described in Example 119, except the starting materials were Boc-homophenylalanyl-N$_\delta$-Boc-N$_\alpha$-ethylornithinol and 3-mercaptoquinoline.

Example 122
Phenylalanyl-N$_\alpha$-Methylornithinyl 2-Quinolinyl Thioether Trifluoroacetate This was prepared, as described in Example 119, except the starting materials were Boc-phenylalanyl-N$_\delta$-Boc-N$_\alpha$-methylornithinol and 2-mercaptoquinoline.

Example 123
Tryptophanyl-N$_\alpha$-Methylornithinyl 4-Quinolinyl Thioether Trifluoroacetate This was prepared, as described in Example 119, except the starting materials were Boc-tryptophanyl-N$_\delta$-Boc-N$_\alpha$-methylornithinol and 4-mercaptoquinoline.

Example 124
4-Chlorophenylalanyl-N$_\alpha$-Methylornithinyl 2-Quinolinyl Thioether Trifluoroacetate This was prepared, as described in Example 119, except the starting materials were Boc-4-chlorophenylalanyl-N$_\delta$-Boc-N$_\alpha$-methylornithinol and 2-mercaptoquinoline.

Example 125
Homophenylalanyl-N$_\alpha$-Methylornithinyl 2-Benzimidazolyl Thioether Trifluoroacetate This was prepared, as described in Example 119, except the starting materials were Boc-homophenylalanyl-N$_\delta$-Boc-N$_\alpha$-methylornithinol and 2-mercaptobenzimidazole.

Example 126
Homophenylalanyl-N$_\alpha$-Methyllysinyl 2-Benzimidazolyl Thioether Trifluoroacetate This was prepared, as described in Example 119, except the starting materials were Boc-homophenylalanyl-N$_\epsilon$-Boc-N$_\alpha$-methyllysinol and 2-mercaptobenzimidazole.

Example 127
Tyrosyl-N$_\alpha$-Methyllysinyl 2-Benzimidazolyl Thioether Trifluoroacetate This was prepared, as described in Example 119, except the starting materials were Boc-tyrosyl-N$_\epsilon$-Boc-N$_\alpha$-methyllysinol and 2-mercaptobenzimidazole.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The efflux inhibitor compounds, synthetic methods, antimicrobial agents, target organisms, and administration modes described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, those skilled in the art will readily recognize that the present efflux inhibitor compounds can incorporate a variety of different substituent groups, and that the pharmaceutical compositions may incorporate a variety of different antimicrobial agents. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What we claim is:

1. A method for treating a microbial infection in an animal, comprising administering to an animal suffering from said infection an antimicrobial agent and an efflux pump inhibitor in an amount sufficient to reduce efflux pump activity, wherein said efflux pump inhibitor increases the susceptibility of said microbe to said antimicrobial agent, and wherein said efflux pump inhibitor has the chemical structure of structure 1 below:

Structure 1

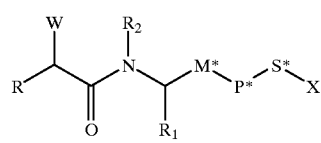

wherein

M* is (CH$_2$)$_n$ (n=0,1, or 2)

P* is CH$_2$, carbonyl (C=O), or thiocarbonyl (C=S)

S* is NH, O, or SO$_t$ (t=0,1, or 2);

R is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, or (CH$_2$)$_n$N=CNR$^b$R$^c$, wherein n=1,2,3, or 4, and R$^a$, R$^b$, and R$^c$ are independently H, lower alkyl, phenyl, substituted phenyl, benzyl, cyano, hydroxy, or nitro, or R$^a$+R$^b$ or R$^b$+R$^c$ is (CH$_2$)$_{2-3}$ or —CH=CH—;

R$^1$ is H, lower alkyl, branched alkyl, fluoroalkyl, perfluoroalkyl, carboxyalkyl, aryl, 2-(or 3-)thienyl, 2-(or 3-)furyl, or 2-(3- or 4-)pyridyl, arylalkyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (NR$^a$)NR$^b$R$^c$, (CH$_2$)$_n$C=(NR$^a$)NR$^b$R$^c$, or (CH$_2$)$_n$ N=CNR$^b$R$^c$, wherein n=1,2,3, or 4 and R$^a$, R$^b$, and R$^c$ are independently H, lower alkyl, phenyl, benzyl, cyano, hydroxy, or nitro, or R$^a$+R$^b$ (or R$^b$+R$^c$) is (CH$_2$)$_{2-3}$ or —CH=CH—;

R$^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, or (CH$_2$)$_n$N=CNR$^b$R$^c$, wherein n=1,2,3, or 4 and R$^a$, R$^b$, and R$^c$ are independently H, lower alkyl, phenyl, benzyl, cyano, hydroxy, or nitro, or R$^a$+R$^b$ or R$^b$+R$^c$ is (CH$_2$)$_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, quinoxalinylalkyl, quinazolinylalkyl, benzimidazolylalkyl, benzothiazolylalkyl, or benzoxazolylalkyl.

2. The method of claim 1, wherein said efflux pump inhibitor has Structure 2,

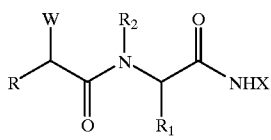

Structure 2 wherein

R is H, lower alkyl, branched alkyl, fluoroalkyl, perfluoroalkyl, carboxyalkyl, hydroxyalkyl, aryl, monosubstituted aryl, disubstituted aryl, 2-(or 3-)thienyl, 2-(or 3-)furyl, or 2-(3- or 4-)pyridyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, or (CH$_2$)$_n$N=CNR$^b$R$^c$, wherein n=1,2,3, or 4 and R$^a$, R$^b$, and R$^c$ are independently H, lower alkyl, phenyl, benzyl, cyano, hydroxy, or nitro, or R$^a$+R$^b$ or R$^b$+R$^c$ is (CH$_2$)$_{2-3}$ or —CH=CH—;

R$^1$ is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl,thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, (CH$_2$)$_n$N=CNR$^b$R$^c$, wherein n=1,2,3, or 4 and R$^a$, R$^b$ or R$^c$ are independently H, lower alkyl, phenyl, benzyl, cyano, hydroxy, or nitro, or R$^a$+R$^b$ or R$^b$+R$^c$ is (CH$_2$)$_{2-3}$ or —CH=CH—;

R$^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, (CH$_2$)$_n$N=CNR$^b$R$^c$, wherein n=1,2,3, or 4 and R$^a$, R$^b$ and R$^c$ are independently H, lower alkyl, phenyl, benzyl, cyano, hydroxy, or nitro, or R$^a$+R$^b$ or R$^b$+R$^c$ is (CH$_2$)$_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, isoquinolinyl, quinoxalinylalkyl, quinazolinylalkyl, benzimidazolylalkyl, benzothiazolylalkyl, or benzoxazolylalkyl.

3. The method of claim 1, wherein said efflux pump inhibitor has Structure 3,

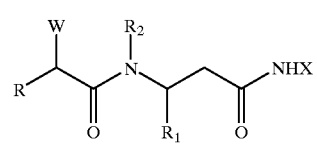

Structure 3 wherein

R is H, lower alkyl, branched alkyl, fluoroalkyl, perfluoroalkyl, carboxy-alkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, or (CH$_2$)$_n$N=CNR$^b$R$^c$, wherein n=1,2,3, or 4 and R$^a$, R$^b$ and R$^c$ are independently H, lower alkyl, phenyl, benzyl, cyano, hydroxy, or nitro, or R$^a$+R$^b$ or R$^b$+R$^c$ is (CH$_2$)$_{2-3}$ or —CH=CH—;

R$^1$ is H, lower alkyl, branched alkyl, fluoroalkyl, perfluoroalkyl, carboxy-alkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, or (CH$_2$)$_n$N=CNR$^b$R$^c$, wherein n=1,2,3 or 4 and R$^a$, R$^b$ and R$^c$ are independently H, lower alkyl, phenyl, benzyl, cyano, hydroxy, or nitro, or R$^a$+R$^b$ or R$^b$+R$^c$ is (CH$_2$)$_{2-3}$ or —CH=CH—;

R$^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, (CH$_2$)$_n$N=CNR$^b$R$^c$, wherein n=1,2,3, or 4 and R$^a$, R$^b$ and R$^c$ are independently H, lower alkyl, phenyl, benzyl, cyano, hydroxy, or nitro, or R$^a$+R$^b$ or R$^b$+R$^c$ is (CH$_2$)$_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, 4. The method of claim 1, wherein said efflux pump inhibitor has structure 4,

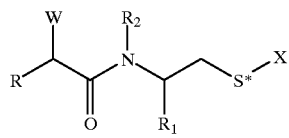

Structure 4 wherein

S* is NH, O, or SO$_t$ (t=0,1, or 2);

R is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, (CH$_2$)$_n$N=CNR$^b$R$^c$, wherein n=1,2,3, or 4 and R$^a$, R$^b$ and R$^c$ are independently H, alkyl, phenyl, benzyl, cyano, hydroxy, or nitro, or R$^a$+R$^b$ or R$^b$+R$^c$ is (CH$_2$)$_{2-3}$ or —CH=CH—;

R$^1$ is H, alkyl, branched alkyl, fluoroalkyl, perfluoroalkyl, carboxyalkyl, aryl, 2-(or 3-)thienyl, 2-(or 3-)furyl, or 2-(3- or 4-)pyridyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, (CH$_2$)$_n$N=CNR$^b$R$^c$, wherein n=1,2,3, or 4 and R$^a$, R$^b$ and R$^c$ are independently H, lower alkyl, phenyl, benzyl, cyano, hydroxy, or nitro, or R$^a$+R$^b$ or R$^b$+R$^c$ is (CH$_2$)$_{2-3}$ or —CH=CH—;

R$^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, (CH$_2$)$_n$NR$^b$R$^c$, (CH$_2$)$_n$ NHC=(NR$^a$)NR$^b$R$^c$, (CH$_2$)$_n$SC=(NR$^a$)NR$^b$R$^c$, (CH$_2$)$_n$ C=(NR$^a$)NR$^b$R$^c$, (CH$_2$)$_n$N=CNR$^b$R$^c$, wherein n=1,2,3, or 4 and R$^a$, R$^b$ and R$^c$ are independently H, lower alkyl, phenyl, benzyl, cyano, hydroxy, or nitro, or R$^a$+R$^b$ or R$^b$+R$^c$ is (CH$_2$)$_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, quinoxalinylalkyl, quinazolinylalkyl, benzimidazolylalkyl, benzothiazolylalkyl, or benzoxazolylalkyl.

5. A method for prophylactic treatment of an animal, comprising administering to an animal at risk of a microbial infection an antimicrobial agent and an efflux pump inhibitor, wherein said efflux pump inhibitor increases the susceptibility of a microbe to said antimicrobial agent, and wherein said efflux pump inhibitor has the chemical structure of structure 1 below:

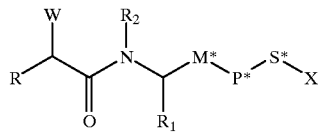

Structure 1 wherein

M* is (CH$_2$)$_n$ (n=0, 1, or 2)

P* is CH$_2$, carbonyl (C=O), or thiocarbonyl (C=S)

S* is NH, O, or SO$_t$ (t=0, 1 or 2);

R is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, or (CH$_2$)$_n$N=CNR$^b$R$^c$, wherein n=1, 2, 3 or 4, and R$^a$, R$^b$, and R$^c$ are independently H, lower alkyl, phenyl, substituted phenyl, benzyl, cyano, hydroxy, or nitro, or R$^a$+R$^b$ or R$^b$+R$^c$ is (CH$_2$)$_{2-3}$ or —CH=CH—;

R$^1$ is H, lower alkyl, branched alkyl, fluoroalkyl, perfluoroalkyl, carboxyalkyl, aryl, 2-(or 3-)thienyl, 2-(or 3-)furyl, or 2-(3- or 4-)pyridyl, arylalkyl, arylalkyl, thienylalkyl, furylalkyl, pyridylalkyl, (CH$_2$)$_n$NR$^b$R$^c$, (CH$_2$)$_c$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, or (CH$_2$)$_n$N=CNR$^b$R$^c$, wherein n=1, 2, 3 or 4 and R$^a$, R$^b$, and R$^c$ are independently H, lower alkyl, phenyl, benzyl, cyano, hydroxy, or nitro, or R$^a$+R$^b$ (or R$^b$+R$^c$) is (CH$_2$)$_{2-3}$ or —CH=CH—;

R$^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, (CH$_2$)$_n$NR$^b$R$^c$, (CH$_2$)$_n$NHC=(NR$^a$)NR$^b$R$^c$, (CH$_2$)$_n$SC=(NR$^a$)NR$^b$R$^c$, (CH$_2$)$_n$C=(NR$^a$)NR$^b$R$^c$, or (CH$_2$)$_n$N=CNR$^b$R$^c$, wherein n=1, 2, 3 or 4 and R$^a$, R$^b$, and R$^c$ are independently H, lower alkyl, phenyl, benzyl, cyano, hydroxy, or nitro, or R$^a$+R$^b$ or R$^b$+R$^c$ is (CH$_2$)$_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, quinoxalinylalkyl, quinazolinylalkyl, benzimidazolylalkyl, benzothiazolylalkyl, or benzoxazolylalkyl.

6. The method of claim 5, wherein said efflux pump inhibitor has Structure 2,

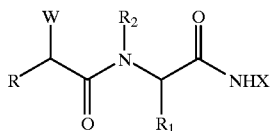

Structure 2 wherein
R is H, lower alkyl, branched alkyl, fluoroalkyl, perfluoroalkyl, carboxyalkyl, hydroxyalkyl, aryl, monosubstituted aryl, disubstituted aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, or $(CH_2)_n N=CNR^bR^c$, wherein n=1, 2, 3 or 4 and $R^a$, $R^b$, and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^1$ is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_n NNHC=(NR^a)NR^bR^c$, $(CH_2)_n SC=(NR^a)NR^bR^c$, $(CH_2)_n C=(NR^a)NR^bR^c$, $(CH_2)_n N=CNR^bR^c$, wherein n=1, 2, 3 or 4 and $R^a$, $R^b$ or $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or 3-)furyl, or 2-(3- or 4-)pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, $(CH_2)_n N=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, isoquinolinyl, quinoxalinylalkyl, quinazolinylalkyl, benzimidazolylalkyl, benzothiazolylalkyl, or benzoxazolylalkyl.

7. The method of claim 5, wherein said efflux pump inhibitor has Structure 3,

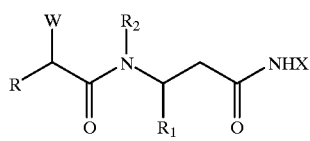

Structure 3 wherein
R is H, lower alkyl, branched alkyl, fluoroalkyl, perfluoroalkyl, carboxy-alkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, or $(CH_2)_n N=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^1$ is H, lower alkyl, branched alkyl, fluoroalkyl, perfluoroalkyl, carboxy-alkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, or $(CH_2)_n N=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or 3-)furyl, or 2-(3- or 4-)pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, $(CH_2)_n N=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, isoquinolinyl, quinoxalinylalkyl, quinazolinylalkyl, benzimidazolylalkyl, benzothiazolylalkyl, or benzoxazolylalkyl.

8. The method of claim 5, wherein said efflux pump inhibitor has structure 4,

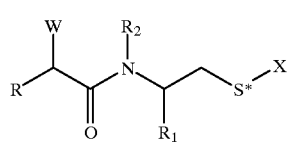

Structure 4 wherein
S* is NH, O, or Shd t(t=0, 1, or 2);
R is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, $(CH_2)_n N=CNR^bR^c$, wherein n=1, 2, 3 or 4 and $R^a$, $R^b$ and $R^c$ are independently H, alkyl, phenyl, benzyl, cyano, hydroxy, or nitro, or $R^a+R^b$ or $R^b+R^c$ is $(CH_2)_{2-3}$ or —CH=CH—;

$R^1$ is H, alkyl, branched alkyl, fluoroalkyl, perfluoroalkyl, carboxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$, wherein n=1, 2, 3 or 4 and $R^b$, $R^b$ and $R^c$, are independently H, lower alkyl, phenyl, benzyl, cyano, hydroxy, or nitro, or $R^a+R^b$ or $R^b+R^c$ is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or $^3$-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, quinoxalinylalkyl, quinazolinylalkyl, benzimidazolylalkyl, benzothiazolylalkyl, or benzoxazolylalkyl.

9. The method of any of claims 1, or 5, wherein said animal is a mammal.

10. A method of enhancing the antimicrobial activity of an antimicrobial agent against a microbe, comprising contacting said microbe with said antimicrobial agent and an efflux pump inhibitor in an amount effective to inhibit an efflux pump in said microbe, wherein said efflux pump inhibitor has the chemical structure of structure 1 below:

Structure 1

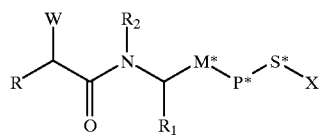

wherein

M* is $(CH_2)_n$ (n=0, 1, or 2)

P* is $CH_2$, carbonyl (C=O), or thiocarbonyl (C=S)

S* is NH, O, or $SO_t$ (t=0, 1, or 2);

R is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, or $(CH_2)_nN=CNR^bR^c$, wherein n=1, 2, 3 or 4, and $R^a$, $R^b$, and $R^c$ are independently H, lower alkyl, phenyl, substituted phenyl, benzyl, cyano, hydroxy, or nitro, or $R^a+R^b$ or $R^b+R^c$ is $(CH_2)_{2-3}$ or —CH=CH—;

$R^1$ is H, lower alkyl, branched alkyl, fluoroalkyl, perfluoroalkyl, carboxyalkyl, aryl, 2-(or 3-)thienyl, 2-(or 3-)furyl, or 2-(3- or 4-)pyridyl, arylalkyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, or $(CH_2)_nN=CNR^bR^c$, wherein n=1, 2, 3 or 4 and $R^a$, $R^b$, and $R^c$ are independently H, lower alkyl, phenyl, benzyl, cyano, hydroxy, or nitro, or $R^a+R^b$ (or $R^b+R^c$) is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, or $(CH_2)_nN=CNR^bR^c$, wherein n=1, 2, 3 or 4 and $R^a$, $R^b$, and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, quinoxalinylalkyl, quinazolinylalkyl, benzimidazolylalkyl, benzothiazolylalkyl, or benzoxazolylalkyl.

11. The method of claim 10, wherein said efflux pump inhibitor has Structure 2,

Structure 2

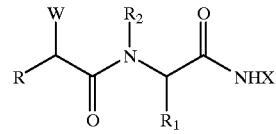

wherein

R is H, lower alkyl, branched alkyl, fluoroalkyl, perfluoroalkyl, carboxyalkyl, hydroxyalkyl, aryl, monosubstituted aryl, disubstituted aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, or $(CH_2)_nN=CNR^bR^c$, wherein n=1, 2, 3 or 4 and $R^a$, $R^b$, and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^1$ is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl,thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$, wherein n=1, 2, 3 or 4 and $R^a$, $R^b$ or $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofluranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, isoquinolinyl, quinoxalinylalkyl, quinazolinylalkyl, benzimidazolylalkyl, benzothiazolylalkyl, or benzoxazolylalkyl.

12. The method of claim 10, wherein said efflux pump inhibitor has Structure 3,

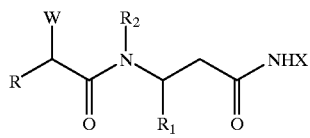

Structure 3 wherein
R is H, lower alkyl, branched alkyl, fluoroalkyl, perfluoroalkyl, carboxy-alkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, or $(CH_2)_nN=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^1$ is H, lower alkyl, branched alkyl, fluoroalkyl, perfluoroalkyl, carboxy-alkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, or $(CH_2)_nN=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, isoquinolinyl, quinoxalinylalkyl, quinazolinylalkyl, benzimidazolylalkyl, benzothiazolylalkyl, or benzoxazolylalkyl.

13. The method of claim 10, wherein said efflux pump inhibitor has structure 4,

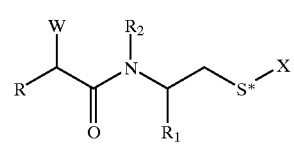

Structure 4 wherein
$S^*$ is NH, O, or $SO_t$ (t=0, 1 or 2);

R is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$, wherein n=1, 2, 3 or 4 and $R^a$, $R^b$ and $R^c$ are independently H, alkyl, phenyl, benzyl, cyano, hydroxy, or nitro, or $R^a+R^b$ or $R^b+R^c$ is $(CH_2)_{2-3}$ or —CH=CH—;

$R^1$ is H, alkyl, branched alkyl, fluoroalkyl, perfluoroalkyl, carboxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, quinoxalinylalkyl, quinazolinylalkyl, benzimidazolylalkyl, benzothiazolylalkyl, or benzoxazolylalkyl.

14. The method of any of claims 1, 5, or 10, wherein said microbe is a bacterium.

15. The method of claim 14, wherein said bacterial infection involves a bacterium selected from the group consisting of *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Gardnerella vaginalis, Bacteroides fragilis, Bacteroides distasonis,* Bacteroides 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis, Staphylococcus saccharolyticus.*

16. The method of any of claims 1, 5, or 10, wherein said microbial infection is a bacterial infection and said antimicrobial agent is an antibacterial agent.

17. The method of claim 16, wherein said antibacterial agent is a quinolone.

18. The method of claim 16, wherein said antibacterial agent is a tetracycline.

19. The method of claim 16, wherein said antibacterial agent is a β-lactam.

20. The method of claim 16, wherein said antibacterial agent is a coumermycin.

21. The method of claim 16, wherein said antibacterial agent is chloramphenicol.

22. The method of claim 16, wherein said antibacterial agent is a glycopeptide.

23. The method of claim 16, wherein said antibacterial agent is an aminoglycoside.

24. The method of claim 16, wherein said antibacterial agent is a macrolide.

25. The method of claim 16, wherein said antibacterial agent is a rifamycin.

26. The method of claim 16, wherein said antibacterial agent is an oxazolidonone.

27. The method of any of claims 1, 5, or 10, wherein said antimicrobial agent is effluxed by a microbe.

28. A pharmaceutical composition effective for treatment of an infection of an animal by a microbe, comprising an efflux pump inhibitor and a pharmaceutically acceptable carrier, wherein said efflux pump inhibitor has the chemical structure of structure 1 below:

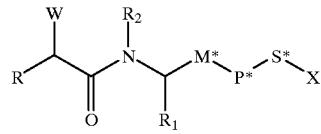

Structure 1 wherein $M^*$ is $(CH_2)_n$ (n=0, 1 or 2)

$P^*$ is $CH_2$, carbonyl (C=O), or thiocarbonyl (C=S)

$S^*$ is NH, O, or $SO_t$ (t=0, 1 or 2);

R is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^b R^c$, $(CH_2)_n NHC=(NR^a)NR^b R^c$, $(CH_2)_n SC=(NR^a)NR^b R^c$, $(CH_2)_n C=(NR^a)NR^b R^c$, or $(CH_2)_n N=CNR^b R^c$, wherein n=1, 2, 3 or 4, and $R^a$, $R^b$, and $R^c$ are independently H, lower alkyl, phenyl, substituted phenyl, benzyl, cyano, hydroxy, or nitro, or $R^a+R^b$ or $R^b+R^c$ is $(CH_2)_{2-3}$ or —CH=CH—;

$R^1$ is H, lower alkyl, branched alkyl, fluoroalkyl, perfluoroalkyl, carboxyalkyl, aryl, 2-(or 3-)thienyl, 2-(or 3-)furyl, or 2-(3- or 4-)pyridyl, arylalkyl, arylalkyl, thienylalkyl, furylalkyl, pyridylalkyl, $(CH_2)_n NR^b R^c$, $(CH_2)_n NHC=(NR^a)NR^b R^c$, $(CH_2)_n SC=(NR^a)NR^b R^c$, $(CH_2)_n C=(NR^a)NR^b R^c$, or $(CH_2)_n N=CNR^b R^c$, wherein n=1, 2, 3 or 4 and $R^a$, $R^b$, and $R^c$ are independently H, lower alkyl, phenyl, benzyl, cyano, hydroxy, or nitro, or $R^a+R^b$ (or $R^b+R^c$) is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or $^3$-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_n NR^b R^c$, $(CH_2)_n NHC=(NR^a)NR^b R^c$, $(CH_2)_n SC=(NR^a)NR^b R^c$, $(CH_2)_n C=(NR^a)NR^b R^c$, or $(CH_2)_n N=CNR^b R^c$, wherein n=1, 2, 3 or 4 and $R^a$, $R^b$, and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, quinoxalinylalkyl, quinazolinylalkyl, benzimidazolylalkyl, benzothiazolylalkyl, or benzoxazolylalkyl.

29. The pharmaceutical composition of claim 28, wherein said efflux pump inhibitor has Structure 2,

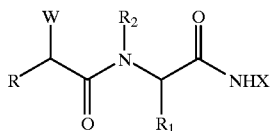

Structure 2 wherein
R is H, lower alkyl, branched alkyl, fluoroalkyl, perfluoroalkyl, carboxyalkyl, hydroxyalkyl, aryl, monosubstituted aryl, disubstituted aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, or $(CH_2)_n N=CNR^bR^c$, wherein n=1, 2, 3 or 4 and $R^a$, $R^b$, and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^1$ is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, $(CH_2)_n N=CNR^bR^c$, wherein n=1, 2, 3 or 4 and $R^a$, $R^b$ or $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, $(CH_2)_n N=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, isoquinolinyl, quinoxalinylalkyl, quinazolinylalkyl, benzimidazolylalkyl, benzothiazolylalkyl, or benzoxazolylalkyl.

30. The pharmaceutical composition of claim 28, wherein said efflux pump inhibitor has Structure 3,

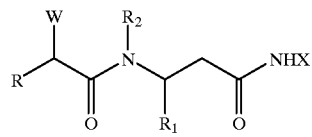

Structure 3 wherein
R is H, lower alkyl, branched alkyl, fluoroalkyl, perfluoroalkyl, carboxy-alkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, or $(CH_2)_n N=CNR^bR^c$ wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^1$ is H, lower alkyl, branched alkyl, fluoroalkyl, perfluoroalkyl, carboxy-alkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, or $(CH_2)_n N=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, $(CH_2)_n N=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)furyl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, isoquinolinyl, quinoxalinylalkyl, quinazolinylalkyl, benzimidazolylalkyl, benzothiazolylalkyl, or benzoxazolylalkyl.

31. The pharmaceutical composition of claim 28, wherein said efflux pump inhibitor has structure 4,

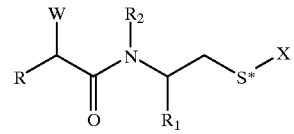

Structure 4 wherein
S* is NH, O, or $SO_t$ (t=0, 1, or 2);

R is H, lower alkyl, branched alkyl, fluoroalkyl, perfluoroalkyl, carboxyalkyl, hydroxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_n NR^bR^c$, $(CH_2)_n NHC=(NR^a)NR^bR^c$, $(CH_2)_n SC=(NR^a)NR^bR^c$, $(CH_2)_n C=(NR^a)NR^bR^c$, $(CH_2)_n N=CNR^bR^c$, wherein n=1, 2, 3 or 4 and $R^a$, $R^b$ and $R^c$ are independently H, alkyl, phenyl, benzyl, cyano, hydroxy, or nitro, or $R^a+R^b$ or $R^b+R^c$ is $(CH_2)_{2-3}$ or —CH=CH—;

$R^1$ is H, alkyl, branched alkyl, fluoroalkyl, perfluoroalkyl, carboxyalkyl, aryl, 2-(or 3-)thienyl, 2-(or 3-)furyl, or 2-(3- or 4-)pyridyl, arylalkyl, thienylalkyl, furylalkyl, pyridylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

$R^2$ is H, lower alkyl, branched alkyl, fluoroalkyl, perfluoroalkyl, aryl, 2-(or 3-)thienyl, 2-(or 3-)furyl, or 2-(3- or 4-)-pyridyl, benzofuranyl, benzothienyl, indolyl, benzimidazolyl, benzothiazolyl, benzoxazolyl, arylalkyl, thienylalkyl, furylalkyl, pyridylalkyl, benzofuranylalkyl, benzothienylalkyl, indolylalkyl, $(CH_2)_nNR^bR^c$, $(CH_2)_nNHC=(NR^a)NR^bR^c$, $(CH_2)_nSC=(NR^a)NR^bR^c$, $(CH_2)_nC=(NR^a)NR^bR^c$, $(CH_2)_nN=CNR^bR^c$, wherein n=1, 2, 3 or 4 and $R^a$, $R^b$ and $R^c$ are independently H, lower alkyl, phenyl, benzyl, cyano, hydroxy, or nitro, or $R^a+R^b$ or $R^b+R^c$ is $(CH_2)_{2-3}$ or —CH=CH—;

W is (alpha-aminoacyl)amido, aminoalkyl, amino, azaheterocycles, substituted azaheterocycles, hydroxy, alkoxy, alkylthio, guanidino, amidino, or halogen; and X is aryl, 2-(or 3-)thienyl, 2-(or 3-)fiiryl, or 2-(3- or 4-)pyridyl, tetrahydronaphthyl, indanyl, quinolinyl, isoquinolinyl, quinoxalinyl, quinazolinyl, benzimidazolyl, benzothiazolyl, benzoxazolyl, arylalkyl, thienylalkyl, furylalkyl, pyridylalkyl, quinolinylalkyl, isoquinolinylalkyl, quinoxalinylalkyl, quinazolinylalkyl, benzimidazolylalkyl, benzothiazolylalkyl, or benzoxazolylalkyl.

32. The pharmaceutical composition of claim 28, wherein said microbe is a bacterium.

33. The pharmaceutical composition of claim 28, further comprising an antimicrobial agent.

34. The pharmaceutical composition of claim 33, wherein said microbe is a bacterium.

35. The pharmaceutical composition of claim 34, wherein said antimicrobial agent is an antibacterial agent.

* * * * *